(12) United States Patent
Odidi

(10) Patent No.: US 10,653,776 B2
(45) Date of Patent: *May 19, 2020

(54) COMPOSITIONS AND METHODS FOR REDUCING OVERDOSE

(71) Applicant: Isa Odidi, Toronto (CA)

(72) Inventor: Isa Odidi, Toronto (CA)

(73) Assignee: Intellipharmaceutics Corp., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/358,392

(22) Filed: Mar. 19, 2019

(65) Prior Publication Data

US 2019/0275153 A1    Sep. 12, 2019

Related U.S. Application Data

(63) Continuation of application No. 15/602,845, filed on May 23, 2017, now Pat. No. 10,293,046, which is a
(Continued)

(51) Int. Cl.
*A61K 9/20*   (2006.01)
*A61K 9/28*   (2006.01)
(Continued)

(52) U.S. Cl.
CPC ............ *A61K 47/02* (2013.01); *A61K 9/2013* (2013.01); *A61K 9/2018* (2013.01);
(Continued)

(58) Field of Classification Search
CPC ......... A61K 47/02; A61K 47/36; A61K 9/28; A61K 47/32; A61K 47/26; A61K 47/12; A61K 47/183; A61K 47/20; A61K 47/38; A61K 31/616; A61K 9/5015; A61K 9/5026; A61K 9/5031; A61K 31/37; A61K 9/501; A61K 9/282; A61K 9/2853; A61K 9/2886;
(Continued)

(56) References Cited

U.S. PATENT DOCUMENTS 3,254,088 A   5/1966  Lewenstein et al.
3,493,657 A   2/1970  Fishman et al.
(Continued)

FOREIGN PATENT DOCUMENTS

AU    769952 B2    6/2001
EP    2374460 A1   12/2008
(Continued)

OTHER PUBLICATIONS

Treweek, Jennifer et al. "An Antidote for Acute Cocaine Toxicity". ACS' Journal Molecular Pharmaceuticals; (2012) pp. 969-978.
(Continued)

*Primary Examiner* — Trevor Love
(74) *Attorney, Agent, or Firm* — Wiggin and Dana LLP; Anthony D. Sabatelli

(57) ABSTRACT

Drug delivery formulations, uses thereof and methods of making same are provided in order to reduce the potential for abuse, misuse or improper administration of an addictive substance or any active substance and to prevent, reduce, inhibit, or delay purposeful or accidental overdose of an active substance by ingesting too many dosage forms at once, for example.

49 Claims, 35 Drawing Sheets

Related U.S. Application Data continuation of application No. 15/409,170, filed on Feb. 24, 2017, now Pat. No. 9,801,939, which is a continuation of application No. 15/271,469, filed on Sep. 21, 2016, now Pat. No. 9,700,515, which is a continuation of application No. 14/790,101, filed on Jul. 2, 2015, now Pat. No. 9,522,119.

(51) Int. Cl.

| | | |
|---|---|---|
| *A61K 9/48* | (2006.01) | |
| *A61K 9/50* | (2006.01) | |
| *A61K 31/00* | (2006.01) | |
| *A61K 31/135* | (2006.01) | |
| *A61K 31/167* | (2006.01) | |
| *A61K 31/192* | (2006.01) | |
| *A61K 31/197* | (2006.01) | |
| *A61K 31/366* | (2006.01) | |
| *A61K 31/37* | (2006.01) | |
| *A61K 31/4439* | (2006.01) | |
| *A61K 31/4458* | (2006.01) | |
| *A61K 31/485* | (2006.01) | |
| *A61K 31/515* | (2006.01) | |
| *A61K 31/5513* | (2006.01) | |
| *A61K 31/616* | (2006.01) | |
| *A61K 47/02* | (2006.01) | |
| *A61K 47/12* | (2006.01) | |
| *A61K 47/18* | (2017.01) | |
| *A61K 47/20* | (2006.01) | |
| *A61K 47/26* | (2006.01) | |
| *A61K 47/32* | (2006.01) | |
| *A61K 47/36* | (2006.01) | |
| *A61K 47/38* | (2006.01) | |

(52) U.S. Cl.
CPC .......... *A61K 9/2027* (2013.01); *A61K 9/2054* (2013.01); *A61K 9/2059* (2013.01); *A61K 9/28* (2013.01); *A61K 9/282* (2013.01); *A61K 9/2813* (2013.01); *A61K 9/2846* (2013.01); *A61K 9/2853* (2013.01); *A61K 9/2886* (2013.01); *A61K 9/485* (2013.01); *A61K 9/4808* (2013.01); *A61K 9/4866* (2013.01); *A61K 9/4891* (2013.01); *A61K 9/501* (2013.01); *A61K 9/5015* (2013.01); *A61K 9/5026* (2013.01); *A61K 9/5031* (2013.01); *A61K 31/00* (2013.01); *A61K 31/135* (2013.01); *A61K 31/167* (2013.01); *A61K 31/192* (2013.01); *A61K 31/197* (2013.01); *A61K 31/366* (2013.01); *A61K 31/37* (2013.01); *A61K 31/4439* (2013.01); *A61K 31/4458* (2013.01); *A61K 31/485* (2013.01); *A61K 31/515* (2013.01); *A61K 31/5513* (2013.01); *A61K 31/616* (2013.01); *A61K 47/12* (2013.01); *A61K 47/183* (2013.01); *A61K 47/20* (2013.01); *A61K 47/26* (2013.01); *A61K 47/32* (2013.01); *A61K 47/36* (2013.01); *A61K 47/38* (2013.01); *A61K 9/2031* (2013.01); *A61K 9/4858* (2013.01)

(58) Field of Classification Search
CPC .... A61K 9/4808; A61K 31/00; A61K 31/485; A61K 9/2027; A61K 9/2059; A61K 9/2054; A61K 9/2018; A61K 9/2013; A61K 9/2813; A61K 9/2846; A61K 9/485; A61K 9/4891; A61K 31/4439; A61K 31/197; A61K 31/135; A61K 31/4458; A61K 31/366; A61K 31/167; A61K 31/515; A61K 31/5513; A61K 31/192; A61K 9/4866; A61K 9/2031; A61K 9/4858

See application file for complete search history.

(56) References Cited

U.S. PATENT DOCUMENTS

| | | |
|---|---|---|
| 3,845,770 A | 11/1974 | Higuchi et al. |
| 3,916,899 A | 11/1975 | Theeuwes et al. |
| 3,980,766 A | 9/1976 | Shaw et al. |
| 4,008,719 A | 2/1977 | Theeuwes et al. |
| 4,036,228 A | 7/1977 | Theeuwes et al. |
| 4,070,494 A | 1/1978 | Hoffmeister et al. |
| 4,175,119 A | 11/1979 | Porter |
| 4,327,725 A | 5/1982 | Cortese et al. |
| 4,459,278 A | 7/1984 | Porter |
| 4,612,008 A | 9/1986 | Wong et al. |
| 4,786,505 A | 11/1988 | Lovgren et al. |
| 4,812,446 A | 3/1989 | Brand |
| 5,202,128 A | 4/1993 | Morella et al. |
| 5,290,816 A | 3/1994 | Blumberg |
| 5,464,632 A | 11/1995 | Cousin et al. |
| 5,474,757 A | 12/1995 | Yang |
| 5,643,560 A | 7/1997 | Bergwitz-Larsen et al. |
| 6,027,748 A | 2/2000 | Conte et al. |
| 6,103,258 A | 8/2000 | Simon |
| 6,277,384 B1 | 8/2001 | Kaiko et al. |
| 6,309,668 B1 | 10/2001 | Bastin et al. |
| 6,375,957 B1 | 4/2002 | Kaiko et al. |
| 6,475,494 B2 | 11/2002 | Kaiko et al. |
| 6,488,693 B2 | 12/2002 | Gannoe et al. |
| 6,604,650 B2 | 8/2003 | Sagar |
| 6,627,635 B2 | 9/2003 | Palermo et al. |
| 6,673,814 B2 | 1/2004 | Joshi et al. |
| 6,696,088 B2 | 2/2004 | Oshlack et al. |
| 6,881,420 B2 | 4/2005 | Flashner-Barak |
| 7,105,180 B2 | 9/2006 | Schmitt |
| 7,157,100 B2 | 1/2007 | Doshi et al. |
| 7,157,103 B2 | 1/2007 | Sackler |
| 7,195,778 B2 | 3/2007 | Fleshner-Barak |
| 7,201,920 B2 | 4/2007 | Kumar |
| 7,255,878 B1 | 8/2007 | Lahav |
| 7,295,890 B2 | 11/2007 | Jean-Pierre |
| 7,375,083 B2 | 5/2008 | Mickle et al. |
| 7,670,624 B2 | 3/2010 | Tsutsumi et al. |
| 7,674,799 B2 | 3/2010 | Chapman et al. |
| 7,776,314 B2 | 8/2010 | Bartholomaus et al. |
| 7,842,307 B2 | 11/2010 | Oshlack et al. |
| 7,884,136 B2 | 2/2011 | Oberegger et al. |
| 7,914,848 B2 | 3/2011 | Breder et al. |
| 7,943,173 B2 | 5/2011 | Breder et al. |
| 7,955,619 B2 | 6/2011 | Shah et al. |
| 8,114,383 B2 | 2/2012 | Bartholomaus et al. |
| 8,106,016 B2 | 3/2012 | Moncrief et al. |
| 8,598,191 B2 | 12/2013 | Liang et al. |
| 2003/0044458 A1 | 3/2003 | Wright et al. |
| 2003/0175349 A1 | 3/2003 | Garg et al. |
| 2005/0054561 A1 | 3/2005 | Mickle et al. |
| 2005/0186268 A1 | 8/2005 | Hoshi et al. |
| 2005/0196436 A1 | 9/2005 | Chantranukul et al. |
| 2005/0220715 A1 | 10/2005 | Lin |
| 2005/0281748 A1 | 12/2005 | Hirsh et al. |
| 2006/0004193 A1 | 1/2006 | Muller et al. |
| 2006/0099246 A1 | 5/2006 | Tanner et al. |
| 2006/0153909 A1 | 7/2006 | Motoune et al. |
| 2007/0066537 A1 | 3/2007 | Mickle et al. |
| 2007/0077293 A1 | 4/2007 | Park et al. |
| 2008/0063725 A1 | 3/2008 | Guimberteau et al. |
| 2008/0090771 A1 | 4/2008 | Moncrief |
| 2009/0011016 A1 | 1/2009 | Caily-Dufestel et al. |
| 2009/0175937 A1 | 7/2009 | Rahmouni et al. |
| 2010/0144645 A1 | 6/2010 | Kirk et al. |
| 2010/0183713 A1 | 7/2010 | Tsutsumi et al. |
| 2010/0197571 A1 | 8/2010 | Kanikanti et al. |
| 2010/0291205 A1 | 11/2010 | Downie et al. |
| 2010/0297226 A1 | 11/2010 | Penhasi et al. |
| 2011/0020442 A1 | 1/2011 | Becourt et al. |

(56) References Cited

U.S. PATENT DOCUMENTS

| | | |
|---|---|---|
| 2011/0020451 A1 | 1/2011 | Bartholomäus et al. |
| 2011/0033506 A1 | 2/2011 | Penhasi et al. |
| 2011/0135722 A1 | 6/2011 | Criere et al. |
| 2011/0223244 A1 | 9/2011 | Liversidge et al. |
| 2012/0065221 A1 | 3/2012 | Babul |
| 2012/0076865 A1 | 3/2012 | Allphin et al. |
| 2012/0093926 A1 | 4/2012 | Bodinge et al. |
| 2012/0207825 A1 | 8/2012 | Roy et al. |
| 2012/0244216 A1 | 9/2012 | Shah et al. |
| 2012/0321716 A1 | 12/2012 | Vachon et al. |
| 2013/0034503 A1 | 2/2013 | Howard et al. |
| 2013/0295170 A1 | 7/2013 | Dordunoo |
| 2014/0271851 A1 | 9/2014 | Fathi et al. |

FOREIGN PATENT DOCUMENTS

| | | |
|---|---|---|
| EP | 2345408 A2 | 7/2011 |
| JP | 62215538 A | 9/1987 |
| WO | 2001037817 A1 | 5/2001 |
| WO | 2002005647 A1 | 1/2002 |
| WO | 2003013471 A2 | 2/2003 |
| WO | 2005046634 A2 | 5/2005 |
| WO | 2006044805 A2 | 4/2006 |
| WO | 2006085723 A1 | 8/2006 |
| WO | 2006138278 A1 | 12/2006 |
| WO | 2011066980 A2 | 6/2011 |
| WO | 2011140446 A2 | 11/2011 |
| WO | 2012112952 A1 | 8/2012 |
| WO | 2014085599 A1 | 6/2014 |
| WO | 2015120201 A1 | 8/2015 |

OTHER PUBLICATIONS

International Search Report and Written Opinion mained in PCT/CA2015/050567 dated Sep. 21, 2015.

Canadian Office Action dated Jan. 25, 2016 from related Canadian Application No. 2,910,865, 5 pages.

COMPOSITIONS AND METHODS FOR REDUCING OVERDOSE

FIELD OF THE INVENTION

The present invention relates to compositions and methods for reducing overdose and reducing drug abuse, in particular to compositions, methods, uses thereof, and methods for making same.

BACKGROUND

Substance abuse, also known as drug abuse, is a patterned use of a substance in which the user consumes the substance in amounts or uses methods with these substances which are harmful to themselves or others. A well known and documented form of substance abuse, especially in the use of opioid analgesics, is that involving the deliberate crushing, snorting or injecting of solid oral medication intended to be taken intact in order to get a feeling of euphoria.

Almost all of the abuse-deterrent formulations currently known are aimed at preventing patients from crushing, snorting, or injecting them. While these are very high-risk behaviours, they likely represent a small minority of patients who abuse prescribed opioids. Most patients who are abusing opioids are likely taking more than prescribed by mouth, or combining them with other medications and drugs.

The Food and Drug Administration (FDA) corroborates this observation. According to this regulatory agency, "opioid analgesics are often manipulated for purposes of abuse. Most abuse-deterrent technologies developed to date are designed to make product manipulation more difficult or to make abuse of the manipulated product less attractive or rewarding. However, these technologies have not yet proven successful at deterring the most common form of abuse—swallowing a number of intact pills or tablets to achieve a feeling of euphoria." (see FDA Draft Guidance for Industry title Abuse-Deterrent Opioids—Evaluation and Labeling of January 2013).

Substance abuse can lead to addiction, serious adverse events, or in some cases, overdose and death. Overdose and death can also result from mistaken or intentional oral ingestion of a number of intact pharmaceutical unit dosage formulations, such as pills. Drug overdose is the leading cause of accidental death in the United States, causing more deaths than motor vehicle crashes in 2010 among people 25 to 64 years old. It is now generally accepted that the leading cause of death in drug overdoses in the U.S. today is prescription drugs. Drug overdose death rates have been rising steadily since 1992 with a 102% increase from 1999 to 2010 alone.

A major issue of great concern is that there continues to be reports of people deliberately or mistakenly swallowing a number of intact pills or tablets despite instructions not to do so, and suffering serious adverse effects as a result. Products containing active ingredients that will produce an emotional, psychological, euphoric, depressive, or generally psychedelic experience are particularly vulnerable to this form of abuse.

Attempts have been made in the past to control abuse or overdose from swallowing a number of intact solid dosage forms, but formulations and methods currently taught have not successfully prevented overdose from swallowing a number of intact tablets or capsules. Some of these approaches are sometimes executed after the fact, i.e., directed at a rescue therapy after overdose has occurred and do not necessarily address the issue of preventing overdose from occurring in the first place.

U.S. Pat. Nos. 7,375,083 and 8,106,016 relate to pharmaceutical compositions comprised of a chemical moiety attached to an active agent in a manner that substantially decreases the potential of the active agent to cause overdose or to be abused. When delivered at the proper dosage the pharmaceutical composition provides therapeutic activity similar to that of the parent active agent.

U.S. Pat. No. 5,474,757 relates to a method of preventing acetaminophen (APAP)-induced hepatotoxicity utilizing diallyl sulfide (DAS) and diallyl sulfone ($DASO_2$). DAS and $DASO_2$ are prepared as an oral dosage form or injected. In a preferred embodiment, diallyl sulfone is added to a dosage form of acetaminophen in an amount effective to prevent the metabolism of said unit dose of acetaminophen into its hepatotoxic metabolites. In certain preferred embodiments, the above formulations further include an effective amount of N-acetylcysteine to detoxify hepatotoxic metabolites of acetaminophen.

U.S. Pat. No. 6,604,650 relates to a medicine-dispensing system having a medication reminder to assist the patient in following a drug regimen. In an example embodiment, a medication reminder comprises a timer programmable to a predetermined interval. A user-alert is responsive to the timer, reminding the user to take a dose of medicine at the predetermined interval. A sensor detects whether a dose of medicine has been taken and a dose-indication informs the user of the time since a last medication. The dose indication further informs the user as to whether to take a next medication dose. Time of the last dose is determined by the timer receiving a signal from the sensor. A communications interface enables programming of a parameter associated with administering a medication.

U.S. Pat. No. 7,295,890 relates to a drug compliance monitoring system that provides a patient with a portable medication dispenser programmed with medication-taking data. The dispenser alerts the patient to take a dose of medication and gathers compliance data relating to the medication-taking data. The compliance data is accessible to a physician, or other care givers, etc., via a network database.

U.S. Pat. No. 5,643,560 relates to the use of, and methods to obtain, ion exchanger complexes with psychotropic drugs for reducing toxic side effects and lethality when overdosing the drug. The invention includes methods and compositions for modifying the total amount of drug released from the complex in the gastro-intestinal tract by adding a substance which affects the ion exchange process. The additional substance may be a salt which generates an ion with higher or similar affinity to the ion exchanger when compared to the drug. The additional substance may be a counter ion in an additional complex with an ion exchanger.

U.S. Patent Application Publication No. 2013/0034503 relates to a method and composition for treating a patient that prevents or reduces drug abuse and overdose events with drugs. The method comprises: oral administration of a pharmaceutical composition comprising at least one drug bound to at least one ion exchange resin as a resinate, said ion exchange resins being selected from the group consisting of a cationic ion exchange resin and a anionic ion exchange resin, each said ion exchange resin being bound to at least one drug, wherein each said bound drug, measured as the unbound state, is less than about 75 percent of its saturation concentration in its resinate.

Australian Patent No. 769952 relates to an orally administrable pharmaceutical product comprising an information carrier having a form and composition such that information is recorded by the carrier; wherein the information carrier comprises a resistant material that is resistant to the gastric environment. The presence of the information carrier facilitates the treatment of overdose patients who have consumed large quantities of the pharmaceutical product. The information may relate to the characteristics of the product and may be recorded by engraving characters into the information carrier.

U.S. Pat. No. 3,254,088 relates to the preparation of naloxone and its activity as a narcotic antagonist. U.S. Pat. No. 3,493,657 relates to the combination of morphine and naloxone as a composition for parenteral use "which has a strong analgesic, as well as antagonistic effect, without the occurrence of undesired or dangerous side effects."

The combination of pentazocine and naloxone has been utilized in tablets available in the United States, commercially available as Talwin® from Sanofi-Winthrop. Talwin® contains pentazocine hydrochloride equivalent to 50 mg base and naloxone hydrochloride equivalent to 0.5 mg base. Talwin® is indicated for the relief of moderate to severe pain. The amount of naloxone present in this combination has no action when taken orally, and will not interfere with the pharmacologic action of pentazocine.

However, this amount of naloxone given by injection has profound antagonistic action to narcotic analgesics. Thus, the inclusion of naloxone is intended to curb a form of abuse of oral pentazocine, which occurs when the formulation is solubilized and injected. Therefore, this dosage has lower potential for parenteral abuse than previous oral pentazocine formulations.

Another example of attempts at preventing the potential harmful effects of overdose includes compositions that have been coated with emetics in a quantity that if administered in moderation as intended no emesis occurs, however, if excessive amounts are consumed emesis is induced therefore preventing overdose.

Scientists have reported the development and successful testing in laboratory mice of a substance that shows promise for becoming the first antidote for cocaine toxicity in humans. According to a report in ACS' Journal Molecular Pharmaceutics, the new so-called "passive vaccine" reversed the motor impairment, seizures and other dangerous symptoms of a cocaine overdose, which claims thousands of lives each year among users of the illicit drug. Kim D. Janda and Jennifer B. Treweek explain that their previous research established the validity of using vaccines as treatments for drug addiction and contributed to the promotion of one cocaine-active vaccine (and three nicotine-active vaccines) to clinical evaluation in humans. These so-called "active" vaccines elicit antibodies that bind circulating cocaine (and nicotine) molecules in the blood and prevent these drug molecules from reaching the brain. In doing so, vaccinated patients are "immune" to the drug's effects, and as a result, they feel no pleasurable effects from the drug if they backslide during recovery. The report describes the development of a cocaine passive vaccine, which consists of pre-formed human antibodies against cocaine that are 10 times more potent in binding cocaine molecules. This improved potency accelerates their ability to reverse cocaine toxicity, where time is of the essence. When administered by emergency medical teams or in hospital emergency departments, these passive vaccines could represent a life-saving therapeutic for overdose victims.

U.S. Pat. Nos. 6,277,384, 6,375,957, and 6,475,494 relate to oral dosage forms comprising a combination of an orally analgesically effective amount of an opioid agonist and an orally active opioid antagonist, the opioid antagonist being included in a ratio to the opioid agonist to provide a combination product which is analgesically effective when the combination is administered orally, but which is aversive in a physically dependent subject. Preferably, the amount of opioid antagonist included in the combination product provides at least a mildly negative, "aversive" experience in physically dependent addicts (e.g., precipitated abstinence syndrome).

There is still a need for formulations that prevent, inhibit, or delay drug abuse such as by chewing and/or licking intact tablet(s), snorting, inhalation, smoking, and/or insufflation of pulverized or milled tablet(s) either accidentally or intentionally.

There is still a need for formulations that prevent, inhibit, or delay overdose by ingesting too many unit dosage forms, either accidentally or intentionally.

SUMMARY

According to an aspect, there is provided a unit dose formulation comprising at least one active substance, wherein release of said at least one active substance is inhibited when the number of unit dosage forms ingested exceeds a predetermined number.

In an aspect, the unit dose formulation further comprises at least one actuator and at least one regulator, whereby when the unit dose formulation is exposed to a fluid media having a process variable, and a predetermined threshold is established for the process variable, said at least one regulator is capable of adjusting the variable to control the release of said at least one active substance via said at least one actuator.

In an aspect, said at least one regulator is present in an amount sufficient to raise the variable above the threshold, such that dissolution of said at least one actuator and release of said at least one active substance via the actuator is inhibited when the number of unit dosage forms ingested exceeds the predetermined number.

In an aspect, said at least one regulator is present in an amount sufficient to decrease the variable below the threshold, such that dissolution of said at least one actuator and release of said at least one active substance via the actuator is inhibited when the number of unit dosage forms ingested exceeds the predetermined number.

In an aspect, the fluid media is an acidic media.

In an aspect, the fluid media is a basic media.

In an aspect, the variable is pH.

In an aspect, the regulator and/or actuator is a physical/chemical barrier.

In an aspect, the regulator is a pH independent barrier and the actuator is a pH dependent barrier.

In an aspect, said at least one regulator comprises at least one alkalinizing agent.

In an aspect, said at least one alkalinizing agent is selected from the group consisting of alkaline earth metal salts, alkali metal salts, aluminum salts, amino acids, amino acid derivatives, and combinations thereof.

In an aspect, said at least one alkalinizing agent is selected from the group consisting of magnesium hydroxide, magnesium trisilicate, aluminum hydroxide, magnesium oxide, calcium carbonate, sodium bicarbonate, sodium citrate, sodium carbonate, sodium acetate, magnesium carbonate, L-arginine, meglumine, and combinations thereof.

In an aspect, said at least one alkalinizing agent is magnesium hydroxide.

In an aspect, aid at least one regulator comprises at least one acidifying agent.

In an aspect, said at least one regulator is selected from the group consisting of an inorganic acid, an organic acid, and combinations thereof.

In an aspect, said at least one acidifying agent is selected from the group consisting of hydrochloric acid, sulfuric acid, nitric acid, lactic acid, phosphoric acid, citric acid, malic acid, fumaric acid, stearic acid, tartaric acid, boric acid, borax, benzoic acid, and combinations thereof.

In an aspect, said at least one acidifying agent is fumaric acid and/or citric acid.

In an aspect, said at least one actuator comprises at least one acid labile substance.

In an aspect, said at least one acid labile substance is selected from the group consisting of sulfonamide-based polymers and copolymers, amine functional polymers such as polyvinyl pyridine polymers and copolymers, polysaccharides such as chitosan, poly(vinylpyrrolidone-co-dimethylmaleic anhydride) (PVD), dimethylaminoethyl methacrylate copolymers such as Eudragit E, Eudragit E interpolyelectrolyte complex, Eudragit E polyamopholyte complex, Eudragit E interpolyelectrolyte complex with Eudragit L and/or Eudragit S, derivatives thereof, and combinations thereof.

In an aspect, said at least one acid labile coat and/or substance comprises Eudragit E.

In an aspect, said at least one actuator comprises at least one base labile substance.

In an aspect, said at least one base labile substance is selected from the group consisting of pharmaceutically acceptable ethers, esters, ketones, epoxies, polyamides, polysiloxanes, enteric polymers, anionic copolymers based on methacrylic acid and methyl methacrylate, and combinations thereof.

In an aspect, said at least one base labile coat and/or substance comprises at least one enteric polymer, such as Eudragit L or S.

In an aspect, wherein dissolution of said at least one actuator and release of said at least one active substance is reduced upon dissolution of a threshold amount of said at least one regulator.

In an aspect, wherein dissolution of said at least one actuator and release of said at least one active substance decreases in the presence of increasing concentrations of at least one regulator.

In an aspect, the rate of dissolution of said at least one actuator is inversely proportional to the number of unit dose formulations ingested.

In an aspect, wherein, when the number of unit dosage forms ingested exceeds a predetermined number, said at least one regulator increases the pH to inhibit dissolution of said at least one actuator and inhibit release of said at least one active substance.

In an aspect, wherein, when the number of unit dosage forms ingested exceeds a predetermined number, said at least one regulator decreases the pH to inhibit dissolution of said at least one actuator and inhibit release of said at least one active substance.

In an aspect, the predetermined number is less than 20.

In an aspect, the predetermined number is 1, 2, 3, 4, or 5.

In an aspect, the predetermined number is 1 or 2.

In an aspect, the unit dose formulation further comprises at least one agent selected from the group consisting of an abuse deterrent coloring agent; a controlled release agent; a vicosity imparting agent; a gelling agent; polyethylene oxide; crospovidone; Eudragit RL; Eudragit RS, and combinations thereof.

In an aspect, the unit dose formulation further comprises at least one abuse deterrent coloring agent.

In an aspect, wherein said at least one abuse deterrent coloring agent is brilliant blue; typically, Aluminum Lake Blue #1.

In an aspect, the unit dose formulation further comprises at least one agent selected from the group consisting of a chewing discouraging agent, a licking discouraging agent, an insufflation discouraging agent, a snorting discouraging agent, an inhalation discouraging agent, and combinations thereof.

In an aspect, the inhalation discouraging agent is selected from the group consisting of a coloring agent, a tussigenic agent, an irritant, and combinations thereof.

In an aspect, said at least one active substance is at least one addictive substance.

In an aspect, said at least one active substance is at least one opioid agonist and/or at least one narcotic analgesic.

In an aspect, said at least one active substance has an analgesic ceiling effect.

In an aspect, the unit dose formulation in the form of a bead, tablet, capsule, granule, and/or pellet.

In an aspect, said at least one active substance is in an amount of from about 0.1 mg to about 1000 mg; said at least one actuator is in an amount of from about 0.5 mg to about 500 mg; and/or said at least one regulator is in an amount of from about 0.5 mg to about 500 mg.

In an aspect, said at least one actuator is present in an amount of from 0.5 mg/cm$^2$ to 200 mg/cm$^2$ or from 1 mg/cm$^2$ to 100 mg/cm$^2$ or from 2 mg/cm$^2$ to 150 mg/cm$^2$ or from about 4 mg/cm$^2$ to about 100 mg/cm$^2$ or from 8 mg/cm$^2$ to 50 mg/cm$^2$.

In an aspect, said at least one actuator is present in an amount that yields from about 1% to about 200% weight gain, from about 1% to about 70% or from about 1% to about 50% weight gain.

In an aspect, said at least one regulator is present in an amount that yields from about 1% to about 200% weight gain, from about 5% to about 80%, from about 1% to about 70% weight gain, from about 1% to about 50% or from about 5% to about 50% weight gain.

In an aspect, wherein release of said at least one active substance is a lag time, delayed release, no release or insignificant release of said at least one active substance.

According to an aspect, there is provided a unit dose formulation comprising:

a core comprising at least one active substance;

at least one acid labile coat surrounding the core; and at least one alkalinizing coat surrounding said at least one acid labile coat.

According to an aspect, there is provided a unit dose formulation comprising:

a core comprising at least one active substance and at least one acid labile substance; and at least one alkalinizing coat surrounding the core.

According to an aspect, there is provided a unit dose formulation comprising:

a core;

at least one acid labile coat surrounding the core, said at least one acid labile coat comprising at least one acid labile substance and at least one active substance; and at least one alkalinizing coat surrounding said at least one acid labile coat.

According to an aspect, there is provided a unit dose formulation comprising:
a core;
at least one coat comprising at least one active substance;
at least one acid labile coat surrounding said at least one coat; and
at least one alkalinizing coat surrounding said at least one acid labile coat.

According to an aspect, there is provided a unit dose formulation comprising:
at least one active substance;
at least one acid labile coat surrounding said at least one active substance; and
at least one alkalinizing coat surrounding said at least one acid labile coat.

According to an aspect, there is provided a unit dose formulation comprising:
a mixture of at least one active substance and at least one acid labile substance; and
at least one alkalinizing coat surrounding the mixture.

In an aspect, the mixture is a homogeneous mixture.

In an aspect, said at least one alkalinizing coat is present in an amount sufficient to raise the pH of the stomach, such that dissolution of said at least one acid labile coat and release of said at least one active substance is inhibited when the number of unit dosage forms ingested exceeds a predetermined number.

In an aspect, said at least one alkalinizing coat is present in an amount sufficient to raise the pH of the stomach, such that dissolution of said at least one acid labile substance and release of said at least one active substance is inhibited when the number of unit dosage forms ingested exceeds a predetermined number.

In an aspect, the predetermined number is less than 20.

In an aspect, the predetermined number is 1, 2, 3, 4, or 5.

In an aspect, the predetermined number is 1 or 2.

In an aspect, dissolution of said at least one acid labile coat and release of said at least one active substance is reduced upon dissolution of a threshold amount of said at least one alkalinizing coat.

In an aspect, dissolution of said at least one acid labile substance and release of said at least one active substance is reduced upon dissolution of a threshold amount of said at least one alkalinizing coat.

In an aspect, dissolution of said at least one acid labile coat and release of said at least one active substance is dependent upon the concentration of at least one alkalinizing agent in said at least one alkalinizing coat.

In an aspect, dissolution of said at least one acid labile substance and release of said at least one active substance decreases in the presence of increasing concentrations of at least one alkalinizing agent in said at least one alkalinizing coat.

In an aspect, the rate of dissolution of said at least one acid labile coat is inversely proportional to the number of unit dose formulations ingested.

In an aspect, the rate of dissolution of said at least one acid labile substance is inversely proportional to the number of unit dose formulations ingested.

In an aspect, wherein, when the number of unit dosage forms ingested exceeds a predetermined number, said at least one alkalinizing coat increases stomach pH to inhibit dissolution of said at least one acid labile coat and inhibit release of said at least one active substance.

In an aspect, wherein, when the number of unit dosage forms ingested exceeds a predetermined number, said at least one alkalinizing coat increases stomach pH to inhibit dissolution of said at least one acid labile substance and inhibit release of said at least one active substance.

In an aspect, each of said at least one alkalinizing coat comprises at least one alkalinizing agent.

In an aspect, dissolution of said at least one acid labile coat and/or substance and release of said at least one active substance in aqueous medium is dependent upon the concentration of said at least one alkalinizing agent in the aqueous medium.

In an aspect, said at least one alkalinizing agent is present in said at least one alkalinizing coat in an amount such that:
when less than a predetermined number of unit dose formulations is ingested, the gastric pH remains sufficiently acidic to dissolve said at least one acid labile coat and/or substance and release said at least one active substance; and
when the predetermined number or more of the unit dose formulations is ingested, the gastric pH is alkalinized sufficiently to inhibit dissolution of said at least one acid labile coat and/or substance and release of said at least one active substance.

In an aspect, the predetermined number is 1, 2, 3, 4, or 5.

In an aspect, the predetermined number is 1 or 2.

In an aspect, said at least one alkalinizing agent is selected from the group consisting of alkaline earth metal salts, alkali metal salts, aluminum salts, amino acids, amino acid derivatives, and combinations thereof.

In an aspect, said at least one alkalinizing agent is selected from the group consisting of magnesium hydroxide, magnesium trisilicate, aluminum hydroxide, magnesium oxide, calcium carbonate, sodium bicarbonate, sodium citrate, sodium carbonate, sodium acetate, magnesium carbonate, L-arginine, meglumine, and combinations thereof.

In an aspect, said at least one alkalinizing agent is magnesium hydroxide.

In an aspect, each of said at least one acid labile coat comprises at least one acid labile substance.

In an aspect, said at least one acid labile substance is selected from the group consisting of sulfonamide-based polymers and copolymers, amine functional polymers such as polyvinyl pyridine polymers and copolymers, polysaccharides such as chitosan, poly(vinylpyrrolidone-co-dimethylmaleic anhydride) (PVD), dimethylaminoethyl methacrylate copolymers such as Eudragit E, Eudragit E interpolyelectrolyte complex, Eudragit E polyampholyte complex, Eudragit E interpolyelectrolyte complex with Eudragit L and/or Eudragit S, derivatives thereof, and combinations thereof.

In an aspect, said at least one acid labile coat and/or substance comprises Eudragit E.

In an aspect, said at least one acid labile coat and/or acid labile substance dissolves in a solution with a pH of less than about 6, 5, 4, 3, 2, or 1.

In an aspect, dissolution of said at least one acid labile coat and/or acid labile substance is inhibited in a solution with a pH of greater than about 3, 4, 5, or 6.

In an aspect, said at least one acid labile coat and/or said acid labile substance is soluble in stomach pH.

In an aspect, said at least one alkalinizing coat has at least one alkalinizing agent in an amount of at least about 1 mg per unit dosage formulation but such that when more unit dosage formulations than prescribed are swallowed at once, the pH of the stomach changes to an alkaline pH and release of said at least one active substance is inhibited.

In an aspect, the number of unit dosage formulations than that prescribed is about 1 to about 100 and the stomach pH is less than about 5, the pH of the stomach changes to alkaline pH.

In an aspect, the number of unit dosage formulations than that prescribed is is less than 20 and the stomach pH is less than about 4, the pH of the stomach changes to pH greater than about 4 and typically, greater than about 6.

In an aspect, said at least one active substance is homogenously mixed within the core; typically, the core comprises at least one disintegrant, at least one Eudragit RL and Eudragit RS, at least one coloring agent, and at least one polyethylene oxide.

In an aspect, the core comprises an outer active substance-releasing coat beneath said at least one acid labile coat and/or alkalinizing coat.

In an aspect, the core comprises a plurality of compressed granules.

In an aspect, the unit dosage formulation further comprises at least one agent selected from the group consisting of an abuse deterrent coloring agent; a controlled release agent; a vicosity imparting agent; a gelling agent; polyethylene oxide; crospovidone; Eudragit RL; Eudragit RS, and combinations thereof.

In an aspect, the unit dose formulation further comprises at least one abuse deterrent coloring agent.

In an aspect, wherein said at least one abuse deterrent coloring agent is brilliant blue; typically, Aluminum Lake Blue #1.

In an aspect, the unit dosage formulation further comprises at least one agent selected from the group consisting of a chewing discouraging agent, a licking discouraging agent, an insufflation discouraging agent, a snorting discouraging agent, an inhalation discouraging agent, and combinations thereof.

In an aspect, the inhalation discouraging agent is selected from the group consisting of a coloring agent, a tussigenic agent, an irritant, and combinations thereof.

In an aspect, the unit dose formulation further comprising said at least one abuse deterrent coloring agent.

In an aspect, wherein said at least one abuse deterrent coloring agent is brilliant blue; typically, Aluminum Lake Blue #1.

In an aspect, said at least one active substance is at least one addictive substance.

In an aspect, said at least one active substance is at least one opioid agonist and/or at least one narcotic analgesic.

In an aspect, said at least one active substance has an analgesic ceiling effect.

In an aspect, the unit dose formulation is in the form of a bead, tablet, capsule, granule, and/or pellet.

In an aspect, said at least one active substance is in an amount of from about 0.1 mg to about 1000 mg; said at least one acid labile coat is in an amount of from about 0.5 mg to about 500 mg; and/or said at least one alkalinizing coat is in an amount of from about 0.5 mg to about 500 mg.

In an aspect, said at least one acid labile coat is present in an amount of from 0.5 mg/cm$^2$ to 200 mg/cm$^2$ or from 1 mg/cm$^2$ to 100 mg/cm$^2$ or from 2 mg/cm$^2$ to 150 mg/cm$^2$ or from about 4 mg/cm$^2$ to about 100 mg/cm$^2$ or from 8 mg/cm$^2$ to 50 mg/cm$^2$.

In an aspect, said at least one acid labile coat and/or acid labile substance is present in an amount that yields from about 1% to about 200% weight gain, from about 1% to about 70% or from about 1% to about 50% weight gain.

In an aspect, said at least one alkalinizing coat has a thickness of from about 2 mg/cm$^2$ to about 100 mg/cm$^2$, or 15 mg/cm$^2$ to about 55 mg/cm$^2$, or 10 mg/cm$^2$ to about 40 mg/cm$^2$, or 40 mg/cm$^2$ to about 80 mg/cm$^2$, or 80 mg/cm$^2$ to about 100 mg/cm$^2$.

In an aspect, said at least one alkalinizing coat is present in an amount that yields from about 1% to about 200% weight gain, from about 5% to about 80%, from about 1% to about 70% weight gain, from about 1% to about 50% or from about 5% to about 50% weight gain.

In an aspect, said at least one alkalinizing coat is partially, substantially or completely surrounding.

In an aspect, said at least one acid labile coat is substantially or completely surrounding.

In an aspect, the unit dose formulation is an immediate release or controlled release medication.

In an aspect, the alkalinizing coat contains at least one alkalinizing agent that is capable of undergoing the following neutralization with stomach acid:

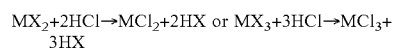

$$MX_2 + 2HCl \rightarrow MCl_2 + 2HX \text{ or } MX_3 + 3HCl \rightarrow MCl_3 + 3HX$$

where M is a metal ion and X is a basic ion.

According to an aspect, there is provided a unit dose formulation comprising:
a core comprising at least one active substance;
at least one base labile coat surrounding the core;
at least one acidifying coat surrounding said at least one base labile coat; and
at least one base labile coat surrounding said at least one acidifying coat.

According to an aspect, there is provided a unit dose formulation comprising:
a core comprising at least one active substance and at least one base labile substance;
at least one acidifying coat surrounding the core; and
at least one base labile coat surrounding said at least one acidifying coat.

According to an aspect, there is provided a unit dose formulation comprising:
a core;
at least one base labile coat surrounding the core, said at least one base labile coat comprising at least one base labile substance and at least one active substance;
at least one acidifying coat surrounding said at least one base labile coat; and
at least one base labile coat surrounding said at least one acidifying coat.

According to an aspect, there is provided a unit dose formulation comprising:
a core;
at least one coat comprising at least one active substance;
at least one base labile coat surrounding said at least one coat;
at least one acidifying coat surrounding said at least one base labile coat; and
at least one base labile coat surrounding said at least one acidifying coat.

According to an aspect, there is provided a unit dose formulation comprising:
at least one active substance;
at least one base labile coat surrounding said at least one active substance;
at least one acidifying coat surrounding said at least one base labile coat; and
at least one base labile coat surrounding said at least one acidifying coat.

According to an aspect, there is provided a unit dose formulation comprising:
a mixture of at least one active substance and at least one base labile substance;
at least one acidifying coat surrounding the mixture; and at least one base labile coat surrounding said at least one acidifying coat.

In an aspect, the mixture is a homogeneous mixture.

In an aspect, said at least one acidifying coat is present in an amount sufficient to lower the pH of the duodenum, such that dissolution of said at least one base labile coat and release of said at least one active substance is inhibited when the number of unit dosage forms ingested exceeds a predetermined number.

In an aspect, said at least one acidifying coat is present in an amount sufficient to lower the pH of the duodenum, such that dissolution of said at least one base labile substance and release of said at least one active substance is inhibited when the number of unit dosage forms ingested exceeds a predetermined number.

In an aspect, the predetermined number is less than 20.

In an aspect, the predetermined number is 1, 2, 3, 4, or 5.

In an aspect, the predetermined number is 1 or 2.

In an aspect, dissolution of said at least one base labile coat and release of said at least one active substance is reduced upon dissolution of a threshold amount of said at least one acidifying coat.

In an aspect, dissolution of said at least one base labile substance and release of said at least one active substance is reduced upon dissolution of a threshold amount of said at least one acidifying coat.

In an aspect, dissolution of said at least one base labile coat and release of said at least one active substance is dependent upon the concentration of at least one acidifying agent in said at least one acidifying coat.

In an aspect, dissolution of said at least one base labile substance and release of said at least one active substance decreases in the presence of increasing concentrations of at least one acidifying agent in said at least one acidifying coat.

In an aspect, the rate of dissolution of said at least one base labile coat is inversely proportional to the number of unit dose formulations ingested.

In an aspect, the rate of dissolution of said at least one base labile substance is inversely proportional to the number of unit dose formulations ingested.

In an aspect, wherein, when the number of unit dosage forms ingested exceeds a predetermined number, said at least one acidifying coat decreases duodenum pH to inhibit dissolution of said at least one base labile coat and inhibit release of said at least one active substance.

In an aspect, wherein, when the number of unit dosage forms ingested exceeds a predetermined number, said at least one acidifying coat decreases duodenum pH to inhibit dissolution of said at least one base labile substance and inhibit release of said at least one active substance.

In an aspect, each of said at least one acidifying coat comprises at least one acidifying agent.

In an aspect, dissolution of said at least one base labile coat and/or substance and release of said at least one active substance in aqueous medium is dependent upon the concentration of said at least one acidifying agent in the aqueous medium.

In an aspect, said at least one acidifying agent is present in said at least one acidifying coat in an amount such that:
when less than a predetermined number of unit dose formulations is ingested, the intestinal pH remains sufficiently basic to dissolve said at least one base labile coat and/or substance and release said at least one active substance; and
when the predetermined number or more of the unit dose formulations is ingested, the intestinal pH is acidified sufficiently to inhibit dissolution of said at least one base labile coat and/or substance and release of said at least one active substance.

In an aspect, the predetermined number is 1, 2, 3, 4, or 5.

In an aspect, the predetermined number is 1 or 2.

In an aspect, said at least one acidifying agent is selected from the group consisting of an inorganic acid, an organic acid, and combinations thereof.

In an aspect, said at least one acidifying agent is selected from the group consisting of hydrochloric acid, sulfuric acid, nitric acid, lactic acid, phosphoric acid, citric acid, malic acid, fumaric acid, stearic acid, tartaric acid, boric acid, borax, benzoic acid, and combinations thereof.

In an aspect, said at least one acidifying agent is fumaric acid and/or citric acid.

In an aspect, each of said at least one base labile coats comprise at least one base labile substance.

In an aspect, said at least one base labile substance is selected from the group consisting of pharmaceutically acceptable ethers, esters, ketones, epoxies, polyamides, polysiloxanes, enteric polymers, anionic copolymers based on methacrylic acid and methyl methacrylate, and combinations thereof.

In an aspect, said at least one base labile coat and/or substance comprises at least one enteric polymer, such as Eudragit L or S.

In an aspect, said at least one base labile coat and/or base labile substance dissolves in a solution with a pH of more than about 6, 7, 8, 9, 10, or 11.

In an aspect, dissolution of said at least one base labile coat is inhibited in a solution with a pH of less than about 6, 5, 4, 3, or 2.

In an aspect, said at least one base labile coat and/or said base labile substance is soluble in duodenum pH.

In an aspect, said at least one acidifying coat has at least one acidifying agent in an amount of at least about 1 mg per unit dosage formulation but such that when more unit dosage formulations than prescribed are swallowed at once, the pH of the duodenum changes to an acidic pH and release of said at least one active substance is inhibited.

In an aspect, the number of unit dosage formulations than that prescribed is about 1 to about 100 and the duodenum pH is greater than about 6, the pH of the stomach changes to acidic pH.

In an aspect, the number of unit dosage formulations than that prescribed is is less than 20 and the duodenum pH is greater than about 7, the pH of the duodenum changes to pH less than about 4 and typically, less than about 6.

In an aspect, said at least one active substance is homogenously mixed within the core, typically, the core comprises at least one disintegrant, at least one Eudragit RL and Eudragit RS, at least one coloring agent, and at least one polyethylene oxide.

In an aspect, the core comprises an outer active substance-releasing layer beneath said at least one base and/or acid labile coat.

In an aspect, the core comprises a plurality of compressed granules.

In an aspect, the unit dose formulation further comprises at least one agent selected from the group consisting of an abuse deterrent coloring agent; a controlled release agent; a vicosity imparting agent; a gelling agent; polyethylene oxide; crospovidone; Eudragit RL; Eudragit RS, and combinations thereof.

In an aspect, the unit dose formulation further comprises at least one abuse deterrent coloring agent.

In an aspect, wherein said at least one abuse deterrent coloring agent is brilliant blue; typically, Aluminum Lake Blue #1.

In an aspect, the unit dose formulation further comprises at least one agent selected from the group consisting of a chewing discouraging agent, a licking discouraging agent, an insufflation discouraging agent, a snorting discouraging agent, an inhalation discouraging agent, and combinations thereof.

In an aspect, the inhalation discouraging agent is selected from the group consisting of a coloring agent, a tussigenic agent, an irritant, and combinations thereof.

In an aspect, the unit dose formulation further comprising said at least one abuse deterrent coloring agent.

In an aspect, wherein said at least one abuse deterrent coloring agent is brilliant blue; typically, Aluminum Lake Blue #1.

In an aspect, said at least one active substance is at least one addictive substance.

In an aspect, said at least one active substance is at least one opioid agonist and/or at least one narcotic analgesic.

In an aspect, said at least one active substance has an analgesic ceiling effect.

In an aspect, the unit dose formulation is in the form of a bead, capsule, tablet, granule, and/or pellet.

In an aspect, said at least one active substance is in an amount of from about 0.1 mg to about 1000 mg; said at least one base labile coat is in an amount of from about 0.5 mg to about 500 mg; and/or said at least one acidifying coat is in an amount of from about 0.5 mg to about 500 mg.

In an aspect, said at least one base labile coat is present in an amount of from 0.5 mg/cm$^2$ to 200 mg/cm$^2$ or from 1 mg/cm$^2$ to 100 mg/cm$^2$ or from 2 mg/cm$^2$ to 150 mg/cm$^2$ or from about 4 mg/cm$^2$ to about 100 mg/cm$^2$ or from about 0.5 to about 50 mg/cm$^2$ or from about 8 to about 50 mg/cm$^2$ or from about 0.5 to about 8 mg/cm$^2$.

In an aspect, said at least one base labile coat and/or base labile substance is present in an amount that yields from about 1% to about 200% weight gain, from about 1% to about 70% or from about 1% to about 50% weight gain.

In an aspect, said at least one acidifying coat has a thickness of from about 2 mg/cm$^2$ to about 100 mg/cm$^2$, or 15 mg/cm$^2$ to about 55 mg/cm$^2$, or 10 mg/cm$^2$ to about 40 mg/cm$^2$, or 40 mg/cm$^2$ to about 80 mg/cm$^2$, or 80 mg/cm$^2$ to about 100 mg/cm$^2$.

In an aspect, said at least one acidifying coat is present in an amount that yields from about 1% to about 200% weight gain, from about 5% to about 80%, from about 1% to about 70% weight gain, from about 1% to about 50% or from about 5% to about 50% weight gain.

In an aspect, said at least one acidifying coat is partially, substantially or completely surrounding.

In an aspect, said at least one base labile coat is substantially or completely surrounding.

In an aspect, the unit dose formulation is an immediate release or controlled release medication.

In an aspect, said at least one active comprises a known/commercial drug formulation.

In an aspect, said at least one active comprises multivitamins, Tylenol, Aspirin, Oxycodone, Hydrocodone, Oxymorphone, Hydromorphone, Morphine, Codeine, or combinations thereof.

In an aspect, an insignificant amount of said at least one active substance or less is released when the number of unit dosage forms ingested exceeds a predetermined number.

In an aspect, wherein when more than the recommended dose is ingested at once, an insignificant amount or less of said at least one active substance is released.

In an aspect, wherein when more than the recommended dose is ingested at once, there is a lag time before a significant amount of said at least one active substance is released.

In an aspect, wherein when between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms are swallowed intact, the formulation delays, reduces or prevents the instantaneous release of all or significant amounts of said at least one active substance.

In an aspect, wherein when greater than 100 unit dose forms are swallowed intact, the formulation delays, reduces or prevents the instantaneous release of all or significant amounts of said at least one active substance.

In an aspect, the pharmacokinetic profile on single dosage administration during fasting and/or feed conditions shows a high rate of input of said at least one active substance in the first hour which is at least 5 times the rate of of input of said at least one active substance at subsequent hourly intervals.

In an aspect, said formulation is about 40 mg oxycodone hydrochloride form wherein the pharmacokinetic profile on single dose administration shows a mean plasma concentration per unit of time of between about 15 ng/ml and about 35 ng/ml between about the first hour and about the sixth hour.

In an aspect, a capsule comprising the unit dose formulation as described herein.

In an aspect, wherein said at least one active substance is an over the counter (OTC) medication.

According to an aspect, there is provided a method of inhibiting or preventing overdose, the method comprising administering the unit dose formulation or the capsule described herein.

According to an aspect, there is provided a method of treating or preventing euphoria and/or addiction, the method comprising administering the unit dose formulation or the capsule described herein.

According to an aspect, there is provided a method of discouraging abuse, the method comprising administering the unit dose formulation or the capsule described herein.

According to an aspect, there is provided a method of delaying euphoria and/or overdose, the method comprising administering the unit dose formulation or the capsule described herein.

According to an aspect, there is provided a method of preventing suicide or accidental death from overdose or euphoria, the method comprising administering the unit dose formulation or the capsule described herein.

According to an aspect, there is provided a method of managing condition(s), disorder(s) and/or disease(s), the method comprising administering the unit dose formulation or the capsule described herein.

According to an aspect, there is provided a method of managing at least one of pain, insomnia, depression, schizophrenia, attention deficit hyperactivity disorder, epilepsy, cardiovascular diseases, diabetes, and neuropathic pain, the method comprising administering the unit dose formulation or the capsule described herein.

In an aspect, said at least one active substance is an over the counter (OTC) medication.

According to an aspect, there is provided a use of the unit dose formulation or the capsule described herein to inhibit or prevent overdose.

According to an aspect, there is provided a use of the unit dose formulation or the capsule described herein to treat or prevent addiction.

According to an aspect, there is provided a use of the unit dose formulation or the capsule described herein to discourage abuse.

According to an aspect, there is provided a use of the unit dose formulation or the capsule described herein to delay overdose or euphoria.

According to an aspect, there is provided a use of the unit dose formulation or the capsule described herein to prevent suicide or accidental death from overdose or euphoria.

According to an aspect, there is provided a use of the unit dose formulation or the capsule described herein for managing condition(s), disorder(s) and/or disease(s).

According to an aspect, there is provided a use of the unit dose formulation or the capsule described herein for managing at least one of pain, insomnia, depression, schizophrenia, attention deficit hyperactivity disorder, epilepsy, cardiovascular diseases, diabetes, and neuropathic pain.

In an aspect, said at least one active substance is an over the counter (OTC) medication.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the present invention will now be described, by way of example only, with reference to the attached Figures.

FIG. 13A is a graph showing the rate and extent of dissolution of 1-6 tablets in the acidic solution. FIG. 13B is a graph showing the rate and extent of dissolution of 10, 20, 40, 60, 80, and 100 tablets in the acidic solution. FIG. 13C is an image of one tablet in the acidic solution. FIG. 13D is 10 an image of two tablets in the acidic solution. FIG. 13E is an image of three tablets in the acidic solution. FIG. 13F is an image of four tablets in the acidic solution. FIG. 13G is an image of five tablets in the acidic solution. FIG. 13H is an image of six tablets in the acidic solution.

FIG. 14C is an image of one tablet in the acidic solution. FIG. 14D is an image of two tablets in the acidic solution. FIG. 14E is an image of three tablets in the acidic solution. FIG. 14F is an image of four tablets in the acidic solution. FIG. 14G is an image of five tablets in the acidic solution. FIG. 14H is an image of six tablets in the acidic solution.

FIG. 15A is a graph showing the rate and extent of dissolution of 1-6 tablets in the acidic solution. FIG. 15B is a graph showing the rate and extent of dissolution of 10, 20, 40, 60, 80, and 100 tablets in the acidic solution. FIG. 15C is an image of one tablet in the acidic solution. FIG. 15D is an image of two tablets in the acidic solution. FIG. 15E is an image of three tablets in the acidic solution. FIG. 15F is an image of four tablets in the acidic solution. FIG. 15G is an image of five tablets in the acidic solution. FIG. 15H is an image of six 35 tablets in the acidic solution. FIG. 15I is an image of 10 tablets in the acidic solution, FIG. 15J is an image of 20 tablets in the acidic solution. FIG. 15K is an image of 50 tablets in the acidic solution.

FIG. 16A is a graph showing the comparison of drug release when 100 tablets from each example was added to the acidic solution. FIG. 16B is of images of 1-6 tablets from each example after a time period of incubation in the acidic solution.

DETAILED DESCRIPTION OF CERTAIN EMBODIMENTS

Definitions

Figure 1:
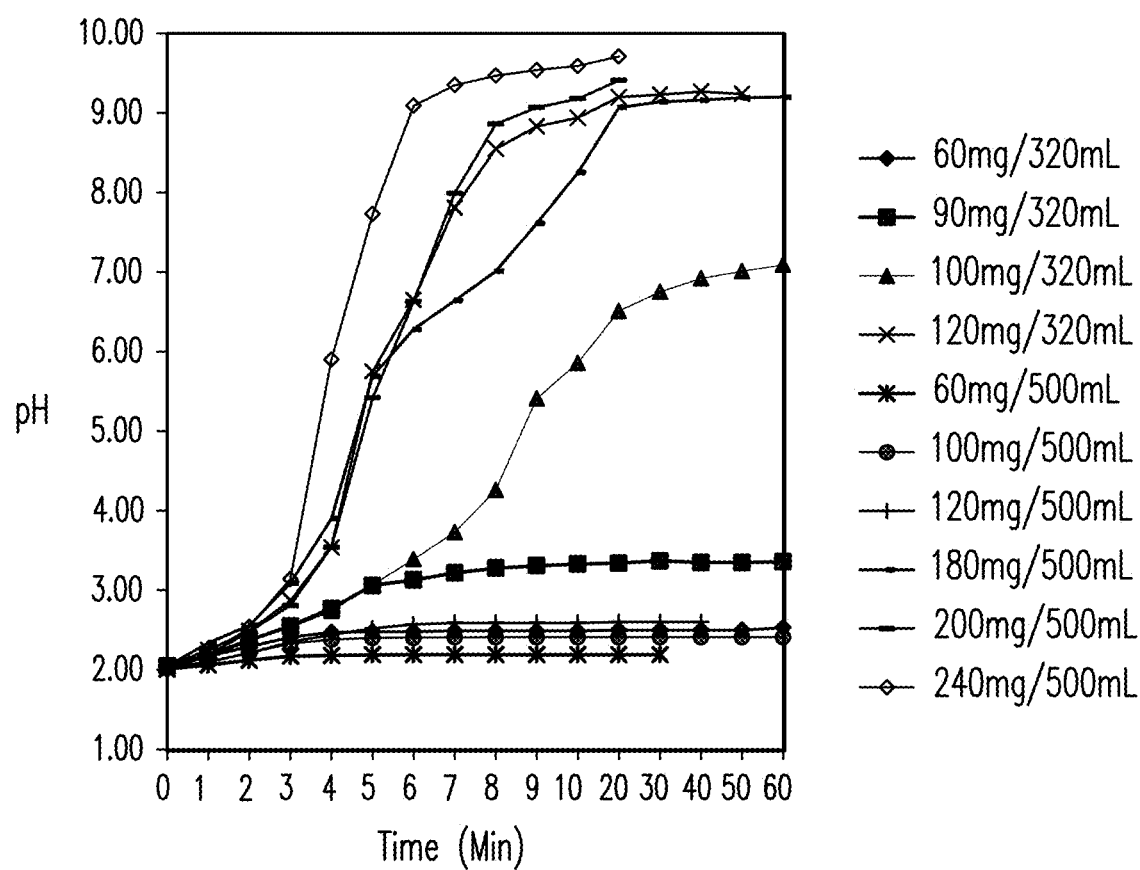
FIG. 1 shows the effects of magnesium hydroxide on the pH of an acidic solution over a 60 minute timecourse in amounts ranging from 60-120 mg/320 ml acidic solution and from 60-240 mg/500 ml acidic solution.

The terms "overdose" or "overdosing" describe the ingestion or application of a drug or other substance in quantities greater than are recommended, prescribed, or generally practiced. An overdose is widely considered harmful and dangerous and may result in toxicity or death. An overdose may be intentional or accidental. This term also therefore encompasses a method of suicide or attempted suicide that involves taking medication in higher than recommended doses or in combinations that will interact to cause harmful effects or increase the potency of another drug. Accidental overdose may occur by failure to read or understand product labels or as a result of over-prescription, failure to recognize a drug's active ingredient, or by unwitting ingestion by children. A common unintentional overdose in children involves ingestion of multi-vitamins containing iron. Unintentional misuse leading to overdose can also include using prescribed or un-prescribed drugs in excessive quantities in an attempt to produce euphoria. Usage of illicit drugs of unexpected purity, in large quantities, or after a period of drug abstinence can also induce overdose. Cocaine users who inject intravenously can easily overdose accidentally, as the margin between a pleasurable drug sensation and an overdose is small.

The terms "formulation" and "composition" may be used interchangeably. A "unit dose formulation" or "unit dose form" is a formulation or composition in a single dose size. Examples include pills, tablets, caplets, capsules, etc.

The term "active ingredient," "active agent," or "active substance" means any compound which has biological, chemical, or physiological utility including, without limitation, active pharmaceutical ingredient, drug, naturally occurring compound, nucleic acid compound, peptide compound, biologics, nutraceutical, agricultural or nutritional ingredient or synthetic drug, including addictive substances such as opioid agonists or narcotic analgesics, hypnotics, tranquilizers, stimulants and antidepressants.

The terms "primary" and "secondary" used in conjunction with "active ingredient" were used to assist simply for antecedent purposes and are not meant to imply the level of importance of the active ingredient.

The term "insufflation" means the practice of blowing or breathing medicated material or powder into the lungs or inhaling or snorting a substance. "Insufflation discouraging agents" include, for example, irritants and tussigenic agents. The term "irritant" includes a compound used to impart an irritating or burning sensation. The term "tussigenic" includes a compound used to cause coughing.

The term "addictive substance" means any compound upon which a user may develop a psychic or physical dependence, including, without limitation, any active ingredient or active substance as defined herein that may have this property.

Many interchangeable terms are commonly used to describe the psychic or physical dependence of people upon compounds. The term addiction is most commonly used when talking about the strong analgesics or opioid agonist or abuse-able substances. The strong analgesics or opioid agonist or abuse-able substances, in contrast to the weaker agents such as aspirin, acetaminophen, and the like, are employed in the relief of more severe pain. They usually produce a euphoric effect when crushed and swallowed, snorted, or when modified for "shooting" parenterally. When taken as prescribed there is usually no significant euphoria.

Addictive substances also include drugs most commonly employed for illicit purposes (to bring about a "high", euphoria, excitement, stupor, sleep deprivation etc.,) such as the barbiturates, lysergic acid diethylamide (LSD), mescaline, marijuana (tetrahydrocannabinol), heroin, and the like, the central nervous system stimulants (the amphetamines and the like) sedative, hypnotics and some of the major and minor tranquilizers (the promazines, meprobamate, the diazepines, and the like).

Examples of some of the opioid agonists or narcotic analgesics contemplated for use in this invention include alfentanil, allylprodine, alphaprodine, anileridine, benzylmorphine, bezitramide, buprenorphine, butorphanol, clonitazene, codeine, desomorphine, dextromoramide, dezocine, diampromide, diamorphine, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tramadol, tilidine, alphaprodine, dextroporpoxyphene, propiram, profadol, phenampromide, thiambutene, pholcodeine, 3-trans-dinnethylamino-4-phenyl-4-trans-carbethoxy-delta-cyclohexene, 3-dimethylamino-O-(4-methoxyphenylcarbamoyl)-propiophenone oxime, (−) β-2'-hydroxy-2,9-dimethyl-5-phenyl-6,7-benzomorphan, (−)2'-hydroxy-2-(3-methyl-2-butenyl)-9-methyl-5-phenyl-6,7-benzomorphan, pirinitramide, (−)α-5,9-diethyl-2'-hydroxy-2-methyl-6,7-benzomorphan, ethyl-1-(2-dimethylaminoethyl)-4,5,6,7-tetrahydro-3-methyl-4-oxo-6-phenylindole-2-carboxylate, 1-benzoylmethyl-2,3-dimethyl-3-(m-hydroxyphenyl)-piperidine, N-allyl-7α-(1-(R)-hydroxy-1-methylbutyl)-6,14-endo-ethanotetrahydron ororipavine, (−)2'-hydroxy-2-methyl-6,7-benzomorphan, noracylmethadol, phenoperidine, α-dl-methadol, β-dl-methadol, α-1-methadol, β-dl-acetylmethadol, α-1-acetylmethadol and β-1-acetylmethadol and pharmaceutically acceptable salts thereof, stereoisomers thereof, ethers thereof, esters thereof, and mixtures thereof and their prodrugs in each case.

Furthermore, in certain embodiments, the formulations described herein may be particular suitable for inhibiting, preventing, or delaying overdose of a pharmaceutical active ingredient selected from the group consisting of opiates, opioids, tranquillizers, typically benzodiazepines, barbiturates, stimulants and other narcotics and their prodrugs in each case. The formulations may be particularly suitable for preventing abuse of an opiate, opioid, tranquillizer or another narcotic selected from the group consisting of N-{1-[2-(4-ethyl-5-oxo-2-tetrazolin-1-yl)ethyl]-4-methoxymethyl-4-piperid-yl}propionanilide (alfentanil), 5,5-diallylbarbituric acid (allobarbital), allylprodine, alphaprodine, 8-chloro-1-methyl-6-phenyl-4H-[1,2,4]triazolo[4,3-a][1,4]-benzodiazepine (alprazolam), 2-diethylamino-propiophenone (amfepramone), (±)-α-methyl-phenethylamine (amphetamine), 2-α-methylphenethylamino)-2-phenylacetonitrile (amphetaminil), 5-ethyl-5-isopentylbarbituric acid (amobarbital), anileridine, apocodeine, 5,5-diethylbarbituric acid (barbital), benzylmorphine, bezitramide, 7-bromo-5-(2-pyridyl)-1H-1,4-benzodiazepine-2(3H)-one (bromazepam), 2-bromo-4-(2-chlorophenyl)-9-methyl-6H-thieno[3,2-f][1,2,4]triazolo-[4,3-a][1,4]diazepine (brotizolam), 17-cyclopropylmethyl-4,5α-epoxy-7a[(S)-1-hydroxy-1,2,2-trimethyl-propyl]-6-methoxy-6,14-endo-ethanomorphinane-3-ol (buprenorphine), 5-butyl-5-ethylbarbituric acid (butobarbital), butorphanol, (7-chloro-1,3-dihydro-1-methyl-2-oxo-5-phenyl-2H-1,4-benzodiazepine-3-yl)-dimethylcarbamate (camazepam), (1S,2S)-2-amino-1-phenyl-1-propanol (cathine/D-norpseudoephedrine), 7-chloro-N-methyl-5-phenyl-3H-1,4-benzodiazepine-2-ylamine-4-oxide (chlorodiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepine-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepine-2(3H)-one (clotiazepam), 10-chloro-11b-(2-chlorophenyl)-2,3,7,11b-tetrahydrooxazolo[3,2-d][1,4]benzodiazepine-6(5H)-one (cloxazolam), (−)-methyl-[3β-benzoyloxy-2-β(1α(H,5-αH)-tropancarboxylate] (cocaine), 4,5-α-epoxy-3-methoxy-17-methyl-7-morphinene-6-α-ol (codeine), 5-(1-cyclohexenyl)-5-ethylbarbituric acid (cyclobarbital), cyclorphan, cyprenorphine, 7-chloro-5-(2-chlorophenyl)-1H-1,4-benzodiazepine-2(3H)-one (delorazepam), desomorphine, dextromoramide, (±)-(1-benzyl-3-dimethylamino-2-methyl-1-phenylpropyl) propionate (dextropropoxyphen), dezocine, diampromide, diamorphine, 7-chloro-1-methyl-5-phenyl-1H-1,4-benzodiazepine-2(3H)-one (diazepam), 4,5-α-epoxy-3-methoxy-17-methyl-6-α-morphinanol (dihydrocodeine), 4,5-α-epoxy-17-methyl-3,6-α-morphinandiol (dihydromorphine), dimenoxadol, dimepheptanol, dimethylthiambutene, dioxaphetyl butyrate, dipipanone, (6aR,10aR)-6,6,9-trimethyl-3-pentyl-6a,7,8,10a-tetrahydro-6H-benzo[c]chromene-1-ol (dronabinol), eptazocine, 8-chloro-6-phenyl-4H-[1,2,4]triazolo[4,3-a][1,4]benzodiazepine (estazolam), ethoheptazine, ethylmethylthiambutene, ethyl [7-chloro-5-(2-fluorophenyl)-2,3-dihydro-2-oxo-1H-1,4-benzodiazepine-3-carboxylate](ethyl loflazepate), 4,5-α-epoxy-3-ethoxy-17-methyl-7-morphinene-6-α-ol (ethylmorphine), etonitazene, 4,5-α-epoxy-7-α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine (fencamfamine), 7-[2-(1-methyl-phenethylamino)ethyl]-theophylline) (fenethylline), 3-(α-methylphenethylamino)propionitrile (fenproporex), N-(1-phenethyl-4-piperidyl) propionanilide (fentanyl), 7-chloro-5-(2-fluorophenyl)-1-methyl-1H-1,4-benzodiazepine-2(3H)-one (fludiazepam), 5-(2-fluorophenyl)-1-methyl-7-nitro-1H-1,4-benzodiazepine-2(3H)-one (flunitrazepam), 7-chloro-1-(2-diethylaminoethyl)-5-(2-fluorophenyl)-1H-1,4-benzodiazepine-2(3H)-one (flurazepam), 7-chloro-5-phenyl-1-(2,2,2-trifluoroethyl)-1H-1,4-benzodiazepine-2(3H)-one (halazepam), 10-bromo-11b-(2-fluorophenyl)-2,3,7,11b-tetrahydro[1,3]oxazolyl[3,2-d][1,-4]benzodiazepine-6(5H)-one (haloxazolam), heroin, 4,5-α-epoxy-3-methoxy-17- methyl-6-morphinanone (hydrocodone), 4,5-α-epoxy-3-hydroxy-17-methyl-6-morphinanone (hydromorphone), hydroxypethidine, isomethadone, hydroxymethyl morphinane, 11-chloro-8,12b-dihydro-2,8-dimethyl-12b-phenyl-4H-[1,3]oxazino[3,2-d][1,4]benzodiazepine-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenylheptan-3-yl acetate (levacetylmethadol (LAAM)), (−)-6-dimethyl-amino-4,4-diphenol-3-heptanone (levomethadone), (−)-17-methyl-3-morphinanol (levorphanol), levophenacylmorphane, lofentanil, 6-(2-chlorophenyl)-2-(4-methyl-1-piperazinylmethylene)-8-nitro-2H-imidazo-[1,2-a][1,4]-benzodiazepine-1(4H)-one (loprazolam), 7-chloro-5-(2-chlorophenyl)-3-hydroxy-1H-1,4-benzodiazepine-2(3H)-one (lorazepam), 7-chloro-5-(2-chlorophenyl)-3-hydroxy-1-methyl-1H-1,4-benzodiazepine-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenethylamine (mefenorex), meperidine, 2-methyl-2-propyltrimethylene dicarbamate (meprobamate), meptazinol, metazocine, methylmorphine, N,α-dimethylphenethylamine (methamphetamine), (±)-6-dimethylamino-4,4-diphenyl-3-heptanone (methadone), 2-methyl-3-o-tolyl-4(3H)-quinazolinone (methaqualone), methyl [2-phenyl-2-(2-piperidyl)acetate](methylphenidate), 5-ethyl-1-methyl-5-phenylbarbituric acid (methylphenobarbital), 3,3-diethyl-5-methyl-2,4-piperidinedione (methypryIon), metopon, 8-chloro-6-(2-fluorophenyl)-1-methyl-4H-imidazo[1,5-a][1,4]benzodiazepine (midazolam), 2-(benzhydrylsulfinyl)-acetamide (modafinil), 4,5-α-epoxy-17-methyl-7-morphinen-3,6-α-diol (morphine), myrophine, (±)-trans-3-(1,1-dimethylheptyl)-7,8,10,10-α-tetrahydro-1-hydroxy-6,6-dimethyl-6H-dibenzo[b,d]pyrane-9 (6-aH)-one (nabilone), nalbuphine, nalorphine, narceine, nicomorphine, 1-methyl-7-nitro-5-phenyl-1H-1,4-benzodiazepine-2(3H)-one (nimetazepam), 7-nitro-5-phenyl-1H-1,4-benzodiazepine-2(3H)-one (nitrazepam), 7-chloro-5-phenyl-1H-1,4-benzodiazepine-2(3H)-one (nordazepam), norlevorphanol, 6-dimethylamino-4,4-diphenyl-3-hexanone (normethadone), normorphine, norpipanone, the exudation of plants belonging to the species *Papaver somniferum* (opium), 7-chloro-3-hydroxy-5-phenyl-1H-1,4-benzodiazepine-2 (3H)-one (oxazepam), (cis-trans)-10-chloro-2,3,7,11b-tetrahydro-2-methyl-11b-phenyloxazolo[3,2-d][1,4]benzodiazepine-6-(5H)-one (oxazolam), 4,5-α-epoxy-14-hydroxy-3-methoxy-17-methyl-6-morphinanone (oxycodone), oxymorphone, plants and parts of plants belonging to the species *Papaver somniferum* (including the subspecies *setigerum*), papaveretum, 2-imino-5-phenyl-4-oxazolidinone (pernoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)-barbituric acid (pentobarbital), ethyl-(1-methyl-4-phenyl-4-piperidine carboxylate) (pethidine), phenadoxone, phenomorphan, phenazocine, phenoperidine, piminodine, pholcodine, 3-methyl-2-phenylmorpholine (phenmetrazine), 5-ethyl-5-phenylbarbituric acid (phenobarbital), a, α-dimethylphenethylamine (phentermine), 7-chloro-5-phenyl-1-(2-propynyl)-1H-1,4-benzodiazepine-2(3H)-one (pinazepam), α-(2-piperidyl)benzhydryl alcohol (pipradrol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepine-2(3H)-one (prazepam), profadol, proheptazine, promedol, properidine, propoxyphene, N-(1-methyl-2-piperidinoethyl)-N-(2-pyridyl)propionamide, methyl {3-[4-methoxycarbonyl-4-(N-phenylpropanamido) piperidino]propanoate} (remifentanil), 5-sec-butyl-5-ethyl-barbituric acid (secbutabarbital), 5-allyl-5-(1-methylbutyl)-barbituric acid (secobarbital), N-{4-methoxymethyl-1-[2-(2-thienyl)ethyl]-4-piperidyl}-propionanilide (sufentanil), 7-chloro-2-hydroxy-methyl-5-phenyl-1H-1,4-benzodiazepin-2(3H)-one (temazepam), 7-chloro-5-(1-cyclohexenyl)-1-methyl-1H-1,4-benzodiazepine-2(3H)-one (tetrazepam), ethyl(2-dimethylamino-1-phenyl-3-cyclohexene-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinylbarbituric acid (vinylbital), (1R*,2R*)-3-(3-dimethylamino-1-ethyl-2-methyl-propyl)-phenol, (1R,2R,4S)-2-(dimethylamino) methyl-4-(p-fluoro-benzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, 3-(2-dimethylaminomethyl-1-hydroxy-cyclohexyl) phenyl 2-(4-isobutoxy-phenyl)-propionate, 3-(2-dimethylaminomethyl-1-hydroxy-cyclohexyl)phenyl 2-(6-methoxy-naphthalen-2-yl)-propionate, 3-(2-dimethylamino-methyl-cyclohex-1-enyl)-phenyl 2-(4-isobutyl-phenyl)-propionate, 3-(2-dimethylaminomethyl-cyclohex-1-enyl)-phenyl 2-(6-methoxy-naphthalen-2-yl)-propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxy-benzoic acid 3-(2-dimethyl-aminomethyl-1-hydroxy-cyclohexyl)-phenyl ester, (RR—SS)-2-hydroxy-4-methyl-benzoic acid 3-(2-dimethylamino-methyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitro-benzoic acid 3-(2-dimethyl-aminomethyl-1-hydroxy-cyclohexylyphenyl ester, (RR—SS)-2',4'-difluoro-3-hydroxy-biphenyl-4-carboxylic acid 3-(2-dimethylaminomethyl-1-hydroxy-cyclohexyl)-phenyl ester and for corresponding stereoisomeric compounds, the corresponding derivatives thereof in each case, in particular esters or ethers, and the physiologically acceptable compounds thereof in each case, in particular the salts and solvates thereof, and their prodrugs in each case. The compounds (1R*,2R*)-3-(3-dimethylamino-1-ethyl-2-methyl-propyl)-phenol, (1R,2R,4S)-2-(dimethylamino) methyl-4-(p-fluorobenzyloxy)-1-(m-methoxyphenyl)cyclohexanol or the stereoisomeric compounds thereof or the physiologically acceptable compounds thereof, in particular the hydrochlorides thereof, the derivatives thereof, such as esters or ethers, and processes for the production thereof are known, for example, from EP-A-693475 or EP-A-780369.

The formulations herein may also contain other active ingredients. These include, amongst others and for example, opioid antagonists (such as naloxone), aspirin, phenacetin, caffeine, acetaminophen, antihistamines, homatropine methylbromide, phenyltoloxamine citrate, barbiturates, or the like, or multiple combinations thereof.

Formulations herein may also comprise narcotic analgesics in combination with non-narcotic analgesics, antitussive preparations which contain narcotic or narcotic-like cough suppressants such as codeine, dihydrocodeinone, pholcodeine, and the like. Other products comprising a narcotic or narcotic-like composition for use as an antispasmodic in the gastro-intestinal tract, such as Camphorated Opium Tincture, U.S.P., Opium Tincture, U.S.P., Opium extract, N.F., and the like may also be included.

Any desired amounts of the active substance may be used in the formulation described herein.

The term "ailment" is understood to be any physical or mental disorder or physical or mental disease; acute or chronic.

The term "maintenance dose" is referred to as the amount of active substance required to keep a desired mean steady-state concentration. For example, it is the amount of active substance administered to maintain a desired level of the substance in the blood.

The term "loading dose" is defined as a dose of active substance, often larger than subsequent doses, administered for the purpose of establishing a therapeutic level of the active substance.

The term "acid labile coat" refers to a coat comprising component(s) that will dissolve or degrade partially or completely, in an acidic environment (e.g. in a solution with an acidic pH). The acidic pH may be, for example, below 7, below 6, below 5, below 4, below 3, below 2, or below 1. Typically, the pH at which the acid labile coat will dissolve is in the normal physiological pH of the stomach, such as from about 1 to about 5, from about 1 to about 4, or from about 2 to about 3. Typically, the acid labile coat dissolves or degrades more slowly or to a very low extent when in a solution with a pH that is considered not acidic. It will be understood that the acid labile coat may be prepared and designed to dissolve or degrade within any desired pH range and to not dissolve substantially within any desired pH range. For example, the acid labile coat may be designed to dissolve at any pH below about 4 but above that level, dissolution is inhibited, reduced or slowed. As the pH increases, the dissolution may slow further and may stop nearly completely.

The acid labile coat typically contains an acid labile substance that is responsible for the dissolution or degradation of the acid labile coat under acidic conditions. For example, any suitable acid labile substance used in the pharmaceutical industry may be used. Examples, without being limited thereto, of an acid labile substance include sulfonamide-based polymers and copolymers, amine functional polymers such as polyvinyl pyridine polymers and copolymers, and polysaccharides such as chitosan that are water-soluble at acidic pHs but water-insoluble at neutral or basic pHs and poly (vinylpyrrolidone-co-dimethylmaleic anhydride) (PVD) that is water-soluble at neutral and acidic pHs but water-insoluble at basic pHs. A typical example includes dimethylaminoethyl methacrylate copolymers and derivatives thereof, such as Eudragit E, Eudragit E interpolyelectrolyte complex, Eudragit E polyamopholyte complex, and Eudragit E interpolyelectrolyte complex with Eudragit L and/or Eudragit S. One of ordinary skill in the art could readily determine other materials that are water-insoluble at certain pHs but water-soluble at other pHs.

The term "base labile coat" refers to a coat comprising component(s) that will dissolve or degrade partially or completely, in a weakly acidic, neutral or basic environment (e.g. in a solution with a basic pH). For example, the basic pH may be considered for the purposes herein to be above 6, above 7, above 8, above 9, above 10, above 11, above 12, or above 13. Typically, the pH at which the base labile coat will dissolve is in the normal physiological pH of the duodenum, such as from about 6 to about 9, from about 6.5 to about 9, or from about 7 to about 9. Typically, the base labile coat dissolves or degrades more slowly or to a very low extent when in a solution with a pH that is considered not basic. It will be understood that the base labile coat may be prepared and designed to dissolve or degrade within any desired pH range and to not dissolve substantially within any desired pH range. For example, the base labile coat may be designed to dissolve at any pH above about 6 but below that level, dissolution is inhibited, reduced or slowed. As the pH decreases, the dissolution may slow further and may stop nearly completely.

The base labile coat typically contains a base labile substance that is responsible for the dissolution or degradation of the base labile coat under basic conditions. For example, any suitable base labile substance used in the pharmaceutical industry may be used. Examples, without being limited thereto, of an base labile substance include any pharmaceutically acceptable ethers, esters, ketones, epoxies, polyamides and polysiloxanes that are water-soluble at neutral and basic pHs but water-insoluble at acidic pHs. Any typical examples include any known enteric coating(s) such as enteric polymers. For example, any anionic copolymers based on methacrylic acid and methyl methacrylate. Examples include Eudragit L or S. One of ordinary skill in the art could readily determine other materials that are water-insoluble at certain pHs but water-soluble at other pHs.

The terms "alkalinizing agent," "alkaline pH adjuster," and "alkaline pH control agent" may be used interchangeably and refer to substances that are capable of modifying, controlling and/or adjusting the pH of the external or interior environment of a dosage form typically by making the environment have or maintain a basic pH or increase the pH. It also refers to basic substances and substances that can convert an acidic environment to a less acidic or basic environment. Typically, these agents, when present in a sufficient amount, are able to raise the pH of the stomach to beyond physiological levels and thereby prevent, reduce, or inhibit dissolution of an acid labile substance described above. Examples of alkalinizing agents include basic salts, for example, alkaline earth metal and/or alkali metal salts such as magnesium hydroxide, magnesium trisilicate magnesium oxide, calcium carbonate, sodium bicarbonate, sodium citrate, sodium carbonate, sodium acetate, magnesium carbonate, etc. Other examples include aluminum salts, such as aluminum oxide/hydroxides, any suitable amino acids or amino acid derivatives such as L-arginine or meglumine. Combinations of the alkalinizing agents may be used, including combinations of the examples listed. However, it will be understood that any agent capable of dissolving and/or degrading and raising the pH of an acidic solution can be used.

The term "alkalinizing coat" refers to a coat comprising alkalinizing agent(s) that will dissolve and/or degrade such that it is capable of modifying, controlling and/or adjusting the pH of the external or interior environment of a dosage form typically by making the environment have or maintain a basic pH or increase the pH.

The terms "acidifying agent," "acid pH adjuster," and "acid pH control agent" may be used interchangeably and refer to substances that are capable of modifying, controlling and/or adjusting the pH of the external or interior environment of a dosage form typically by making the environment have or maintain an acid pH or decrease the pH. It also refers to acidic substances and substances that can convert a basic environment to a less basic or acidic environment. Typically, these agents, when present in a sufficient amount, are able to lower the pH of the duodenum to beyond physiological levels and thereby prevent, reduce, or inhibit dissolution of a base labile substance described above. Examples of acidifying agents include, for example, inorganic and organic acids. Examples include, but are not limited thereto, hydrochloric acid, sulfuric acid, nitric acid, lactic acid, phosphoric acid, citric acid, malic acid, fumaric acid, stearic acid, tartaric acid, boric acid, borax, and benzoic acid. Combinations of the acidifying agents may be used, including combinations of the examples listed. However, it will be understood that any agent capable of dissolving and/or degrading and lowering the pH of a basic solution can be used.

The term "acidifying coat" refers to a coat comprising acidifying agent(s) that will dissolve and/or degrade such that it is capable of modifying, controlling and/or adjusting the pH of the external or interior environment of a dosage form typically by making the environment have or maintain an acidic pH or decrease the pH.

The term "enteric coat" refers to a coat that is stable at the highly acidic pH found in the stomach, but breaks down at a less acidic (relatively more basic) pH. For example, enteric coats will not dissolve in the stomach but they will in the basic pH environment present in the small intestine. Materials used for enteric coatings include polymers such as fatty acids, waxes, shellac, plastics, and plant fibers.

The term "Eudragit E" is referred to as a pH dependent polymer and, more specifically, an acid labile polymer and may include any dimethylaminoethyl methacrylate copolymers. Examples include, but are not limited to, Eudragit E™ and Eudragit E 100™.

The term "Eudragit RL" is referred to as a pH independent polymer and may be any poly(ethyl acrylate-co-methyl methacrylate-co-trimethylammonioethyl methacrylate chloride. Examples include, but are not limited to, Eudragit RL™, Eudragit RL 100™, Eudragit™ RL PO, Eudragit™ RL 30 D, and Eudragit™ RL 12.5.

The terms "Eudragit NE", "Eudragit RS" and "Eudragit NM" are referred to as pH independent polymers and may be any neutral copolymer based on ethyl acrylate and methyl methacrylate. Examples include, but are not limited to, Eudragit™ NE 30 D, Eudragit™ NE 40 D, and Eudragit™ NM 30 D, Eudragit™ RS 100, Eudragit™ RS PO, Eudragit™ RS 30 D, and Eudragit™ RS 12.5.

The terms "Eudragit L" and "Eudragit S" are referred to as enteric polymers and may be any anionic copolymers based on methacrylic acid and methyl methacrylate. Examples include Eudragit™ L 100, Eudragit™ L 12.5, Eudragit™ S 12.5 and Eudragit™ S 100. The ratio of the free carboxyl groups to the ester groups is approx. 1:1 in Eudragit™ L 100 and approx. 1:2 in Eudragit™ S 100.

The terms "low", "small" or "fine" particle size are interchangeable and refer to sizes lower than 1500 microns.

The terms "large", "high" or "big" surface area with respect to surface area of the active ingredients or excipients as a population of particles, powder, crystals, granules etc. are interchangeable and refer to surface areas up to 10000 $m^2/g$ or higher.

The term "coat" may be variously characterized as a coating, layer, membrane, film, shell, capsule, or the like, and may partially, substantially or completely surround or envelope. For example, the "coat" may cover portions of the surface to which it is applied; e.g. as a partial layer, partial coating, partial membrane, partial film, or partial shell; it may, for example, be in the form of half spheres that cover the surface.

If the term "surrounding" is used alone, without any qualifier, it is understood to mean "at least partially surrounding".

The term "controlled release" may be variously characterized by "sustained release", "sustained action", "extended release", "modified release", "pulsed release", "delayed release", "targeted release", "site specific release", and "timed release", which are used interchangeably in this application and are defined for purposes of the present invention as the time of release, the extent of release, the rate of release, the site of release and/or release of an active ingredient from a formulation at such a rate that when a dose of the active ingredient is administered in the sustained release, extended release, pulsed release, timed release, delayed release or controlled-release formulation, concentrations (levels) of the active ingredient are maintained within a desired range but below toxic levels over a selected period of time. In the case of in vivo administration, concentrations (levels) of the active ingredient could be measured in blood or plasma, for example. When administered in vivo the sustained release, extended release, pulsed release, timed release, delayed release or controlled-release formulation allows for a timely onset of action and useful plasma concentration of an active ingredient to be maintained for longer than in the case of immediate-release forms.

The expressions "such as", "for example", and "e.g." means examples, without being limited thereto.

The term "polymeric coating" or "polymeric coat" means any coating, which is formed from materials such as resins, pharmaceutical polymers or from materials formed by polymerization of one or more monomers to form linear or branched or cross-linked macromolecules.

The term "functional coating" as used herein is defined to mean a coating that affects the rate of release in-vitro or in-vivo of the active drug(s).

The term "non-functional coat" is defined to mean a coating that does not substantially affect the rate of release in-vitro or in-vivo of the active drug, but can enhance the chemical, biological, physical stability characteristics, or the physical appearance of the modified release dosage form.

The term "onset time" or "onset of action" represents latency, that is, the time required for the drug to reach minimum effective concentration or the time required for the drug to begin to elicit its action. It may also represent the time for complete release of the drug (e.g. loading dose). A "quick onset of action" represents a short period of time, for example, about 1 hour or less, for the drug to reach minimum effective concentration.

The terms "non-enteric polymer" and "pH independent polymer" are here understood to refer to a polymer which is non-enteric, i.e., which is not more soluble in non-acidic media than in acidic media. The terms "non-enteric polymer" and "pH independent polymer" therefore encompass polymers which are equally soluble in acidic, and neutral or basic media. The terms "non-enteric polymer" and "pH independent polymer" may additionally encompass polymers which are more soluble in acidic media than in neutral or basic media and/or swellable in non-acidic media.

The term "mixture" is understood to include a combination of components, not necessarily mixed per se. The terms "mixture" and "combination" may be used interchangeably.

The term "bittering agent" includes a compound used to impart a bitter taste, bitter flavor, etc.

The term "inhibit" refers to partially, substantially, or completely slowing, hindering, reducing, delaying or preventing. The terms inhibit, reduced, prevented, delayed, and slowed may be used interchangeably.

The term "process variable" is understood to include any physical/chemical variable of a fluid media; for example, and without being limited thereto, at least one physical/chemical property of fluid media such as enzyme concentration, $pK_a$, $pK_b$, fat/triglycerides content, polarity (e.g. ionic strength), pH, density, temperature, solubility ($K_{sp}$), etc.

The term "threshold" or "setpoint" is understood to include at least one predetermined value for the process variable; for example, at least one predetermined value associated with at least one physical/chemical property such as enzyme concentration, $pK_a$, $pK_b$, fat/triglycerides content, dielectric constant/strength, pH number or range, density or range, temperature or range, solubility ($K_{sp}$), etc.

The term "regulator" is understood to include any pharmaceutical acceptable additive that is capable of reacting with fluid media to adjust/regulate a process variable of a fluid media; examples include physical/chemical barrier(s) including pH independent additives such as alkalinizing agents, alkalinizing coats, acidifying agents, and acidifying coats, additive(s) that undergo chemical decomposition/ reaction (e.g. breaks down, dissolves, etc.) in accordance with exposure to a fluid media (e.g. fluids in the digestive tract, such as the stomach and duodenum) in order to adjust/regulate the process variable of the fluid media to reach a threshold or setpoint, polymeric materials, etc.

The term "actuator" is understood to include any pharmaceutically acceptable additive that is capable of reacting with fluid media at a pre-determined threshold or setpoint; examples include physical/chemical barrier(s) including pH dependent additives such as acid labile substances, acid labile coats, base labile substances, and base labile coats, additive(s) that undergo chemical decomposition/reaction (e.g. breaks down, dissolves, etc.) in accordance with exposure to a fluid media (e.g. fluids in the digestive tract, such as the stomach and duodenum), polymeric materials, etc.

The term "physical/chemical barrier" is understood to include any pharmaceutically acceptable additive that is capable of acting as a barrier to selectively release an active substance; examples include acid labile substances, acid labile substances coats, polymeric materials, base labile substances, base labile substances coats, alkalinizing agents, alkalinizing coats, acidifying agents, and acidifying coats.

The term "abuse deterrent coloring agent" refers to any suitable pharmaceutically useful coloring agent that can act to deter drug abuse. Examples include Aluminum Lake dyes; Aluminum Lake Blue #1; FD&C Blue No. 1—Brilliant Blue FCF, E133 (blue shade); FD&C Blue No. 2—Indigotine; E132 (indigo shade); FD&C Green No. 3—Fast Green FCF, E143 (turquoise shade); FD&C Red No. 3—Erythrosine, E127 (pink shade, commonly used in glace cherries); FD&C Red No. 40—Allura Red AC, E129 (red shade); FD&C Yellow No. 5—Tartrazine, E102 (yellow shade); FD&C Yellow No. 6—Sunset Yellow FCF, E110 (orange shade); E100 Curcumin (from turmeric), Yellow-orange; E101 Riboflavin (Vitamin $B_2$), formerly called lactoflavin, Yellow-orange; E101a, Riboflavin-5'-Phosphate, Yellow-orange; E102, Tartrazine (FD&C Yellow 5), Lemon yellow; E103, Alkannin, Red-brown; E104, Quinoline Yellow WS, Dull or greenish yellow; E105, Fast Yellow AB, Yellow; E106, Riboflavin-5-Sodium Phosphate, Yellow; E107, Yellow 2G, Yellow; E110, Sunset Yellow FCF (Orange Yellow S, FD&C Yellow 6), Yellow-orange; E111, Orange GGN, Orange; E120, Cochineal, Carminic acid, Carmine (Natural Red 4), Crimson; E121, Citrus Red 2, Dark red; E122, Carmoisine (azorubine), Red to maroon; E123, Amaranth (FD&C Red 2), Dark red; E124, Ponceau 4R (Cochineal Red A, Brilliant Scarlet 4R), Red; E125, Ponceau SX, Scarlet GN, Red; E126, Ponceau 6R, Red; E127, Erythrosine (FD&C Red 3), Red; E128, Red 2G, Red; E129, Allura Red AC (FD&C Red 40), Red; E130, Indanthrene blue RS, Blue; E131, Patent Blue V, Dark blue; E132, Indigo carmine (indigotine, FD&C Blue 2), Indigo; E133, Brilliant Blue FCF (FD&C Blue 1), Reddish blue; E140, Chlorophylls and Chlorophyllins: (i) Chlorophylls (ii) Chlorophyllins, Green; E141, Copper complexes of chlorophylls and chlorophyllins (i) Copper complexes of chlorophylls (ii) Copper complexes of chlorophyllins, Green; E142, Green S, Green; E143, Fast Green FCF (FD&C Green 3), Sea green; E150a, Plain caramel, Brown; E150b, Caustic sulphite caramel, Brown; E150c, Ammonia caramel, Brown; E150d, Sulphite ammonia caramel, Brown; E151, Black PN, Brilliant Black BN, Black; E152, Carbon black (hydrocarbon), Black; E153, Vegetable carbon, Black; E154, Brown FK (kipper brown), Brown; E155, Brown HT (chocolate brown HT), Brown; E160a, Alpha-carotene, Beta-carotene, Gamma-carotene, Yellow-orange to brown; E160b, Annatto, bixin, norbixin, Orange; E160c, Paprika oleoresin, Capsanthin, capsorubin, Red; E160d, Lycopene, Bright to deep red; E160e, Beta-apo-8'-carotenal (C 30), Orange-red to yellow; E160f, Ethyl ester of beta-apo-8'-carotenic acid (C 30), Orange-red to yellow; E161a, Flavoxanthin, Golden-yellow and brownish; E161b, Lutein, Orange-red to yellow; E161c, Cryptoxanthin, Orange-red; E161d, Rubixanthin, Orange-red; E161e, Violaxanthin, Orange; E161f, Rhodoxanthin, Purple; E161g, Canthaxanthin, Violet; E161h, Zeaxanthin, Orange-red; E161i, Citranaxanthin, Deep violet E161j, Astaxanthin, Red; E162, Beetroot Red, Betanin, Red; E163, Anthocyanins, pH dependent (Red, green and purple ranges); E164, Saffron, Orange-red; E170, Calcium carbonate, Chalk, White; E171, Titanium dioxide, White; E172, Iron oxides and iron hydroxides, Brown; E173, Aluminium, Silver to grey; E174, Silver, Silver; E175, Gold, Gold; E180, Pigment Rubine, Lithol Rubine BK, Red; E181, Tannin, Brown; E182, Orcein, Orchil, Purple.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

The condition, disease or disorder can be, e.g., pain, an age-associated disorder, a geriatric disorder, a disorder having an age-associated susceptibility factor, a neoplastic disorder, a non-neoplastic disorder, a neurological disorder, a cardiovascular disorder, a metabolic disorder, a dermatological disorder, or a dermatological tissue condition. Examples include hypertension, angina, diabetes, HIV AIDS, pain, depression, psychosis, microbial infections, gastro esophageal reflux disease, impotence, cancer, cardiovascular diseases, gastric/stomach ulcers, blood disorders, nausea, epilepsy, Parkinson's disease, obesity, malaria, gout, asthma, erectile dysfunction, impotence, urinary incontinence, irritable bowel syndrome, ulcerative colitis, smoking, arthritis, rhinitis, Alzheimer's disease, attention deficit disorder, cystic fibrosis, anxiety, insomnia, headache, fungal infection, herpes, hyperglycemia, hyperlipidemia, hypotension, high cholesterol, hypothyroidism, infection, inflammation, mania, menopause, multiple sclerosis, osteoporosis, transplant rejection, schizophrenia, neurological disorders. Inflammatory conditions that may or may not cause pain. Such conditions may show one or more of the following symptoms: redness, heat, tenderness and swelling. Examples of such conditions include, but are not limited to, chronic inflammatory diseases, such as rheumatoid arthritis, inflammatory bowel disease, systemic lupus erythematosus, multiple sclerosis, and type I and II diabetes, asthma, and inflammatory diseases of the central nervous system such as multiple sclerosis, abscess, meningitis, encephalitis and vasculitis. Examples of cardiovascular conditions associated with pain and/or inflammation include, but are not limited to, angina, arrhythmia, high blood pressure, stroke, congestive heart failure, atherosclerosis, peripheral artery diseases, high cholesterol levels, and heart attacks. Other disordere/conditions include Neurological or neurodegenerative condition or a mental or behavioral disorder. Examples of neurological conditions associated with pain and/or inflammation include, but are not limited to, Alzheimer's disease, amnesia, Aicardi syndrome, amyotrophic lateral sclerosis (Lou Gehrig's disease), anencephaly, anxiety, aphasia, arachnoiditis, Arnold Chiari malformation, attention deficit syndrome, autism, Batten disease, Bell's Palsy, bipolar syndrome, brachial plexus injury, brain injury, brain tumors, childhood depresses ion, Charcol-Marie tooth disease, depression, dystonia, dyslexia, encephalitis, epilepsy, essential tremor, Guillain-Barre syndrome, hydrocephalus, hyperhidrosis, Krabbes disease, learning disabilities, leukodystrophy, meningitis, Moebius syndrome, multiple sclerosis, muscular dystrophy, Parkinson's disease, peripheral neuropathy, obsessive compulsive disorder, postural orthostatic tachycardia syndrome, progressive supranuclear palsy, prosopagnosia, schizophrenia, shingles, Shy-Drager syndrome, spasmodic torticollis, spina *bifida*, spinal muscular atrophy, stiff man syndrome, synesthesia, syringomyelia, thoracic outlet syndrome, tourette syndrome, toxoplasmosis, and trigeminal neurolagia. Examples of mental and behavioral disorders include, but are not limited to, anxiety disorder, panic disorder, obsessive-compulsive disorder, post-traumatic stress disorder, social phobia (or social anxiety disorder), specific phobias, and generalized anxiety disorder. Any of the above conditions can also be accompanied by or manifested by other conditions such as depression, drug abuse, or alcoholism. Examples of neoplastic growth include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell leukemia, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforme, leukemias, lymphomas, malignant melanomas, epidermoid carcinomas, and other carcinomas and sarcomas.

Oral Drug Delivery Formulations, Uses Thereof and Methods of Making Same

Oral drug delivery formulations, uses thereof and methods of making same are provided in order to reduce the potential for abuse, misuse or improper administration of an addictive substance or any active substance and to prevent, reduce, inhibit, or delay purposeful or accidental overdose of an active substance by ingesting too many pills at once, for example.

In general, and in view of the many examples provided herein, the unit dose formulations may comprise at least one active substance, wherein release of the at least one active substance is inhibited when the number of unit dosage formulations ingested exceeds a predetermined number, such as a prescribed number of unit dosage formulations. Each unit dose formulation comprises at least one active substance, at least one actuator (e.g. a physical/chemical barrier such as a pH dependent coat) and at least one regulator (e.g. a physical/chemical barrier such as a pH independent coat). When the unit dose formulation is exposed to a fluid media having a certain process variable (e.g. pH), and a predetermined threshold or setpoint (e.g. pH number or range) is established for the variable, the regulator is capable of adjusting the variable (e.g. depending on the number of unit dosage formulations provided and the amount of regulator present in the formulation) and control the release of the active substance via the actuator. For example, where it is desired for the active substance to be released in an acidic media, the setpoint would be the desired acidic pH range required for such a release. If there is a predetermined number of unit dosage formulations provided, the regulator would dissolve in the acidic media and the actuator would be actuated by the acidic media and permit the release of the active substance. If the number of unit dosage formulations ingested exceeds the predetermined number, the amount of regulator would dissolve in the acidic media, cause the pH of the media to increase above the setpoint, which would, for example, cause a lag time, delayed release, no release or insignificant release of the active substance. In another example, where it is desired for the active substance to be released in a basic media, the setpoint would be the desired basic pH range required for such a release. If there is a predetermined number of unit dosage formulations provided, the regulator would dissolve in the basic media and the actuator would be actuated by the basic media and permit the release of the active substance. If the number of unit dosage formulations ingested exceeds the predetermined number, the regulator would dissolve in the basic media, cause the pH of the media to decrease below the setpoint, which would, for example, cause a lag time, delayed release, no release or insignificant release of the active substance.

In some embodiments, the formulations contain a core surrounded by at least two coats, referred to as an inner coat and an outer coat. It will be understood that additional coats may exist, between or on either side of the inner and/or outer coat, and these are merely referred to as the inner and outer coat in relation to one another. The active substance may be included in the core and/or coat.

The type of inner and outer coats chosen is dependent on where the active substance is to be released in the body. For example, and without being limited thereto, whether the active substance(s) is released in an acidic environment (e.g. stomach) or a basic or less acidic environment (e.g. duodenum).

In one aspect, if the active substance is to be released in the stomach, the core contains the active substance and the inner coat completely surrounds the core. The inner coat contains an acid labile substance so that the inner coat will only dissolve and allow release of the active substance in an acidic environment. The outer coat surrounds the inner coat and comprises an alkalinizing agent. The alkalinizing agent dissolves in aqueous solution in a pH-independent manner.

When a single unit dosage formulation, for example, is ingested, the alkalinizing agent dissolves but is in an insufficient amount to raise the pH of the stomach enough to prevent dissolution of the coat containing the acid labile substance. In this case, the acid labile coat will dissolve and the active substance will be released. However, when multiple unit dosage forms are ingested simultaneously or within a certain amount of time, for example, within about 1 hour or less, such as within about 45 minutes, 30 minutes, 20 minutes, 10 minutes, or 5 minutes, several alkalinizing coats will dissolve, providing sufficient alkalinizing agent to raise the pH of the stomach enough to prevent or slow dissolution of the acid labile coat. In this case, release of the active substance is prevented, reduced, inhibited and/or slowed. In other aspects of the embodiments described above, the active substance may be additionally or solely in a separate coat and/or in other coats, such as the inner coat, as long as it maintains the physiological effect of preventing, reducing, inhibiting and/or slowing release of the active substance when more than the recommended or prescribed number of unit dosage forms is ingested simultaneously or within a certain amount of time. Typically, the active substance may be in a separate coat surrounding the core (between the core and the inner coat) and/or in the inner coat.

In another aspect, if the active substance is to be released in the duodenum, there are at least three coats surrounding the core: an inner coat, an intermediate coat, and an outer coat. The core contains the active substance and the inner coat completely surrounds the core. The inner coat contains a base labile substance so that the inner coat will only dissolve and allow release of the active substance in a basic environment. The intermediate coat surrounds the inner coat and comprises an acidifying agent. The acidifying agent dissolves in aqueous solution in a pH-independent manner. The outer coat surrounds the intermediate coat and comprises a base labile substance so that the coat will remain substantially intact so that it reaches the duodenum.

When a single unit dosage formulation, for example, is ingested, the outer coat with the base labile substance dissolves in the duodenum to expose the intermediate coat comprising the acidifying agent. The intermediate coat dissolves but is in an insufficient amount to lower the pH of the duodenum enough to prevent dissolution of the inner coat containing the base labile substance. In this case, the inner base labile coat will dissolve and the active substance will be released. However, when multiple unit dosage forms are ingested simultaneously or within a certain amount of time, for example, within about 1 hour or less, such as within about 45 minutes, 30 minutes, 20 minutes, 10 minutes, or 5 minutes, several acidifying coats will dissolve, providing sufficient acidifying agent to lower the pH of the duodenum enough to prevent, reduce or slow dissolution of the inner base labile coat. In this case, release of the active substance is prevented, reduced, inhibited and/or slowed. In other aspects, the active substance may be additionally or solely in a separate coat(s) and/or in other coats, such as the inner coat, as long as it maintains the physiological effect of preventing, reducing, inhibiting and/or slowing release of the active substance when more than the recommended or prescribed number of unit dosage forms is ingested simultaneously or within a certain amount of time. Typically, the active substance may be in a separate coat surrounding the core (between the core and the inner coat) and/or in the inner coat. In general, the formulations provide the necessary amount of a drug to the patient over a period of time in order to accomplish the desired pharmaceutical effect (such as timely and adequate pain relief, inducing sleep, control of blood pressure and blood sugar levels, etc.), while decreasing or eliminating the problem of improper administration of medications and their use in a non-indicated or non-prescribed manner resulting in abuse, drug overdose, addiction, suboptimal efficacy, or death.

The formulations may additionally incorporate one or more insufflation discouraging agents in order to prevent, reduce, or inhibit abuse by crushing and inhaling the unit dose formulation. For example, the formulation when perturbed, pulverized or crushed or ground or milled or cut into one or more sizes ranging from very fine to coarse particles, granules or spheres are inhaled or snorted a moderate to severe discomfort is triggered due to irritation and discomfort in the nostrils and the airways and lungs which leads to dislike and helps to discourage further use or abuse.

In certain embodiments, the formulation comprises a core having at least one active substance, and optionally at least one substance that can act to discourage insufflation of powder or granules or particles obtained upon pulverization or milling of the intact formulation wherein the core is surrounded first by an acid labile coat(s), which is further surrounded by an alkalinizing coat(s) or the core is surrounded first by a base labile coat(s), which is further surrounded by an acidifying coat(s), which is further surrounded by a base labile coat(s).

In other embodiments, the formulation comprises a core having at least one active substance, and optionally at least one substance that can act to discourage insufflation of powder or granules or particles obtained upon pulverization or milling of the intact formulation wherein the core is surrounded first by a drug-releasing coat(s), which is further surrounded by an acid labile coat(s) followed by an alkalinizing coat(s) or the core is surrounded first by a base labile coat(s), which is further surrounded by an acidifying coat(s), which is further surrounded by a base labile coat(s).

In yet other embodiments, the formulation comprises a core having optionally at least one substance that can act to discourage insufflation of powder or granules or particles obtained upon pulverization or milling of the intact formulation wherein the core is surrounded first by a drug-releasing coat(s), which is further surrounded by an acid labile coat(s) followed by an alkalinizing coat(s) or the core is surrounded first by a base labile coat(s), which is further surrounded by an acidifying coat(s), which is further surrounded by a base labile coat(s). In some other embodiments one or more of the coats contain at least one substance that can act to discourage insufflation.

In other aspects of the embodiments described above, the active substance may be additionally or solely in a separate coat(s) and/or in other coats, such as the inner coat, as long as it maintains the physiological effect of preventing, reducing, inhibiting and/or slowing release of the active substance when more than the recommended or prescribed number of unit dosage forms is ingested simultaneously or within a certain amount of time. Typically, the active substance may be in a separate coat surrounding the core (between the core and the inner coat) and/or in the inner coat.

The formulations described herein may prevent, retard, reduce, inhibit, or at least not increase, significantly, the instantaneous release or rate of release of the drug substance from a formulation leading to overdose when many unit dose forms of the product are taken intact and at once contrary to the prescribed instructions. The formulations thus, in some instances can prevent, retard, reduce, inhibit, or provide a delay of overdose and its untoward effects from improper administration of a number of intact unit dose forms intentionally or otherwise, as the drug will not be immediately and rapidly released from the formulation. This is demonstrated in the Examples 2, 4, and 6 below.

Certain formulations described herein are immediate release formulations, while certain other formulations are controlled release formulations and yet other formulations are combination products. The formulations may be presented as tablets, capsules, beads, microcapsules, crystals, granules or a combination.

The acid labile coat contains an acid labile substance(s), such as a Eudragit E polymer, in an amount of from about 0.1 wt % to about 99 wt % of the core or layer/coat, typically, from about 1 wt % to about 60 wt % or from about 5 wt % to about 50 wt %. The acid labile coat may provide a coating coverage surface area, for example, of from 0.5 mg/cm$^2$ to 200 mg/cm$^2$ or from 1 mg/cm$^2$ to 100 mg/cm$^2$ or from 2 mg/cm$^2$ to 150 mg/cm$^2$ or from about 4 mg/cm$^2$ to about 100 mg/cm$^2$ or from 8 mg/cm$^2$ to 50 mg/cm$^2$. The acid labile substance(s) may range from a ratio of 1:1000 to a ratio of 1000:1 of the core or layer/coat wt/wt. The acid labile substance(s) may also be present in the amounts of 0.1 to 500% of the composition by weight. In typical embodiments, the amount of the acid labile substance(s) is present of from about a minimum of 0.5 mg. More typically, from about 0.5 mg to about 500 mg, and any ranges or amounts therebetween, based on the weight of the composition.

The base labile coat contains a base labile substance(s), such as a Eudragit L or S polymer, in an amount of from about 0.1 wt % to about 99 wt % of the core or layer/coat, typically, from about 1 wt % to about 60 wt % or from about 5 wt % to about 50 wt %. The base labile coat may provide a coating coverage surface area of from 0.5 mg/cm$^2$ to 200 mg/cm$^2$ or from 2 mg/cm$^2$ to 150 mg/cm$^2$ or from about 4 mg/cm$^2$ to about 100 mg/cm$^2$. The base labile substance(s) may range from a ratio of 1:1000 to a ratio of 1000:1 of the core or layer/coat wt/wt. The base labile substance(s) may also be present in the amounts of 0.1 to 500% of the composition by weight. In typical embodiments, the amount of the base labile substance(s) is present of from a minimum of 0.5 mg. More typically, from about 0.5 mg to about 500 mg, and any ranges or amounts therebetween, based on the weight of the composition.

In another embodiment, there is provided a unit dose formulation comprising a core comprising at least one active substance in an amount of from about 0.1 mg to about 1000 mg; at least one acid labile coat in an amount of from about 0.5 mg to about 500 mg surrounding the core; and at least one alkalinizing coat in an amount of from about 0.5 mg to about 500 mg surrounding said at least one acid labile coat.

In another embodiment, there is provided a unit dose formulation comprising a core comprising at least one active substance in an amount of from about 0.5 mg to about 1000 mg; at least one coat comprising at least one active substance in an amount of from about 0.5 mg to about 1000 mg; at least one acid labile coat in an amount of from about 0.5 mg to about 500 mg surrounding the core; and at least one alkalinizing coat in an amount of from about 0.5 mg to about 500 mg surrounding said at least one acid labile coat.

In another embodiment, there is provided a unit dose formulation comprising a core comprising at least one active substance and at least one acid labile substance in an amount of from about 0.5 mg to about 500 mg; and at least one alkalinizing coat in an amount of from about 0.5 mg to about 500 mg surrounding the core; at least one controlled release agent.

In other embodiments, the core is a mixture of components; typically, a homogeneous mixture of components. For example, the core may comprise at least one abuse deterrent coloring agent; at least one controlled release agent; at least one vicosity imparting agent; at least one gelling agent; polyethylene oxide; crospovidone; Eudragit RL and/or RS, or mixtures/combinations thereof.

In a specific embodiment, the core comprises at least one active substance and at least one abuse deterrent coloring agent.

In a specific embodiment, the core includes a homogeneous mixture of said at
least
one active substance and at least one controlled release agent.

In a specific embodiment, the core includes a homogeneous mixture of said at least one active substance and at least one vicosity imparting agent.

In a specific embodiment, the core includes a homogeneous mixture of said at least one active substance and at least one gelling agent.

In a specific embodiment, the core includes a homogeneous mixture of said at least one active substance and polyethylene oxide.

In a specific embodiment, the core includes a homogeneous mixture of said at least one active substance and crospovidone.

In a specific embodiment, the core includes a homogeneous mixture of said at least one active substance and Eudragit RL and/or RS.

In a specific embodiment, one or more than one coat includes at least one abuse deterrent coloring agent.

Examples of the amounts of the components are as follows:

In a specific embodiment, the core includes a mixture of said at least one active substance and from about 1 mg to about 400 mg of at least one abuse deterrent coloring agent.

In a specific embodiment, the core includes a homogeneous mixture of said at least one active substance and from about 4 mg to about 600 mg of at least one controlled release agent.

In a specific embodiment, the core includes a homogeneous mixture of said at least one active substance and from about 2 mg to about 700 mg of at least one viscosity imparting agent.

In a specific embodiment, the core includes a homogeneous mixture of said at least one active substance and from about 2 mg to about 1000 mg of at least one gelling agent.

In a specific embodiment, the core includes a homogeneous mixture of said at least one active substance and from about 3 mg to about 1000 mg of polyethylene oxide In a specific embodiment, the core includes a homogeneous mixture of said at least one active substance and from about 0.5 mg to about 100 mg of crospovidone In a specific embodiment, the core includes a homogeneous mixture of said at least one active substance and from about 0.5 mg to about 100 mg of Eudragit RL and/or RS In a specific embodiment, one or more coats includes from about 1 mg to about 400 mg of at least one abuse deterrent coloring agent.

The core may comprise an inner matrix of at least one active substance and an outer matrix of at least one active substance (e.g. an active substance release layer).

Such formulations described herein are capable of mitigating or preventing overdose when the amount of a dosage form (e.g., tablets or capsules) is taken over the prescribed or recommended level (amount) or when someone takes a higher dose than prescribed or recommended.

In some typical embodiments, the formulation may be a pharmaceutical formulation having at least one coat of an acid labile substance(s), such as Eudragit E, over-coated with at least one coat of an alkalinizing agent(s).

Some of the formulations may contain an opioid antagonist such as naltrexone in the core or one or more of the coats. The formulations described herein are capable of preventing or mitigating overdose when a drug product or other substance is ingested or swallowed in quantities greater than are recommended or generally practiced or in the case of unintentional misuse via errors in dosage caused by failure to read or understand product labels, including accidental overdoses as a result of over-prescription, failure to recognize a drug's active ingredient, or unwitting ingestion by children.

As discussed above, the formulations described may also contain substances that can make the formulations more objectionable to insufflation upon being pulverized or crushed or ground or milled or cut into one or more sizes ranging from very fine to coarse particles, granules or spheres. As such the formulations are designed to discourage insufflation of pulverized or crushed or ground or milled or cut into one or more sizes ranging from very fine to coarse particles, granules or spheres.

In an embodiment, the formulation comprises i) at least one active substance, ii) Eudragit E (dimethylaminoethyl methacrylate copolymer and the like), iii) one or more alkalinizing agents and optionally iv) substances such as sodium lauryl sulfate and/or other irritants.

In a specific embodiment, the formulation comprises i) at least one active substance in the core, which is surrounded by ii) at least one coating for controlling the release of the active substance(s), wherein at least one of the coating(s) contains Eudragit E (dimethylaminoethyl methacrylate copolymer) and, surrounded by iii) at least one coating for alkalinizing or adjusting or controlling the pH of either the internal or external or both of the environments of the compositions, wherein at least one of the coating(s) contains one or more alkalinizing agents such as magnesium hydroxide, magnesium trisilicate, magnesium oxide, sodium bicarbonate, magnesium carbonate, sodium hydroxide, aluminium hydroxide, calcium carbonate, and other metal hydroxides and basic oxides and substances that can react alone or together and optionally iv) substances such as sodium lauryl sulfate and/or irritants such as capsaicin oleoresin present in either or all of the core or coats.

In another embodiment, the amount of acid labile substance and alkalinizing agent in the coats makes the formulation/compositions more difficult to be inadvertently or deliberately overdosed when ingested intact or abused when subdivided. In a further embodiment, the formulation comprises at least one primary active substance, at least one acid labile coat, and at least one alkalinizing coat wherein the formulation is free of any active substance external to the coat.

In a further embodiment, the formulation comprises i) at least one active substance in the core, or coat surrounding a core which is surrounded by ii) at least one coating for controlling the release of the active substance(s), wherein at least one of the coating(s) contains Eudragit E (dimethylaminoethyl methacrylate copolymer) and, surrounded by iii) at least one coating for alkalinizing or adjusting or controlling the pH of either the internal or external or both of the environments of the compositions, wherein at least one of the coating(s) contains one or more alkalinizing agents such as magnesium hydroxide, magnesium trisilicate, magnesium oxide, sodium bicarbonate, magnesium carbonate, sodium hydroxide, aluminium hydroxide, calcium carbonate, and other metal hydroxides and basic oxides and substances that can react alone or together and optionally iv) one or a combination of irritants or tussigenic substances such as sodium lauryl sulfate, capsaicin oleoresin, citric acid, tartaric acid or their derivatives present in either or all of the core or coats.

In yet a further embodiment, the formulation comprises i) at least one active substance in the core, or coat surrounding a core which is surrounded by ii) at least one coating for controlling the release of the active substance(s), wherein at least one of the coating(s) contains Eudragit E (dimethylaminoethyl methacrylate copolymer) and, this together with at least one or more alkalinizing agent or adjusting or controlling the pH of for modifying either the internal or external or both of the environments of the compositions, wherein at least one or more of the alkalinizing agents and/or pH adjusters and/or pH control agents is magnesium hydroxide, magnesium trisilicate, magnesium oxide, sodium bicarbonate, magnesium carbonate, sodium hydroxide, aluminium hydroxide, calcium carbonate, and other metal hydroxides and basic oxides and substances that can react alone or together and optionally one or a combination of irritants or tussigenic substances such as sodium lauryl sulfate, capsaicin oleoresin, citric acid, tartaric acid or their derivatives are placed in a housing such as a hard gelatin or hydroxyl propyl methyl cellulose capsule, or sachets or bottles and the like.

In a specific embodiment, the formulation comprises at least one active substance; at least one coat comprising Eudragit E (dimethylaminoethyl methacrylate copolymer); and at least one alkalinizing coat.

In a further embodiment, the formulation comprises at least one active substance; at least one polyethylene oxide; at least one disintegrant; at least one Eudragit RL and Eudragit RS; optionally at least one coloring agent; at least one coat comprising Eudragit E (dimethylaminoethyl methacrylate copolymer); and at least one alkalinizing coat.

In a further embodiment, the formulation comprises at least one active substance; at least one acid labile coat, the solubility of which is dependent on the concentration of at least one alkalinizing agent in at least one alkalinizing coat; and the at least one alkalinizing coat.

In a further embodiment, the formulation comprises at least one active substance; at least one polyethylene oxide; at least one disintegrant; at least one Eudragit RL and Eudragit RS; optionally a coloring agent; at least one acid labile coat, the solubility of which is dependent on the concentration of at least one alkalinizing agent in at least one alkalinizing coat; and the at least one alkalinizing coat.

In a further embodiment, the formulation comprises at least one active substance; at least one acid labile coat, the solubility of which is dependent on the concentration of at least one alkalinizing agent in at least one alkalinizing coat; and the at least one alkalinizing coat.

In another embodiment, the formulation comprises at least one active substance; at least one polyethylene oxide; at least one disintegrant; at least one Eudragit RL and Eudragit RS; optionally a coloring agent; at least one acid labile coat, the solubility of which is dependent on the concentration of at least one alkalinizing agent in at least one alkalinizing coat; and the at least one alkalinizing coat.

In a further embodiment, the formulation comprises at least one active substance; at least polyethylene oxide; at least a disintegrant; at least Eudragit RL or RS; optionally a coloring agent; at least one coat that is soluble in stomach pH, the solubility of which is dependent on the concentration of at least one alkalinizing agent; and at least one coat comprising said at least one alkalinizing agent.

In a further embodiment, the formulation comprises at least one active substance; at least one polyethylene oxide; at least one disintegrant; at least one Eudragit RL and Eudragit RS; optionally a coloring agent; at least one coat that is soluble in stomach pH, the solubility of which is dependent on the concentration of at least one alkalinizing agent in at least one alkalinizing coat; and the at least one alkalinizing coat.

In a further embodiment, the formulation comprises at least one active substance; at least one coat that is soluble in stomach pH, the solubility of which decreases in the presence of increasing concentrations of at least one alkalinizing agent in at least one alkalinizing coat; and the at least one alkalinizing coat.

In a further embodiment, the formulation comprises at least one active substance; at least one polyethylene oxide; at least one disintegrant; at least one Eudragit RL or Eudragit RS; optionally a coloring agent; at least one coat that is soluble in stomach pH, the solubility of which decreases in the presence of increasing concentrations of at least one alkalinizing agent in at least one alkalinizing coat; and the at least one alkalinizing coat.

With respect to the embodiments described above regarding formulae designed for release in the stomach, similar embodiments can be designed for release in the duodenum, whereby the alkalinizing agent is replaced with an acidifying agent and the acid labile coat is replaced with a base labile coat; and a further outer base labile coat is added.

In certain embodiments, when more than one intact unit (such as a tablet or capsule) or quantities greater than are recommended or prescribed of the formulation/composition is ingested at once or in the case of unintentional misuse via errors in dosage caused by failure to read or understand product labels, including accidental overdoses as a result of over-prescription, failure to recognize a drug's active ingredient, or unwitting ingestion by children, there is no instantaneous release of all of the active or insignificant amount (e.g. non-life threatening amount) of the active is released over a given period of time. The formulations/compositions, in the embodiments prevent, reduce, inhibit and/or delay overdose or suicide from occurring when more tablets or capsules of an immediate release or controlled release medication than prescribed are taken at once by mouth.

In other embodiments, the formulation delays, inhibits, or prevents the instantaneous release of all or significant amounts of active substance when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Oxycodone (e.g. from about 1 mg to about 500 mg). The formulation delays, inhibits, or prevents the instantaneous release of all or significant amounts of oxycodone when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Hydrocodone (e.g. from about 1 mg to about 500 mg). The formulation delays, inhibits, or prevents the instantaneous release of all or significant amounts of hydrocodone when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Oxymorphone (e.g. from about 1 mg to about 500 mg). The formulation delays, inhibits, or prevents the instantaneous release of all or significant amounts of Oxymorphone when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Hydromorphone (e.g. from about 1 mg to about 500 mg). The formulation delays, inhibits, or prevents the instantaneous release of all or significant amounts of Hydromorphone when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Codeine (e.g. from about 1 mg to about 500 mg). The formulation delays, inhibits, or prevents the instantaneous release of all or significant amounts of Codeine when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Morphine (e.g. from about 1 mg to about 500 mg). The formulation delays, inhibits, or prevents the instantaneous release of all or significant amounts of Morphine when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Oxycodone (e.g. from about 1 mg to about 500 mg) in combination with Acetaminophen or other NSAIDs (e.g. from about 50 mg to about 900 mg). The formulation delays, inhibits, or prevents the instantaneous release of all or significant amounts of oxycodone and/or Acetaminophen and/or NSAIDs when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Hydrocodone (e.g. from about 1 mg to about 500 mg) in combination with Acetaminophen or other NSAIDs (e.g. from about 50 mg to about 900 mg). The formulation delays, inhibits, or prevents the instantaneous release of all or significant amounts of hydrocodone and/or Acetaminophen and/or NSAIDs when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Oxymorphone (e.g. from about 1 mg to about 500 mg) in combination with Acetaminophen or other NSAIDs (e.g. from about 50 mg to about 900 mg). The formulation delays, inhibits, or prevents the instantaneous release of all or significant amounts of Oxymorphone and/or Acetaminophen and/or NSAIDs when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Hydromorphone (e.g. from about 1 mg to about 500 mg) in combination with Acetaminophen or other NSAIDs (e.g. from about 50 mg to about 900 mg). The formulation delays, inhibits, or prevents the instantaneous release of all or significant amounts of Hydromorphone and/or Acetaminophen and/or NSAIDs when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

In another embodiment, a formulation contains Codeine (e.g. from about 1 mg to about 500 mg) in combination with Acetaminophen or other NSAIDs (e.g. from about 50 mg to about 900 mg). The formulation delays, inhibits, or prevents the instantaneous release of all or significant amounts of Codeine and/or Acetaminophen and/or NSAIDs when greater than 1, 2, 3, 4, 5, 6, 7, 8, 9, or 10 unit dose forms are swallowed intact, such as between 2 to 10 unit dose forms, or between 11 to 20 unit dose forms, or between 21 to 30 unit dose forms, or between 31 to 40 unit dose forms, or between 41 to 50 unit dose forms, or between 51 to 100 unit dose forms, or greater than 100 unit dose forms of a medication are swallowed intact.

Formulations Objectionable to Tampering, Chewing, Sucking, Licking and/or Holding in the Mouth A bittering agent may optionally be present in the formulations to make the compromised formulation objectionable to chewing, sucking, licking and/or holding in the mouth. The pharmaceutically acceptable bittering agents used may be denatonium benzoate, denatonium, saccharide esters such as sucrose octaacetate, naringin, phenylglucopyranose, benzyl glucopyranose, tetramethylglucose and glucose pentaacetate, or quassin. The most typical is sucrose octaacetate. With the inclusion of, for example, from about 0.00001 mg to about 100 mg per tablet or unit dosage form of a bittering agent in a formulation, when the formulation is tampered with, the bittering agent imparts a discomforting quality to the abuser to typically discourage the inhalation or oral administration of the tampered formulation, and typically to prevent the abuse of the formulation.

Suitable bittering compositions may include bittering agents or analogues thereof in a concentration 20 to 1000 ppm, typically 10 to 500 ppm and most typically 5 to 100 ppm in the finished product.

In an embodiment, the formulation comprises a core containing one or more active substance(s) with or without a bittering agent, surrounded by an acid labile coat, which is then surrounded by an alkalinizing coat. In another embodiment, the formulation comprises a core containing one or more active substance(s) with or without a bittering agent, surrounded by a base labile coat, which is then surrounded by an acidifying coat, followed by a further base labile coat. The coats can be applied by spraying or dry coating or encapsulation or by a combination of these methods.

In certain embodiments, the formulation is objectionable to chewing, sucking, licking and/or holding in the mouth for more than about 1 minute; for more than about 5 minutes, or for more than about 10 minutes. In another embodiment, the formulation is objectionable to chewing, sucking, licking and/or holding in the mouth for less than about 10 minutes but greater than about 30 seconds. Moreover, in similar embodiments, the formulation will not permit release or will not release a significant amount of the active ingredient(s) in the pH environment of the mouth.

An irritant or tussigenic agent may be present in the formulations. In embodiments, from about 0.000001 mg to about 300 mg of the irritant or tussigenic agent may be present in the formulations. With the inclusion of an irritant (e.g., capsaicin) in the formulation, when the formulation is tampered with, the capsaicin imparts a burning or discomforting quality to the abuser to typically discourage the inhalation, injection, or oral administration of the tampered formulation, and typically to prevent the abuse of the formulation. Suitable capsaicin compositions include capsaicin (trans 8-methyl-N-vanillyl-6-noneamide) or analogues thereof in a concentration between about 0.00125% and 50% by weight, typically between about 1 and about 7.5% by weight, and most typically, between about 1 and about 5% by weight of the formulation but not more than 50 mg/kg body weight daily intake.

In another embodiment, when the dosage form is chewed or licked it leaves behind an intense disagreeable color on the tongue, lips and mouth, which requires some cleaning effort to remove, signalling abuse and thus acting as a deterrent.

In a further embodiment, when the dosage form is crushed or grinded and snorted, inhaled or insufflated, it leaves behind an intense disagreeable color on the nose, nasal orifice slips and mouth which requires some cleaning effort to remove, signalling abuse and thus acting as a deterrent.

In another embodiment, when the dosage form is crushed or grinded and handled by hand it leaves behind an intense disagreeable color on the palm and fingers which requires some cleaning effort to remove, signalling abuse and thus acting as a deterrent.

In another embodiment, when the dosage form is crushed or grinded and placed in contact with aqueous media it forms a viscous gel with an intense disgusting color impacting negatively on syringability and injectability and thus acting as a deterrent.

pH Shifting and Release Distortion Formulations/Compositions

In embodiments, following the ingestion of a predetermined amount (such as the prescribed or recommended amount per dosage regimen) of an intact unit dose form (such as a tablet or capsule), drug release, onset of action, and effectiveness is triggered in the presence of gastric fluid up to a pH of about 5. In this case, the amount of the alkalinizing agent present in this predetermined amount is not sufficient to alkalinize or raise the pH of the stomach, for example, from 1-2 or less than 4 to a pH between 4 to 13 and the acid labile coating will be permitted to dissolve, allowing complete release of the active substance. However, if more than the predetermined amount of the intact unit dose form is ingested, the combined amount of alkalinizing agent is higher and will be sufficient to increase the pH of the stomach, for example, to greater than pH 4 or sufficiently to prevent dissolution of the acid labile coating. Therefore, the unit dosage form will remain intact or substantially intact in the stomach indefinitely or for a longer period of time than it otherwise would.

The formulation described herein, requires the presence of gastric fluid that is of acidic pH (for example, a pH between 1 to 4 and typically, a pH less than 2.5), to trigger the release of the active substance through dissolution of an acid labile coating. An intact unit dose form on its own contains small amounts of alkalinizing agent(s) (for example, from about 1 mg to about 500 mg depending on the predetermined number of solid dosage units to be ingested as per dosage regimin) and that is insufficient to significantly change the acidic pH of the stomach on ingestion. In an embodiment, the predetermined number is 1, 2, 3, 4, or 5; in another embodiment, the predetermined number is greater than 6 but less than 20; the predetermined number is greater than 20 but less than 100.

These are typically prescribed to be taken intact either once, twice, three times, four times or six times a day. In this acidic environment, the acid labile coat is readily dissolved thus freeing the active containing core to disintegrate and release the active substance. However, many unit dose forms (depending on the number of predetermined unit dosage forms, typically, at least 2 dosage forms) cumulatively contain more than sufficient amounts of alkalinizing agent(s) to alter stomach pH from an acidic pH to a less acidic pH, neutral pH, or basic pH. In other words, to alter the stomach pH to a pH at which the acid labile coat will not substantially dissolve over a given period of time. This pH shift results in a basic or less acidic environment (e.g. a pH of from 4 to 12) in which the acid labile coat is not readily dissolved, leaving the unit dose forms intact. This results in the distortion of drug release whereby even though more unit dose forms are ingested less or no active substance is released, contrary to what would be expected.

In other embodiments, following the ingestion of a predetermined amount (such as the prescribed or recommended amount (e.g., 1, 2, 3, 4, or 5 tablets or greater than 6 but less than 20 prescribed to be taken intact once, twice, three times, four times or six times a day) of an intact unit dose form (such as a tablet or capsule), drug release, onset of action, and effectiveness is triggered in the presence of intestinal fluid above a pH of about 6. In this case, the amount of the acidifying agent present in this predetermined amount is not sufficient to acidify the pH of the duodenum and the base labile coating will be permitted to dissolve, allowing complete release of the active substance. However, if more than the predetermined amount of the intact unit dose form is ingested, the amount of acidifying agent is higher and will be sufficient to decrease the pH of the duodenum sufficiently to prevent dissolution of the base labile coating. Therefore, the unit dosage form will remain intact or substantially intact in the duodenum indefinitely or for a longer period of time than it otherwise would.

The formulation described herein, requires the presence of intestinal fluid that is of basic pH, to trigger the release of the active substance through dissolution of a base labile coating. An intact unit dose form on its own contains small amounts of acidifying agent(s) that is insufficient to significantly change the basic pH of the duodenum on ingestion. In this basic environment the base labile coat is readily dissolved thus freeing the active containing core to disintegrate and release the active substance. However, many unit dose forms cumulatively contain more than sufficient amounts of acidifying agent(s) to alter duodenum pH from a basic pH to a less basic pH, neutral pH, or acidic pH. In other words, to alter the duodenum pH to a pH at which the base labile coat will not substantially dissolve over a given period of time. This pH shift results in an acidic or less basic environment in which the base labile coat is not readily dissolved, leaving the unit dose forms intact. This results in the distortion of drug release whereby even though more unit dose forms are ingested less or no active substance is released, contrary to what would be expected.

The formulations may be directed to a dosage form containing a matrix or non-matrix core incorporating one or more active ingredients, excipients, and release controlling agent(s).

In the various embodiments described throughout the description, the surface area concentration of the acid labile substance, such as Eudragit E and/or its interpolyelectrolyte complex(es), in the acid labile coat is at least about 0.5 mg/cm$^2$, more typically, at least 4 to about 10 mg/cm$^2$, and even more typically, at least about 10 to about 200 mg/cm$^2$. For example, the acid labile substance, such as Eudragit E and/or its interpolyelectrolyte complex(es), may be present in a concentration of from about 5 mg/cm$^2$ to about 100 mg/cm$^2$; typically, about 10 mg/cm$^2$ to about 100 mg/cm$^2$ and even more typically, about 40 mg/cm$^2$ to about 100 mg/cm$^2$. The amount of acid labile substance, such as Eudragit E and/or its interpolyelectrolyte complex(es), in the coat may be from about 0.2 wt % to about 90 wt % of the dosage form, typically, about 1 wt % to about 80 wt %, or more typically, 2 wt % to about 60 wt %. An amount of the acid labile substance, such as Eudragit E and/or its interpolyelectrolyte complex(es), in the coat may be from about 1 mg to about 500 mg In the various embodiments described throughout the description, the alkalinizing agent(s) may also be present in the amounts of 0.1 wt % to about 500 wt % of the composition by weight, typically about 1 wt % to about 100 wt %, more typically 1 wt % to about 50 wt %. The alkalinizing agent(s) may also be present in an amount of from about 1 mg to about 1000 mgThe acid labile substance and the alkalinizing agent are selected and used in an amount or proportion depending on the dosing regimen intended such that drug overdose, especially, the overdose occurring from ingesting multiple solid oral dosage forms, is prevented, inhibited, or delayed.

In the various embodiments described throughout the description, the surface area concentration of the base labile substance, such as Eudragit L or S and their interpolyelectrolyte complex(es), in the base labile coat is at least about 0.5 mg/cm$^2$, more typically, at least 4 to about 10 mg/cm$^2$, and even more typically, at least about 10 to about 200 mg/cm$^2$. For example, the base labile substance, such as Eudragit L or S, may be present in a concentration of from about 5 mg/cm$^2$ to about 100 mg/cm$^2$; typically, about 10 mg/cm$^2$ to about 100 mg/cm$^2$ and even more typically, about 40 mg/cm$^2$ to about 100 mg/cm$^2$. The amount of base labile substance, such as Eudragit L or S, in the coat may be from about 0.2 wt % to about 90 wt % of the dosage form, typically, about 1 wt % to about 80 wt %, or more typically, 2 wt % to about 60 wt %. These may also be present in an amount of from about 1 mg to about 1000 mg. In the various embodiments described throughout the description, the acidifying agent(s) may also be present in the amounts of 0.1 wt % to about 500 wt % of the composition by weight, typically about 1 wt % to about 100 wt %, more typically 1 wt % to about 50 wt %. These may also be present in an amount of from about 1 mg to about 1000 mg.

The base labile substance and the acidifying agent are selected and used in an amount or proportion depending on the dosing regimen intended such that drug overdose, especially, the overdose occurring from ingesting multiple solid oral dosage forms, is prevented, inhibited, or delayed. These may also be present in an amount of from about 1 mg to about 1000 mg.

It will be understood that any pharmaceutically acceptable acid labile substance, base labile substance, acidifying agent or alkalinizing agent may be used in these formulations to achieve the pH shifting and drug release distortion phenomenon described.

Formulations Objectionable to Insufflation, Inhaling, Snorting of Milled or Vaporized Powders.

A tussigenic agent may optionally be present in the formulations to make the compromised formulation objectionable to insufflation, inhalation, or snorting when pulverized, milled, crushed or vapourized. The tussigenic agent that may be used includes, for example, citric acid, tartaric acid, zinc sulfate, capsaicin, sodium lauryl sulfate, and the like. With the inclusion of a tussigenic agent in a formulation, when the formulation is tampered with, the tussigenic agent imparts a discomforting quality to the abuser to typically discourage the insufflation, inhalation, or snorting of the tampered formulation, and typically to prevent abuse of the formulation.

In the various embodiments described throughout the description, the tussigenic substances may be present in the amounts of 0.0001 wt % to about 100 wt % of the coat/core by weight, typically about 0.0001 wt % to about 80 wt %, more typically 0.0001 wt % to about 50 wt %. These may also be present in an amount of from about 0.0001 mg to about 1000 mg.

An irritant or substance that discourages insufflation may be present in the formulation. With the inclusion of an irritant (e.g., tobacco, citric acid, quassin, capsaicin and/or sodium lauryl sulfate and/or zinc sulfate) in the formulation, when the formulation is tampered with (i.e., pulverized, crushed or milled), the irritant imparts a burning or discomforting quality to the abuser to typically discourage the inhalation or snorting of the tampered formulation, and typically to prevent the abuse of the formulation. Suitable capsaicin compositions include capsaicin (trans 8-methyl-N-vanillyl-6-noneamide) or analogues thereof in a concentration between about 0.00125% and 50% by weight, typically between about 1 and about 7.5% by weight, and most typically, between about 1 and about 5% by weight of the formulation but not more than 50 mg/kg body weight daily intake. Sodium lauryl sulfate may be present in amounts from 0.1% to 200% by weight of the compositions. These may also be present in an amount of from about 0.0001 mg to about 1000 mg.

The tussigenic and irritant agents may be used alone or in combination.

The formulation may have one or more of an immediate release, modified release, delayed release, controlled release or extended release drug core. The active substance may be any pharmaceutical material that have therapeutic activity, e.g., without limitation, an opioid agonist, a narcotic analgesic, barbiturates, central nervous system stimulants, tranquilizers, antihypertensive, antidiabetics, and/or antiepileptics.

The formulation can be a solid unit formulation such as, and without being limited thereto, a tablet, granules, spheres, particles, beads, capsules or microcapsules.

It will be understood that the formulations may not be limited to addictive substances, and may also be useful in formulations of any active ingredient or substance and, indeed, conventional formulations may be coated with an acid labile coat and an alkalinizing coat and be within the scope described herein.

Administration

The formulation may be administered in-vivo orally, vaginally, anally, ocularly, subcutaneously, intramuscularly, or by implantation. The formulation may also be used for in vitro or ex vivo delivery of an active substance. It may be targeted at specific sites in the gastrointestinal tract or to specific organs. It may be applied occularly and transdermally in a pouch or patch. It is evident that the physical state of the formulation and the particular method of application may vary accordingly. Typically, the formulation is administered orally.

The formulation may reduce the potential for improper administration or use of drugs but which, when administered as directed, is capable of delivering a therapeutically effective dose. In particular, the formulation addresses the need for a drug product, which, compared to conventional formulations, decreases the intensity, quality, frequency and rate of occurrence of the "euphoria" and other untoward effect, which can occur with improper administration.

In yet another embodiment, the formulation, reduces the potential for improper administration or use of drugs but which, when administered as directed, is capable of delivering in a timely fashion, a therapeutically effective dose. In particular, the formulation addresses the need for a drug product, which, compared to conventional formulations, decreases the risk of overdose, inhibits, prevents or delays overdose, reduces the potential for abuse, or decreases the risk of addiction.

In embodiments, the formulation may have a pharmacokinetic profile on single dosage administration during fasting and/or feed conditions that shows a high rate of drug input in the first hour which is at least 5 times the rate of drug input at subsequent hourly intervals.

In another embodiment, the formulation is a 40 mg oxycodone hydrochloride tablet wherein the pharmacokinetic profile on single dose administration shows a mean plasma concentration per unit of time of between about 15 ng/ml and about 35 ng/ml between about the first hour and about the sixth hour.

Various Formulations

In one embodiment, the formulation comprises: one or more of a modified release, delayed release, controlled release and/or extended release core containing an active substance; surrounded first by one or more layers of an acid labile coat; followed by one or more layers of an alkalinizing coat.

In certain embodiments, the formulation may include a dose of an active substance within the core and a further dose of the same or a different active substance outside of the core to provide a loading dose. The loading dose may be incorporated within the acid labile or alkalinizing coat or it may exist in its own coating layer external to the alkalinizing coat, internal to the acid labile coat, or in between the alkalinizing coat and the acid labile coat.

In another embodiment, the formulation comprises: one or more of a modified release, delayed release, controlled release and/or extended release core containing an active substance; surrounded first by one or more layers of a base labile coat; followed by one or more layers of an acidifying coat, and further followed by one or more layers of a base labile coat.

In certain embodiments, the formulation may include a dose of an active substance within the core and a further dose of the same or a different active substance outside of the core to provide a loading dose. The loading dose may be incorporated within one or more of the base labile or acidifying coat or it may exist in its own coating layer external to the acidifying coat, internal to the base labile coat, or in between the acidifying coat and the base labile coat.

The formulation may contain one or more different active substances.

In the various formulations, the active substance is released in one or more time intervals.

The formulation may comprise one or more active substance(s) in a pharmaceutically effective amount, wherein the formulation has is configured such that when the formulation is administered in unit dosage forms, the rate and/or amount of active substance(s) released from the composition is inversely proportional to the number of unit dosage forms administered. For example, administration of 2 or more, 3 or more, 4 or more, 5 or more, 6 or more, 7 or more, 8 or more, 9 or more, or 10 or more unit dosage forms will inhibit, delay, or prevent release of the active substance as compared to administration of a single unit dosage form or a number that is lower than that which was actually intended to be administered under normal circumstances. The delay of release of the active substance may be by a time period selected from the group consisting of about 0.5 hours, about 1 hour, about 2 hours, about 3 hours, about 4 hours, about 5 hours, about 6 hours, about 7 hours, about 8 hours, about 9 hours, or about 10 hours. The inhibition of release of the active substance may be by an amount of about 10% or more, 20% or more, 30% or more, 40% or more, 50% or more, 60% or more, 70% or more, 80% or more, 90% or more, 95% or more, or 99% or more. Thus, if a patient were prescribed one unit dosage form and ingested, for example, 3 or 4 or more either on purpose or accidentally, release of the active substance would be inhibited, delayed, or prevented. In this way, more time is available for the patient to seek medical intervention in order to avoid or mitigate the effects of an overdose. In typical embodiments, the amount of active substance(s) in the formulation is from about 0.1 mg to about 1000 mg, and any ranges or amounts therebetween.

The formulation may comprise one or more active substance(s) (e.g. from about 1 mg to about 1000 mg of Oxycodone, Hydrocodone, Oxymorphone, Hydromorphone, Morphine, Codeine or combinations of these with from about 1 mg to about 1000 mg of NSAIDs such as Acetaminophen, Ibuprofin, Aspirin, Naproxen sodium or Meloxicam) in a pharmaceutically effective amount, wherein the formulation has a acid labile coat and a alkalinizing coat and optionally acidifying coat and is configured such that when the formulation is administered in unit dosage forms, the rate and/or amount of active substance(s) released from the composition is inversely proportional to the number of unit dosage forms administered. For example, administration of 2 or more, 3 or more, 4 or more, 5 or more, 6 or more, 7 or more, 8 or more, 9 or more, or 10 or more unit dosage forms intact and at once will lead to change in stomach pH from acid (of pH1 to pH 3) to less acidic to basic (of between pH 4 to pH 12). This change in pH will inhibit, delay, or prevent release of the active substance as compared to administration of a single unit dosage form or a number that is lower than that which was actually intended to be administered under normal circumstances. The delay of release of the active substance may be by a time period selected from the group consisting of about 0.5 hours, about 1 hour, about 2 hours, about 3 hours, about 4 hours, about 5 hours, about 6 hours, about 7 hours, about 8 hours, about 9 hours, or about 10 hours. The inhibition of release of the active substance may be by an amount of about 10% or more, 20% or more, 30% or more, 40% or more, 50% or more, 60% or more, 70% or more, 80% or more, 90% or more, 95% or more, or 99% or more in a 24 hour period. Thus, if a patient were prescribed one unit dosage form and ingested, for example, 3 or 4 or more either on purpose or accidentally, release of the active substance would be inhibited, delayed, or prevented. In this way, more time is available for the patient to seek medical intervention in order to avoid or mitigate the effects of an overdose.

The formulation may comprise one or more active substance(s) (e.g.from about 1 mg to about 1000 mg of Oxycodone, Hydrocodone, Oxymorphone, Hydromorphone, Morphine, Codeine or combinations of these with from about 1 mg to about 1000 mg of NSAIDs such as Acetaminophen, Ibuprofin, Aspirin, Naproxen sodium or Meloxicam) in a pharmaceutically effective amount, wherein when the formulation is administered in a higher than prescribed dose to a subject, the rate of active substance(s) released from the composition, within a time period selected from the group consisting of about 0.5 hours, about 1 hour, about 2 hours, about 3 hours, about 4 hours, about 5 hours, about 6 hours, about 7 hours, about 8 hours, about 9 hours, or about 10 hours, is substantially the same or lower, typically less than 20%, more typically less than 30%, and most typically less than 40%, than the amount of active substance(s) released when the pharmaceutical composition is administered in the prescribed dose.

The formulation may comprise one or more active substance(s) (e.g.from about 1 mg to about 1000 mg of Oxycodone, Hydrocodone, Oxymorphone, Hydromorphone, Morphine, Codeine or combinations of these with from about 1 mg to about 1000 mg of NSAIDs such as Acetaminophen, Ibuprofin, Aspirin, Naproxen sodium or Meloxicam) in a pharmaceutically effective amount, wherein the formulation is configured such that when the formulation is administered in a prescribed dose, at least 50% of the amount of active substance(s) is released after about 8 hours and when the formulation is administered in a higher than prescribed dose at most about 55%, typically at most about 50%, more typically at most about 30%, of the amount of active substance(s) is released in about 1 hour.

The formulation may comprise one or more active substance(s) (e.g. from about 1 mg to about 1000 mg of Oxycodone, Hydrocodone, Oxymorphone, Hydromorphone, Morphine, Codeine or combinations of these with from about 1 mg to about 1000 mg of NSAIDs such as Acetaminophen, Ibuprofin, Aspirin, Naproxen sodium or Meloxicam in a pharmaceutically effective amount, wherein the formulation is configured such that when the formulation is administered in a prescribed dose, at least 80% of the amount of active substance(s) is released after about 1 hour and when the formulation is administered in a higher than prescribed dose at most about 70% of the amount of active substance(s) is released in about 1 hour.

In yet another embodiment, the formulation is designed such that in the treatment of severe to moderate pain using opioid analgesics (e.g. from about 1 mg to about 1000 mg of Oxycodone, Hydrocodone, Oxymorphone, Hydromorphone, Morphine, Codeine or combinations of these with about 1 mg to about 1000 mg of NSAIDs such as Acetaminophen, Ibuprofin, Aspirin, Naproxen sodium or Meloxicam) timely delivery of onset of pain relief and adequate pain relief is experienced by the patient from about 30, about 60, about 120, about 180 or about 240 minutes. In another embodiment, the formulation is designed such that the formulation or composition can be administered every 8 hours to 12 hours to every 24 hours.

In certain formulations, the active substance(s) and/or inactive substance(s) used in the formulation have a fine, small or low particle size and large, high or big surface area. Accordingly, the particle size is less than 1500 microns, typically less than 1000 microns and more typically less than 400 microns.

In certain formulations, a loading dose is applied as a coat around the core or around the acid labile coat, the base labile coat, the acidifying coat or the alkalinizing coat of the formulation or composition.

In certain formulations, such as from about 1 mg to about 1000 mg of Oxycodone, Hydrocodone, Oxymorphone, Hydromorphone, Morphine, Codeine or combinations of these with about 1 mg to about 1000 mg of NSAIDs such as Acetaminophen, Ibuprofin, Aspirin, Naproxen sodium or Meloxicam, a loading dose is applied as a coat around the core or around the acid labile coat, the base labile coat, the acidifying coat or the alkalinizing coat of the formulation or composition.

The formulation may have one or more of an immediate release, modified release, delayed release, controlled release or extended release drug core; optionally surrounded first by one or more layers of drug embedded in a non-functional coat followed by an acid labile coat then an alkalinizing coat or a base labile coat then an acidifying coat, and further another base labile coat. The active substance may be, without limitation, an opioid agonist, a narcotic analgesic, a barbiturate, a central nervous system stimulant, a tranquilizer, an antihypertensive, an antidiabetic, and/or an antiepileptic. Prior to incorporation within the core or coat, the active substance may be in any suitable form known in the art, such as liquid, semi-solid, solid, paste, or gel, and may be homogenously or non-homogenously dispersed in the core.

The formulation can be a solid unit formulation such as, and without being limited thereto, a tablet, granules, spheres, particles, beads, capsules, or microcapsules.

It will be understood that the formulations may not be limited to addictive substances, and may also be useful in formulations of any active ingredient or substance. Additionally, any known conventional unit dosage form may be coated with an acid labile coat and an alkalinizing coat in order to prevent, reduce, inhibit, and/or slow the onset of an overdose. Likewise, any known conventional unit dosage form may be coated with a base labile coat, then an acidifying coat, followed by another base labile coat, in order to prevent, reduce, inhibit, and/or slow the onset of an overdose. It will be understood that if the conventional unit dosage form is, for example, an enteric coated dosage form then an acidifying coat followed by a base labile coat is sufficient.

Several Embodiments of the Formulations are Provided:

Formulations herein may also comprise at least one active substance that has an analgesic ceiling effect and/or no ceiling effect.

In an embodiment, there is provided a formulation that is effectively employed to control the release of one or more active substances or prevent the instantaneous release of the entire dose in the formulation when a dose above a threshold dose (e.g., a prescribed dose) is ingested.

The formulation may have a modified release, delayed release, controlled release or extended release formulation and in which the physicochemical nature of the formulation is used to reduce the potential and consequences (drug overdose, addiction, suboptimal efficacy, and/or death) of improper administration of medications and their use in a non-indicated or non-prescribed manner.

An immediate release, delayed release, modified release, extended release, pulsed release, sustained release or controlled release profile provided by the formulations disclosed herein may advantageously be used in the formulation of any active ingredient.

A formulation may comprise a core with one or more of a release retarding agent, a controlled release agent, a gelling agent, a polymeric agent, and one or more fillers in a pharmaceutically suitable vehicle, and optionally materials selected from disintegrants, compression aids, lubricants, humectants, surfactants, emulsifiers, plasticizers, antioxidants, and stabilizers.

A formulation may be formulated such that its physicochemical properties discourage drug abuse by ingesting multiple unit dosage forms in amounts that would be generally higher than prescribed or would generally be considered harmful or potentially harmful. The formulation may also be formulated such that its physicochemical properties discourage abuse by modes of crushing, milling or grinding the formulation to powder or heating the formulation to vapor and snorting or inhalation by the nasal route or dissolving to abuse via the parenteral route.

A formulation may comprise a core surrounded by an acid labile coat, an alkalinizing coat, and a polymeric coat, a plastic coat or elastic coat and the like. Alternatively, a formulation may comprise a core surrounded by a base labile coat, an acidifying coat, a further base labile coat, and a polymeric coat, a plastic coat or elastic coat and the like.

Where a formulation of the present invention comprises more than one coat, a first coat substantially surrounds or envelops a core, a second coat substantially surrounds or envelopes the first coat, and so forth. Typically, an acid labile coat is closer to the core than an alkalinizing coat, as the acid labile coat protects the core from disintegrating in non-acidic environments. Likewise, typically, at least one of the base labile coats is closer to the core than an acidifying coat, as the base labile coat protects the core from disintegrating in non-basic environments.

Coats may take the form and composition of any known compatible controlled-release coat, for example a pH sensitive coat, ion-exchange resin coat (containing, for example, cholestyramine, colestipol, sodium polystyrene sulfonate, polacrilex resin, or polacrilin potassium), intestinal bacteria flora or enzyme reactive polymer (such as a polysaccharide-based coat), a water repellant coat, an aqueous solvent-based coat, or a water-soluble coat. The formulations may have an overcoat. Typically, such coats comprise at least one or more polymer composition such as, but not limited to, Opadry and the like. Alternatively, Opadry or the like may be included in the alkalinizing coat as desired.

In embodiments, the acid labile coat or base labile coat thickness is below 1000 mg/cm$^2$, typically below 200 mg/cm$^2$ and more typically below 100 mg/cm$^2$. In aspects, the acid labile coat thickness is from about 1 mg/cm$^2$ to about 100 mg/cm$^2$, such as from about 10 mg/cm$^2$ to about 100 mg/cm$^2$, from about 8 to about 50 mg/cm$^2$, from about 8 to about 12 mg/cm$^2$, about 15 to about 20 mg/cm$^2$, about 19 to about 25 mg/cm$^2$, about 25 to about 35 mg/cm$^2$, about 30 to about 40 mg/cm$^2$, or about 40 to about 50 mg/cm$^2$. In an aspect, said at least one base labile coat is present in an amount of from about 0.5 to about 50 mg/cm$^2$ or from about 8 to about 50 mg/cm$^2$ or from about 0.5 to about 8 mg/cm$^2$.

The alkalinizing coat or acidifying coat typically has a thickness of from about 2 mg/cm$^2$ to about 100 mg/cm$^2$, or 15 mg/cm$^2$ to about 55 mg/cm$^2$, or 10 mg/cm$^2$ to about 40 mg/cm$^2$, or 40 mg/cm$^2$ to about 80 mg/cm$^2$, or 80 mg/cm$^2$ to about 100 mg/cm$^2$.

In embodiments, the coating is applied to cause about 1% to about 200% weight gain, about 2.5% to about 150% weight gain, such as from about 2.5% to about 100%, or from about 3% to about 80% weight gain.

In aspects, the alkalinizing coat is applied to cause from about 1% to about 200% weight gain, such as from about 5% to about 80%, from about 1% to about 70% weight gain, from about 1% to about 50% or from about 5% to about 50% weight gain.

In aspects, the base labile coat is applied to cause from about 1% to about 200% weight gain, such as from about 1% to about 70% or from about 1% to about 50% weight gain.

In aspects, the acidifying coat is applied to cause from about 1% to about 200% weight gain, such as from about 1% to about 70% or from about 1% to about 50% weight gain.

In aspects, the acid labile coat is applied to cause from about 1% to about 200% weight gain, such as from about 1% to about 70% or from about 1% to about 50% weight gain.

In embodiments, the alkalinizing coat is present in an amount sufficient to raise the pH of the stomach, such that dissolution of at least one acid labile coat and release of the active substance is inhibited when the number of unit dosage forms ingested exceeds a predetermined number. In a specific embodiment, the alkalinizing coat comprises at least about 1 mg alkalinizing agent(s) in the unit dosage form/formulation but present in an amount sufficient to raise the pH of an acid media or the stomach to greater than about pH 2, such that dissolution of the acid labile coat and release of the active substance is inhibited when the number of unit dosage forms ingested (or is present in an acid media) exceeds a predetermined number.

The alkalinizing coat may have at least one alkalinizing agent in an amount of at least about 1 mg per unit dosage form but such that when more tablets or dosage forms than prescribed are swallowed at once the pH of the stomach changes to alkaline. In an embodiment, the alkalinizing coat has at least one alkalinizing agent in an amount of at least about 1 mg per tablet or unit dosage form but such that when about 1 to about 100 dosage forms are present at once in an acid media of pH less than about 5, the pH changes to alkaline. In another embodiment, the alkalinizing coat has at least one alkalinizing agent in an amount of at least about 1 mg per tablet or unit dosage form but such that when up to 100 dosage forms, or up to 20 dosage forms, or more than 1, 2, 3, 4, 5, or 6 of dosage forms are present at once in an acid media of pH less than about 4, the pH changes to pH greater than about 4 and typically, greater than about 6.

In embodiments, the acidifying coat is present in an amount sufficient to lower the pH of the duodenum such that dissolution of the at least one base labile substance and release of the at least one active substance is inhibited when the number of unit dosage forms ingested exceeds a predetermined number. In a specific embodiment, the acidifying coat comprises at least about 1 mg acidifying agent(s) in the unit dosage form/formulation but present in an amount sufficient to lower the pH of a basic media or the duodenum to less than about pH of 4, and typically, to a pH less than 2, such that dissolution of the base labile coat and release of the active substance is inhibited when the number of unit dosage forms ingested (or is present in an acid media) exceeds a predetermined number.

In embodiments, the base labile coat comprises at least about 1 mg of base labile substance per tablet or unit dosage form. In embodiments, the acid labile coat comprises at least about 1 mg of acid labile substance per tablet or unit dosage form.

The formulations described herein may release up to about 55% of the total dose as a loading dose to manage pain. In certain embodiments, up to about 55% of the total dose is released as a loading dose within about 60 minutes of ingestion.

For formulations targeted for pain management, such as those selected from the group comprising from about 1 mg to about 1000 mg of Oxycodone, Hydrocodone, Oxymorphone, Hydromorphone, Morphine, Codeine or combinations of these with from about 1 mg to about 1000 mg of NSAIDs such as Acetaminophen, Ibuprofin, Aspirin, Naproxen sodium or Meloxicam, the total dose released as a loading dose within about 60 minutes to about 120 minutes of ingestion, may be from about 1 mg to about 1000 mg of the active pharmaceutical ingredient(s).

The release profile of the formulation depending upon the number of unit dosage forms ingested may be modified on the basis of many factors pertaining to the formulation, particle size and surface area of the active pharmaceutical ingredient and polymers used, design of the physical geometry of the formulation polymeric coats, for example, without limitation, through the choice of particle size and surface area, types of polymers, acid or base labile coats, and alkalinizing or acidifying agents used, the presence or absence of a loading dose, the order in which they are deposited, the ratios of the loading dose to maintenance dose, the ratios of the polymers in the mix and the nature of their interaction. The controlled-release profile can also be modified by a variety of factors relating to the delivery formulation and the route of administration. For example, the sustained-release period and profile will vary depending upon the alkalinizing or acidifying agent concentration, solubility of the acid or base labile coating and the active ingredient, the rate of clearance of the active ingredient from the intended site of administration, the size and surface area of the particle, the amount of the active ingredient initially present in the core, the presence of other compounds within the core that affect the rate of release of the active ingredient, the permeability of the coating(s) to the active pharmaceutical ingredient, and the rate of degradation of the coating(s), as well as other factors.

Release control may be effected or optimized through the types of acid or base labile agents and alkalinizing or acidifying agents used, the number of coats, the order in which they are deposited, the width of coats and surface area covered, the ratios of the components in the mix and the nature of their interaction.

Incorporating an active substance as described, in the formulation herein, may be useful for (1) reducing the risk of accidental or intentional overdose, (2) increasing the amount of time required for an overdose to occur, thereby increasing the likelihood of a suitable timely intervention, (3) reducing abuse potential of addictive substances, (4) reducing the chance or opportunity for a patient to mistakenly or purposely ingest a higher dose of an addictive active substance and become addicted, and (5) reducing at least one mode of abuse, for example, the illicit use by snorting/inhalation, parenteral administration, or crushing and oral ingestion of formulations intended for oral administration.

The formulations may comprise additives such as polyethylene oxide polymers, polyethylene glycol polymers, cellulose ether polymers, cellulose ester polymers, homo- and copolymers of acrylic acid cross-linked with a polyalkenyl polyether, poly(meth)acrylates, homopolymers (e.g., polymers of acrylic acid crosslinked with allyl sucrose or allyl pentaerythritol), copolymers (e.g., polymers of acrylic acid and C10-C30 alkyl acrylate crosslinked with allyl pentaerythritol), interpolymers (e.g., a homopolymer or copolymer that contains a block copolymer of polyethylene glycol and a long chain alkyl acid ester), disintegrants, ion exchange resins, polymers reactive to intestinal bacterial flora (e.g., polysaccharides such as guar gum, inulin obtained from plant or chitosan and chondrotin sulphate obtained from animals or alginates from algae or dextran from microbial origin) and pharmaceutical resins.

In some formulations, the core and/or the coat may contain ingredients that, when combined with an aqueous solution, will agglomerate to prevent abuse. Such combinations of ingredients include swellable materials such as PEO and Eudragit RL (or other non-enteric compounds). In general, a formulation may comprise at least one active substance; and at least one excipient, wherein dissolution of the pulverized/milled formulation in alcoholic and/or non-alcoholic beverages causes the formulation to agglomerate.

In some formulations, the core and/or one or more coat may contain a disintegrant in an amount of from about 0% to 99% by weight, typically from about 1% to 90% by weight and more typically from 2% to 85%.

Any one of these materials may be present in the formulation or composition in about from 0% to 99% by weight, typically from about 1% to 90% by weight and more typically from 5% to 85%.

The formulations may optionally comprise a pharmaceutically acceptable nasal irritant such as *capsicum* oleoresin. A nasal irritant can produce nasal irritation and a feeling of annoyance when the composition is brought in contact with the nasal membrane. The irritant agent is generally not in amounts sufficient to precipitate allergic type reactions or immune response upon snorting. U.S. Pat. No. 7,157,103 suggests the use of various irritants in preparing pharmaceutical formulations including, for example, capsaicin, a capsaicin analog with similar type properties as capsaicin, and the like. Some capsaicin analogues or derivatives include for example, resiniferatoxin, tinyatoxin, heptanoylisobutylamide, heptanoyl guaiacylamide, other isobutylamides or guaiacylamides, dihydrocapsaicin, homovanillyl octylester, nonanoyl vanillylainide, or other compounds of the class known as vanilloids. Resiniferatoxin is described, for example, in U.S. Pat. Nos. 5,290,816, and 4,812,446 describes capsaicin analogs and methods for their preparation.

Some examples of controlled release agents that may be used in the formulation of the invention include naturally occurring or synthetic, anionic or nonionic, hydrophobic, hydrophilic rubbers, polymers, starch derivatives, cellulose derivatives, polysaccharides, carbomer, reseins, acrylics, proteins, vinyl-pyrrolidone-vinyl-acetate-copolymers, galactomannan and galactomannan derivatives, carrageenans and the like. Specific examples are acacia, tragacanth, Xanthan gum, locust bean gum, guar-gum, karaya gum, pectin, arginic acid, polyethylene oxide, polyethylene glycol, propylene glycol arginate, hydroxypropyl methylcellulose, methylcellulose, hydroxypropyl cellulose, hydroxyethyl cellulose, carboxymethylcellulose sodium, polyvinylpyrrolidone, carboxyvinyl polymer, sodium polyacrylate, a starch, sodium carboxymethyl starch, albumin, dextrin, dextran sulfate, agar, gelatin, casein, sodium casein, pullulan, polyvinyl alcohol, deacetylated chitosan, polyethyoxazoline, poloxamers, ethylcellulose, chitin, chitosan, cellulose esters, aminoalkyl methacrylate polymer, anionic polymers of methacrylic acid and methacrylates, copolymers of acrylate and methacrylates with quaternary ammonium groups, ethylacrylate methylmethacrylate copolymers with a neutral ester group, polymethacrylates, surfactants, aliphatic polyesters, zein, polyvinyl acetate, polyvinyl chloride, and the like. Further examples of pharmaceutically acceptable acrylic polymers that may also be used include, but are not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly(methyl methacrylate), poly(methyl methacrylate) copolymer, polyacrylamide, aminoalkyl methacrylate copolymer, poly (methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH independent or pH dependent.

Further examples of additives that may be used in the formulation of the invention include, but are not limited to, ethyl lactate, phthalates such as dimethyl phthalate (DMP), diethyl phthalate (DEP), dibutyl phthalate (DBP), dioctyl phthalate, glycol ethers such as ethylene glycol diethyl ether, propylene glycol monomethyl ether, PPG-2 myristyl ether propionate, ethylene glycol monoethyl ether, diethylene glycol monoethyl ether, propylene glycol monotertiary butyl ether, dipropylene glycol monomethyl ether, N-methyl-2-pyrrolidone, 2 pyrrolidone, isopropyl myristate, isopropyl palmitate, octyl palmitate, dimethylacetamide, propylene glycol, propylene glycol monocaprylate, propylene glycol caprylate/caprate, propylene glycol monolaurate, glycofurol, linoleic acid, linoeoyl macrogol-6 glycerides, oleic acid, oleic acid esters such as glyceryl dioleate, ethyl oleate, benzoic acid, oleoyl macrogol-6 glycerides, esters such as ethylbenzoate, benzylbenzoate, sucrose esters, sucrose acetate isobutyrate, esters of lactic acid, esters of oleic acid, sebacates such as dimethyl sebacate, diethyl sebacate, dibutyl sebacate, dipropylene glycol methyl ether acetate (DPM acetate), propylene carbonate, propylene glycol laurate, propylene glycol caprylate/caprate, gamma butyrolactone, medium chain fatty acid triglycerides, glycerol and PEG esters of acids and fatty acids, PEG-6 glycerol mono oleate, PEG-6 glycerol linoleate, PEG-8 glycerol linoleate, caprylic acid esters such as caprylocapryl macrogol-8 glycerides, PEG-4 glyceryl caprylate/caprate, PEG-8 glyceryl caprylate/caprate, polyglyceryl-3-oleate, polyglyceryl-6-dioleate, polyglyceryl-3-isostearate, polyglyceryl polyoleate, decaglyceryl tetraoleate and glyceryl triacetate, glyceryl monooleate, glyceryl monolinoleate, dimethylformamide, dimethylsulfoxide, tetrahydrofuran, caprolactam, decylmethylsulfoxide, and 1-dodecylazacycloheptan-2-one.

The formulation may also contain self-emulsifying or surface active substances with varying hydrophilic lipophilic balance (HLB) values such as polyoxyethylene castor oil, polyoxyethylene hydrogenated castor oil, polyoxyethylene sorbitan fatty acid esters, polyoxyethylene alkyl esters, polyoxyethylene alkyl ethers, polyoxyethylene glycerol esters, sorbitan fatty acid esters, and sodium lauryl sulphate.

Examples of antioxidants that may be used in the formulation is selected from ascorbic acid, fumaric acid, malic acid, a tocopherol, ascorbic acid palmitate, butylated hydroxyanisole, propyl gallate, sodium ascobate, and sodium metabisulfite or other suitable antioxidants and stabilizers.

Examples of plasticizers that may be used in the formulation include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The typical plasticizers are triacetin, acetylated monoglyceride, acetyltributylcitrate, acetyltriethylcitrate, glycerin sorbitol, diethyloxalate, diethylmalate, diethylphthalate, diethylfumarate, dibutylsuccinate, diethylmalonate, dioctylphthalate, dibutylsebacate, triethylcitrate, tributylcitrate, glyceroltributyrate, polyethylene glycol, glycerol, vegetable and mineral oils and the like. Depending on the particular plasticizer, amounts of from 0 to about 25%, and typically about 0.1% to about 20% of the plasticizer can be used. The addition of plasticizer should be approached with caution. In certain compositions it is better not to use plasticizers.

Examples of other additives that may be used as part of the formulations of the invention include, but are not limited to disintegrants, carbohydrates, sugars, sucrose, sorbitol, mannitol, zinc salts, tannic acid salts; salts of acids and bases such as sodium and potassium phosphates, sodium and potassium hydroxide, sodium and potassium carbonates and bicarbonates; acids such as hydrochloric acid, sulfuric acid, nitric acid, lactic acid, phosphoric acid, citric acid, malic acid, fumaric acid, stearic acid, tartaric acid, boric acid, borax, and benzoic acid.

Examples of disintegrants include: alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, powdered cellulose, pregelatinized starch, sodium alginate and starch.

Organic acid(s) may particularly be used, for example, lactic acid, phosphoric acid, citric acid, malic acid, fumaric acid, stearic acid, tartaric acid, and benzoic acid. Such acids modify the pH of the macro and micro environment to facilitate release of the active substance. The acid(s) may be included in the coat(s), including the overcoat, layer(s), and/or core of the formulation.

Materials such as the alkali metal chlorides, ammonium chloride, and chlorides of Ba, Mg, Ca, Cu, Fe and Al; alkali or alkaline earth solutions of acetates, nitrates, phosphates, and hydroxides may be used in this formulation Hygroscopic or aqueous materials may be used but with caution. Limited quantities may be incorporated in certain compositions.

Water insoluble organosoluble polymers may be used in the formulation, which may be any polymers which are insoluble in water, are capable of being homogenously dissolved or dispersed in an organosolvent, and can typically retard the release of active ingredients. By the term "water-insoluble" is intended not susceptible to being dissolved (in water). Specific examples of water insoluble organosoluble polymers are, cellulose ether, cellulose ester, or cellulose ether-ester e.g., ethyl cellulose, acetyl cellulose, and nitrocellulose. Other water insoluble organosoluble polymers that can be used include acrylic and/or methacrylic ester polymers, polymers or copolymers of acrylate or methacrylate polyvinyl esters, polyvinyl acetates, polyacrylic acid esters, and butadiene styrene copolymers, and the like. Typical water insoluble polymers are ethylcellulose, cellulose acetate, polymethacrylates and aminoalkyl methacrylate copolymer.

In further specific examples, the acrylic polymer, includes, but is not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly (methyl methacrylate), poly(methyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The water insoluble polymers can be used either singly or in combinations of two or more.

Water-soluble gel forming polymers, which may be used in the formulation, may be any polymers, which are soluble in water, are capable of being homogenously dissolved or dispersed in an organosolvent, and can typically retard the release of active ingredients. Typically, the water-soluble gel-forming polymer is capable of hydrating quickly and forming strong, viscous gels. By the term "water-soluble" is intended susceptible of being dissolved (in water). Suitable water-soluble gel forming polymers include those which can form hydrocolloid or can form a strong, viscous gel through which an active ingredient is released via diffusion or wicking or erosion or swelling. They include naturally occurring or synthetic, anionic or nonionic, polyethylene oxide, hydrophilic rubbers, starch derivatives, cellulose derivatives, proteins, and the like. Specific non-limiting examples are polyethylene oxide and or its derivatives, gelatin, such as alginates, pectins, carrageenans, or xanthan; cellulose derivatives, such as methyl cellulose, hydroxypropylcellulose, hydroxyethylcellulose, hydroxypropyl methylcellulose, or sodium carboxymethylcellulose; starch and starch derivatives such as a starch or sodium carboxymethyl starch; galactomannan and galactomannan derivatives; polyvinylpyrrolidone, polyvinyl alcohol, polyvinyl acetate and the like, vinyl-pyrrolidone-vinyl-acetate-copolymers, acacia, tragacanth, xanthan gum, locust bean gum, guar-gum, karaya gum, pectin, arginic acid, polyethylene oxide, Carbomer, polyethylene glycols, polypropylene glycols, carboxyvinyl polymer, sodium polyacrylate, albumin, dextrin, dextran sulfate, agar, gelatin, casein, sodium casein, pullulan, deacetylated chitosan, polyethyoxazoline, polyethylene oxide, poloxamers and the like. Of these, typical ones are polyethylene oxide, hydroxyethyl cellulose, hydroxypropyl methylcellulose, methylcellulose, hydroxypropyl cellulose, carbomer, polyethylene glycol, poloxamers, starch derivatives and polyvinylpyrrolidone. Water-soluble gel forming polymers can be used either singly or in combinations of two or more.

Polymeric coats may also be comprised of: hydrophobic or water repellant material such as oils, fats, waxes, higher alcohols; pH sensitive polymers; enteric polymers; or any other polymer, component or material known to be useful for preparing a controlled release coating. The polymers used in the formulation may be pH insensitive or pH sensitive.

For a delivery formulation designed to be orally administered to the digestive tract, polymers that are known to be orally ingestible can be used and include, for example, polyvinyl alcohol, hydroxypropyl methyl cellulose, and other cellulose-based polymers. Other known polymers useful for enteral delivery include polymer materials, which preferentially dissolve or disintegrate at different points in the digestive tract. Such polymers include, for example, the known acrylic and/or methacrylic acid-based polymers, which are soluble in intestinal fluids, e.g. the Eudragit™ series of commercially available polymers. Examples of these include Eudragit E™, such as Eudragit E 100™ which preferentially dissolves in the more acid pH of the stomach, or enteric polymers such as Eudragit L™ and/or Eudragit S™ which preferentially dissolve in the more alkaline pH of the intestine, or polymers which dissolve slowly, e.g. a predetermined rate in the digestive tract, such as Eudragit RL™, e.g. Eudragit RL 100™, and/or Eudragit RS™ e.g. Eudragit R100™, and/or blends of such Eudragit™ polymers.

Polymeric coats may also be comprised of: ion exchange resins and or polymers reactive to intestinal bacterial flora (e.g., polysaccharides such as guar gum, inulin obtained from plant or chitosan and chondrotin sulphate obtained from animals or alginates from algae or dextran from microbial origin)

Hydrophobic or water repellant material that may be present is chosen from oil and fats, waxes, higher fatty acids, fatty acid esters, higher alcohols, hydrocarbons, and metal salts of higher fatty acids. Specific examples of oils and fats include plant oils, e.g. cacao butter, palm oil, Japan wax (wood wax), coconut oil, etc.; animal oils, e.g. beef tallow, lard, horse fat, mutton tallow, etc.; hydrogenated oils of animal origin, e.g. hydrogenated fish oil, hydrogenated whale oil, hydrogenated beef tallow, etc.; hydrogenated oils of plant origin, e.g. hydrogenated rape seed oil, hydrogenated castor oil, hydrogenated coconut oil, hydrogenated soybean oil, etc.; and the like. Of these hydrogenated oils are typical as an oil component of the present invention.

Specific examples of waxes that may be present include plant waxes, e.g. carnauba wax, candelilla wax, bayberry wax, auricurry wax, espalt wax, etc.; animal waxes, e.g. bees wax, breached bees wax, insect wax, spermaceti, shellac, lanolin, etc; and the like. Of these typical ones are carnauba wax, white beeswax and yellow beeswax.

Paraffin, petrolatum, microcrystalline wax, and the like, are given as specific examples of hydrocarbons, with typical hydrocarbons being paraffin and microcrystalline wax.

Given as examples of higher fatty acids are caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, and the like. Of these, preferable are myristic acid, palmitic acid, stearic acid, and behenic acid.

Specific examples of higher alcohols are lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, corianyl alcohol, ceryl alcohol, and myricyl alcohol. Particularly preferable alcohols are cetyl alcohol, stearyl alcohol, and the like.

Specific examples of esters are fatty acid esters, e.g. myristyl palmitate, stearyl stearate, myristyl myristate, behenyl behenate, ceryl lignocerate, lacceryl cerotate, lacceryl laccerate, etc.; glycerine fatty acid esters, e.g. lauric monoglyceride, myristic monoglyceride, stearic monoglyceride, behenic monoglyceride, oleic monoglyceride, oleic stearic diglyceride, lauric diglyceride, myristic diglyceride, stearic diglyceride, lauric triglyceride, myristic triglyceride, stearic triglyceride, acetylstearic glyceride, hydoxystearic triglyceride, etc.; and the like. Glycerine fatty acid esters are more typical.

Specific examples of metal salts of higher fatty acid are calcium stearate, magnesium stearate, aluminum stearate, zinc stearate, zinc palmitate, zinc myristate, magnesium myristate, and the like, with preferable higher fatty acid salts being calcium stearate and magnesium stearate.

A coating composition may also contain other additives such as disintegrants and additives normally found in coatings used in the pharmaceutical art such as plasticizers, anti-tacking agents such as talc and coloring agents.

Coloring agents may be added for elegance and aesthetics or to differentiate products and may be chosen, for example, from metal oxide pigments or Aluminum Lake dyes.

A coating composition may include an anti-tacking agent such as talc. Other examples of suitable anti-tacking agent are glycerol monostearate, calcium stearate, colloidal silicon dioxide, glycerin, magnesium stearate, and aluminum stearate.

The compositions are typically formulated to be compatible and result in stable products.

The formulation or composition may be used for treatment of a patient, for example, an animal and more particularly, a mammal. By mammal, is meant any member of the class of Mammalia that is characterized by being a vertebrate having hair and mammary glands. Examples include, without limitation, dog, cat, rabbit, horse, pig, goat, cow, and human being. The formulation or composition of the present invention may be administered to any animal patient or mammalian patient that is in need of treatment with a site specific, timed, pulsed, chronotherapeutic, extended, or controlled release of an active ingredient. In one example, a delivery formulation of the present invention is used for treating a horse, a dog or a cat. In another example, a delivery formulation of the present invention is used for treating a human being.

A medical condition or overdose may be prevented or treated by administering to a patient a formulation or composition comprising a therapeutically effective amount of an addictive substance with quick onset and sustained action of relief.

In certain examples of methods of preparing or using the said formulation or composition, the administration in man or animal may be internal, such as oral or parenteral. Such internal parenteral administration includes but is not limited to intravascular, intramuscular, subcutaneous, intradermal, implantation, and intracavitary routes of administration, as well as application to the external surface of an internal bodily organ, such as during a surgical or laparoscopic procedure. The administration may be topical, including administration to the skin or to a mucosal surface, including the oral, vaginal, rectal surfaces, or to the surface of the eye. Most typically, the formulation is orally adminstrable.

The formulation may also be in the form of a solid. The means and area of application will depend on the particular condition that is being treated. The formulation may be dispensed using any suitable formulation and/or dispensing formulation. For example, it may be taken orally, implanted, or as a depot. It may be targeted at specific sites in the gastrointestinal tract (GU) or to specific organs. As another example, the formulation may also be applied transdermally in a pouch or patch.

Solid particles may be prepared by conventional techniques. They may be milled to required size or surface area where necessary. The typical technique is by dry or wet granulation or hot melt extrusion or roller compaction of an active substance, controlled release agent(s) and excipients such as solubilizing agents, emulsifying agents, suspending agents, fillers, compression agents, stabilizers, pH altering agents, buffers, lubricants, disintegrants and glidants.

Fillers, such as lactose, and compression agents such as microcrystalline cellulose, lubricants such as magnesium stearate and glidants such silicone dioxide may, in certain examples, be included in the core. The core onto which the coating is applied contains the active component. The core may be a tablet, capsule, caplet, pellet, spherical or irregular in shape. The core may be made up of multiple layers by press coating or solution coating. The core may contain a loading dose.

In certain examples, swellable polymeric materials such as hydrogels that swell and expand significantly are included in the core.

Excipients may be homogenously mixed with an active ingredient in a core particle. Excipients may be selected from antiadherents, binders, diluents, emulsifying agents, suspending agents, compression agents, extrusion agents, pH altering agents, buffers, glidants, lubricants, solubilizers, wetting agents, surfactants, penetration enhancers, pigments, colorants, flavoring agents, sweeteners, antioxidants, acidulants, stabilizers, antimicrobial preservatives and binders.

Extrusion agents include, for example, copolyvidone; copovidone; VPNAc copolymer 60/40; copolymer of 1-vinyl-2-pyrrolidone and vinyl acetate in a ratio of 6:4 by mass, Kollidon VA 64/Fine, Kollidon SR, Kollidon 12/17P, Kollidon 25, Kollidon 30/90, Soluplus (graft copolymer of polyethylene glycol, polyvinyl caprolactam and polyvinylacetate, Cremaphor RH 40.

Excipients are biologically inert ingredients, which enhance the therapeutic effect. The filler or diluent (e.g. lactose or sorbitol) is a bulking agent, providing a quantity of material, which can accurately be formed into a tablet. The binders and adhesives (e.g. methyl cellulose or gelatin) hold the ingredients together so that they form a tablet and hold together. Lubricants (e.g. magnesium stearate or calcium stearate) are added to improve powder flow so that the die fills accurately; they also reduce the friction between the tablet and the machine so that the process progresses smoothly and uniformly.

Anti-adherents are used to reduce the adhesion between the powder (granules) and the punch faces and thus prevent tablet sticking to the punches.

Binders hold the ingredients in a tablet together. Binders ensure that tablets and granules can be formed with required mechanical strength. Binders may be selected from starches, sugars, and cellulose or modified cellulose such as hydroxypropyl cellulose, lactose, or sugar alcohols like xylitol, sorbitol or maltitol. Solution binders are dissolved in a solvent (for example water or alcohol and used in wet granulation processes. Examples of solution binders are gelatin, cellulose, cellulose derivatives, polyvinyl pyrrolidone, starch, sucrose and polyethylene glycol. Dry binders are added to a powder blend, either after a wet granulation step, or as part of a direct powder compression. Examples of dry binders are cellulose, methyl cellulose, polyvinyl pyrrolidone, polyethylene glycol. A commonly used binder or compression agent is microcrystalline cellulose. Microcrystalline and powdered cellulose products are sold under the tradenames Avicel™ PH (FMC Corporation, Philadelphia, Pa.) and Solka Floc™ (Penwest Company, Patterson N.Y.). Microcrystalline cellulose may be used in various techniques such as direct compression, dry granulation, wet granulation, or extrusion-spheronization.

Compression agents are materials that may be compacted. Compression agents may be added to increase the overall hardness of a core particle. Compression agents have inherently high compactibility due to properties of plastic deformation and limited elastic recovery. Non-limiting examples of materials that find use as compression agents are microcrystalline cellulose, silicified microcrystalline cellulose (for example Prosolv™ produced by JRS Pharma), oxidized polyethylene, calcium hydrogen phosphate dehydrate, dextrate, or sugar.

Fillers or diluents are added for bulk to fill out the size of a tablet or capsule, making it practical to produce and convenient for the consumer to use. Fillers/diluents are typically inert, compatible with the other components of the formulation, non-hygroscopic, soluble, relatively cheap, compactible, and typically tasteless or pleasant tasting. Plant cellulose (pure plant filler) is a popular filler in tablets or hard gelatin capsules. Dibasic calcium phosphate is another popular tablet filler. A range of vegetable fats and oils can be used in soft gelatin capsules.

Other examples of fillers include: lactose, sucrose, glucose, mannitol, sorbitol, and, calcium carbonate. Fillers/diluents are typically selected from microcrystalline cellulose, plant cellulose, calcium phosphate, mannitol, sorbitol, xylitol, glucitol, ducitol, inositiol, arabinitol; arabitol, galactitol, iditol, allitol, fructose, sorbose, glucose, xylose, trehalose, allose, dextrose, altrose, gulose, idose, galactose, talose, ribose, arabinose, xylose, lyxose, sucrose, maltose, lactose, lactulose, fucose, rhamnose, melezitose, maltotriose, and raffinose. Typical sugars include mannitol, lactose, sucrose, sorbitol, trehalose, glucose.

Glidants are used to improve the flowability of the powder or granules or both. Some examples of glidant(s) are silicon dioxide, starch, calcium silicate, Cabosil, Syloid, and silicon dioxide aerogels. Typically, silicon dioxide is used.

Lubricants prevent ingredients from clumping together and from sticking to the tablet punches or capsule-filling machine. Lubricants also ensure that tablet formation and injection can occur with low friction between the solid and die wall. Some examples of lubricant(s) are alkali stearates such as magnesium stearate, calcium stearate, zinc stearate, polyethylene glycol, adipic acid, hydrogenated vegetable oils, sodium chloride, sterotex, glycerol monostearate, talc, polyethylene glycol, sodium benzoate, sodium lauryl sulfate, magnesium lauryl sulfate, sodium stearyl fumarate, light mineral oil and the like may be employed. Waxy fatty acid esters, such as glyceryl behenate, sold as "Compritol" products, can be used. Other useful commercial lubricants include "Stear-O-Wet" and "Myvatex TL". Common minerals like talc or silica, and fats, e.g. vegetable stearin, glycerol monostearate, magnesium stearate or stearic acid are typically used lubricants.

Sorbents are used for moisture proofing by limited fluid sorbing (taking up of a liquid or a gas either by adsorption or by absorption) in a dry state.

Surfactants, wetting agents and solubilisers such as glycerol monostearate, cetostearyl alcohol, cetomacrogol emulsifying wax, sorbitan esters, polyoxyethylene alkyl ethers (e.g., macrogol ethers such as cetomacrogol 1000), polyoxyethlylene castor oil derivatives, polyoxyethylene sorbitan fatty acid esters (e.g., TWEEN™), polyoxyethylene stearates, sodium dodecylsulfate, Tyloxapol (a nonionic liquid polymer of the alkyl aryl polyether alcohol type, also known as superinone or triton) is another useful solubilisers. Most of these solubilisers, wetting agents and surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986).

Typical wetting agents include tyloxapol, poloxamers such as PLURONIC™ F68, F127, and F108, which are block copolymers of ethylene oxide and propylene oxide, and polyxamines such as TETRONIC™ 908 (also known as POLOXAMINE™ 908), which is a tetrafunctional block copolymer derived from sequential addition of propylene oxide and ethylene oxide to ethylenediamine (available from BASF), dextran, lecithin, dialkylesters of sodium sulfosuccinic acid such as AEROSOL™ OT, which is a dioctyl ester of sodium sulfosuccinic acid (available from American Cyanimid), DUPONOL™ P, which is a sodium lauryl sulfate (available from DuPont), TRITON™ X-200, which is an alkyl aryl polyether sulfonate (available from Rohm and Haas), TWEEN™ 20 and TWEEN™ 80, which are polyoxyethylene sorbitan fatty acid esters (available from ICI Specialty Chemicals), Carbowax 3550 and 934, which are polyethylene glycols (available from Union Carbide), Crodesta F-110, which is a mixture of sucrose stearate and sucrose distearate, and Crodesta SL-40 (both available from Croda Inc.), and SA90HCO, which is $C_{18}H_{37}$—$CH_2$ (CON($CH_3$)$CH_2$($CHOH$)$_4$$CH_2OH$)$_2$.

Wetting agents which have been found to be particularly useful, include Tetronic 908, the Tweens, Pluronic F-68 and polyvinylpyrrolidone. Other useful wetting agents include decanoyl-N-methylglucamide; n-decyl-β-D-glucopyranoside; n-decyl-β-D-maltopyranoside; n-dodecyl-β-D-glucopyranoside; n-dodecyl-β-D-maltoside; heptanoyl-N-methylglucamide; n-heptyl-β-D-glucopyranoside; n-heptyl-β-D-thioglucoside; n-hexyl-β-D-glucopyranoside; nonanoyl-N-methylglucamide; n-octyl-β-D-glucopyranoside; octanoyl-N-methylglucamide; n-octyl-β-D-glucopyranoside; and octyl-β-D-thioglucopyranoside. Another typical wetting agent is p-isononylphenoxypoly(glycidol), also known as Olin-10G or Surfactant 10-G (commercially available as 10G from Olin Chemicals). Two or more wetting agents can be used in combination.

The pharmaceutical formulation or formulation may further include a pegylated excipient. Such pegylated excipients include, but are not limited to, pegylated phospholipids, pegylated proteins, pegylated peptides, pegylated sugars, pegylated polysaccharides, pegylated block-co-polymers with one of the blocks being PEG, and pegylated hydrophobic compounds such as pegylated cholesterol. Representative examples of pegylated phospholipids include 1,2-diacyl 1-sn-glycero-3-phosphoethanolamine-N-[Poly(ethylene glycol) 2000] ("PEG 2000 PE") and 1,2-diacyl-sn-glycero-3-phosphoethanolamine-N-[-Poly(ethylene glycol) 5000]("PEG 5000 PE"), where the acyl group is selected, for example, from dimyristoyl, dipalmitoyl, distearoyl, diolcoyl, and 1-palmitoyl-2-oleoyl.

Additional excipients may be included in the formulation of the present invention. Further examples of excipients can include pigments, colorants, flavoring agents, preservatives and sweeteners. Flavors and colors are added to improve the taste or appearance of a formulation. Some typical preservatives used in pharmaceutical formulations are antioxidants such as vitamin A, vitamin E, vitamin C, and selenium, amino acids such as cysteine and methionine, citric acid and sodium citrate, or synthetic preservatives such as methyl paraben and propyl paraben. Sweeteners are added to make the ingredients more palatable, especially in chewable tablets such as antacid or liquids like cough syrup. Sugar may be used to disguise unpleasant tastes or smells. While for addictive substances bittering agents may be added make the administration of a non-intact form objectionable.

One skilled in the art can select appropriate excipients for use in the formulation of the present invention.

The formulation may comprise an excipient that is a swellable material such as a hydrogel in amounts that can swell and expand. Examples of swellable materials include polyethylene oxide, hydrophilic polymers that are lightly cross-linked, such cross-links being formed by covalent or ionic bond, which interact with water and aqueous biological fluids and swell or expand to some equilibrium state. Swellable materials such as hydrogels exhibit the ability to swell in water and retain a significant fraction of water within its structure, and when cross-linked they will not dissolve in the water. Swellable polymers can swell or expand to a very high degree, exhibiting a 2 to 50 fold volume increase. Specific examples of hydrophilic polymeric materials include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like. Other examples of swellable materials include hydrogels exhibiting a cross-linking of 0.05 to 60%, hydrophilic hydrogels known as Carbopol acidic carboxy polymer, Cyanamer™ polyacrylamides, cross-linked water-swellable indene-maleic anhydride polymers, Good-Rite™ polyacrylic acid, starch graft copolymers, Aqua-Keeps™ acrylate polymer, diester cross-linked polyglucan, and the like. Methods for testing swellable materials with regards to polymer imbibition pressure and hydrogel-water interface interaction are described in U.S. Pat. No. 4,327,725.

In a certain example, the formulation may be coated with salt forming, and/or ion exchanging resin, and/or a non-disintegrating and/or non-semi-permeable coat. Materials useful for forming the non-disintegrating non-semi-permeable coat are ethylcellulose, polymethylmethacrylates, methacrylic acid copolymers and mixtures thereof.

In yet another embodiment, the formulation is coated with a non-disintegrating semipermeable coat. Materials useful for forming the non-disintegrating semipermeable coat are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,612,008. The most typical non-disintegrating semipermeable coating material is cellulose acetate comprising an acetyl content of 39.3 to 40.3%, commercially available from Eastman Fine Chemicals.

In an alternative embodiment, the non-disintegrating semipermeable or non-disintegrating non-semi-permeable coat can be formed from the above-described polymers and materials that will form pores or channels in the coat. The pore forming agents or channeling agents dissolve on contact with fluid and form passages through which fluid and active pharmaceutical ingredient(s) can move through the coat. The pore forming agent or channeling agent can be a water-soluble material or an enteric material. Some general examples of pore forming agents or channeling agents are water soluble materials such as cellulose ethers, polyethylene glycols or microcrystalline cellulose. Some further examples of pore forming agents or channeling agents are sodium chloride, potassium chloride, lactose, sucrose, sorbitol, mannitol, polyethylene glycol (PEG), for example PEG 600, polyvinyl pyrolidone, propylene glycol, hydroxypropyl cellulose, hydroxypropyl methycellulose, hydroxypropyl methylcellulose phthalate, cellulose acetate phthalate, polyvinyl alcohols, methacrylic acid copolymers and mixtures thereof.

The active pharmaceutical ingredient(s) that are water-soluble or that are soluble under intestinal conditions may also be used to create pores in the coat.

The pore forming agent comprises approximately 0 to about 75% of the total weight of the coating, most typically about 0.5% to about 25% of the total weight of the coating. The pore-forming agent dissolves or leaches from the coat to form pores in the coat for the fluid to enter the core and dissolve the active ingredient.

As used herein the term pore includes an aperture, orifice, bore, channel, hole, a discrete area of weakness or as created by soluble or leachable materials.

Method of Making the Formulations

The formulations can be made by any known methods. For example, the core can be made by blending and direct compression without wet granulation; by hot melt extrusion; by hot melt granulation; by roll compaction, slugging or a chilsonator; and/or by extrusion spheronization. A loading dose or any coating may be press coated onto at least a portion of the core as a separate layer(s).

In some embodiments, the loading dose is applied by spraying coating, dry coating, press coating, encapsulation, or by a combination of these methods.

In a specific example, an acid labile coating is prepared by adding an acid labile polymer and anti-tacking agent to an organosolvent or aqueous system and mixing until homogenously dissolved or dispersed using a low or high shear mixer. The acid labile coating may be applied to a core using standard coating methodology. Likewise, an alkalinizing coat is prepared by adding an alkalinizing agent and a film coating system such as Opadry to a solvent and mixing until homogenously dissolved or dispersed. The alkalinizing coating may be applied to the acid labile coating using standard coating methodology.

The alkalinizing coat contains at least one alkalinizing agent that is capable of undergoing the following neutralization with stomach acid:

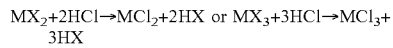

where M is a metal ion (e.g. alkaline earth metal; alkali metal; aluminum; etc.) and X is a basic ion (e.g. hydroxide; silicate; oxide; carbonate; citrate, acetate; etc.).

In another example, a base labile coating is prepared by adding a base labile polymer and anti-tacking agent to an organosolvent or aqueous system and mixing until homogenously dissolved or dispersed using a low or high shear mixer. The base labile coating may be applied to a core using standard coating methodology. Likewise, an acidfying coat is prepared by adding an acidifying agent to a solvent and mixing until homogenously dissolved or dispersed. The acidifying coating may be applied to the base labile coating using standard coating methodology. A further base labile coat is prepared by adding a base labile polymer and a film coating system such as Opadry to a solvent and mixing until homogenously dissolved or dispersed. The base labile coat may be applied to acidifying coat using standard coating methodology.

The formulations described herein may contain one or more active substance, or specifically one or more opioid agonist or narcotic analgesic or abuse-able substances, may be made by any method wherein the particle size or surface area of active ingredient and/or inactive ingredient, quantity or ratio and type of loading dose, controlled release agents, external coat(s) and excipients is optimum to form a formulation with quick onset of action and sustained action thereafter while still capable of abuse resistant properties when ingested in higher than prescribed or recommended doses.

Typically, the entire quantity of the core formulation is dry mixed and homogeneously blended, and made into a solid unit (e.g. tablet, bead, compressed granules formed into any shape, etc.). Thereafter, the acid labile coating is applied directly on the core by press coating, solution coating, or spraying as a layer, for example, such that the acid labile coating surrounds or substantially surrounds the tablet sufficiently to inhibit release of the active substance from the core in a non-acidic environment, while allowing release of the active substance in an acidic environment. Next, the alkalinizing coating is applied directly on the acid labile coating by press coating, solution coating, or spraying as a layer, for example, such that the alkalinizing coating is present on the tablet in an amount sufficient to raise the pH of the environment when a threshold number of tablets are ingested. A cold process under room temperature conditions is typical, however solid substances may be heated to their liquid state prior to incorporation, using such methods as hot melt extrusion.

Alternatively, the formulation may be processed in a jacketed vessel, which allows precise control of the processing temperature. Other pharmaceutically acceptable additives, such as those described above, may be incorporated before, after, or during the addition of controlled release agents or active substances. Wet granulation can also be used.

The solid particles may be of a size and/surface area such that the active ingredient maintains very intimate and close proximity to the polymers and homogeneity. The solid particles may take any convenient form, including, for example, granules, spheroids, pellets, microspheres, nanospheres, microcapsules, or crystals and can be prepared by wet or dry granulation, by extrusion spheronization, by hot melt extrusion, by powder or solution layering, by microencapsulation techniques, by milling and compression techniques or other suitable known techniques. In certain examples, different types of coats may be applied to the formulation.

In certain examples, the particle size of solid materials is less than about 1000 microns. In certain other examples, the particle size of solid materials is less than about 500, 200, 100, or 50 microns and the formulation maintains very intimate and close proximity to the polymers and homogeneity especially when crushed. In certain further, examples the solid particles are sufficiently small and have large surface area such that they are in very intimate and close proximity and homogeneity with one another. These types of formulations may resist abuse or inadvertent misuse.

In certain examples, capsules, for example, soft or hard capsules, envelop the formulations. While both soft and hard capsules may be used, hard capsules may be particularly useful. In certain examples, the capsule is made by applying a polymeric coat of material that result in a plastic or elastic shell in any shape (e.g. pod-like envelope). It could also be a hard gelatin capsule or be made of a metal or alloy of metals, cellulose ether, or be of vegetable or animal origin.

One skilled in the art will also know that capsules made from materials other than gelatin may be used. For example, U.S. Patent Application Publication No. 2006/0099246 pertains to a non-gelatin soft capsule system having a predominantly starch and gelling carrageenan based shell. Carrageenan is a collective term for polysaccharides prepared by alkaline extraction (and modification) from red seaweed (Rhodophycae), mostly of genus Chondrus, Eucheuma, Gigartina and Iridaea. Different seaweeds produce different carrageenans. Carrageenan consists of alternating 3-linked-β-D-galactopyranose and 4-linked-α-D-galactopyranose units. Most, if not all, of the galactose units are substituted with sulfate ester groups. In another example, US Patent Appln. Pub. No. 2006/0004193 (Muller) published Jan. 5, 2006 relates to a tough-elastic material based on starch, which on the one hand has high impact toughness at low humidity, and on the other hand still has a high modulus of elasticity at high humidity and has a high elongation capacity in a broad range of humidity and on account of its property profile is suited to use as edible film and for the packaging of active ingredients, as well as high-quality substitution of gelatin in the area of soft and hard capsules. As another example, PCT Publication WO 01/37817 describes a soft capsule based on thermoplastic starch (TPS) with high softener content. As another example, U.S. Patent Application Publication No. 2005/0196436 relates to a method of producing a film-forming blend of different acyl gellan gums with starch having similar textural and functional properties compared to gelatin. As another example, U.S. Patent Application Publication No. 2007/0077293 (Park) published Apr. 5, 2007 relates to a film-forming composition for hard capsules, comprising 7-12% by weight of starch, 1-6% by weight of a plasticizer, 0.7-3% by weight of a gelling agent, and 79-91.3% by weight of water. As another example, U.S. Patent Application Publication No. 2006/0153909 relates to hard capsules made of a base material containing a cellulose derivative including, for example, one or more of hydroxypropyl methylcellulose, methylcellulose, hydroxypropyl cellulose, hydroxyethyl cellulose, hydroxypropyl methylcellulose phthalate, hydroxypropyl methylcellulose acetate succinate, carmelose, carboxymethylethyl cellulose, cellulose acetate phthalate, and ethylcellulose. Also, additives such as a gelling agent, a gelling aid, a colorant, a plasticizer, an emulsifier, a dispersant, and a preservative may be added to the capsule base material. As yet another example, U.S. Patent Application Publication No. 2005/0186268 describes a hard capsule made mainly of a polymer or copolymer obtained by polymerizing or copolymerizing at least one polymerizable vinyl monomer in the presence of polyvinyl alcohol and/or a derivative thereof. Still many other examples exist, as will be recognized by the skilled person.

In certain examples, a controlled release formulation may be in combination with a non-controlled release formulation containing an opioid antagonist and/or an immediate release non-narcotic analgesic or other pharmaceutically active substances or filled into a capsule or dispensing formulation with a non-controlled release composition containing an opioid antagonist and/or an immediate release non-narcotic analgesic or other pharmaceutically active substances.

In certain examples, dissolution using a USP dissolution tester is not significantly different by modifying the rotation speed of the basket or paddle in the speed range from about 25 rpm to about 150 rpm, or at about 50 rpm and about 100 rpm or at about 50 rpm and about 75 rpm or at about 100 rpm and about 150 rpm. The rotation speed does not generally interact with or compromise the integrity of the formulation and release mechanism, at least in the first one to six hours. When many unit dosage forms are included together in the tester for long periods of time, upwards of, for example, 12 or more hours, some mechanically-induced disintegration of the unit dosage forms may be observed. Formulations that meet these requirements perform consistently in the gastrointestinal tract without fear of collapse or disintegration. These are typically not perturbed, crushed or damaged by gastrointestinal tract content, resident time or motility.

When introducing elements disclosed herein, the articles "a", "an", "the", and "said" are intended to mean that there may be one or more of the elements.

Any range described herein is understood to include any incremental ranges or individual values therebetween.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effects described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1. Comparison of the Effects of Different Alkalinizing Agents on the pH of an Acidic Solution Various alkalinizing agents were added to a solution of 0.1 N HCl with a starting pH of 2.0 and the pH of the solution was tested at different time points. The purpose of these experiments was to provide various examples of alkalinizing agents in varying amounts that could be used to raise the pH of stomach acid sufficiently to reduce dissolution of an acid labile coat. From these experiments, it was concluded that one skilled in the art, based on these examples and teachings, would be able to vary the alkalinizing agent and amounts to yield the desired result.

Table 1 and FIG. 1 show the effects of magnesium hydroxide over a 60 minute timecourse in amounts ranging from 60-120 mg/320 ml solution and from 60-240 mg/500 ml solution. From this timecourse, it can be seen that all tested amounts were able to raise the pH of the solution above 2.0 over the times tested, however, the 100 mg/320 ml (0.3125 mg/ml), 180 mg/500 ml (0.36 mg/ml), 120 mg/320 ml (0.375 mg/ml), 200 mg/500 ml (0.4 mg/ml), and 240 mg/500 ml (0.48 mg/ml) all rapidly raised the pH of the solution to neutral or higher.

TABLE 1

Effect of magnesium hydroxide on the pH of a solution of 0.1N HCl with a starting pH of 2.0.

| Time (Min) | 60 mg per 320 mL | 90 mg per 320 mL | 100 mg per 320 mL | 120 mg per 320 mL | 60 mg per 500 mL | 100 mg per 500 mL | 120 mg per 500 mL | 180 mg per 500 mL | 200 mg per 500 mL | 240 mg per 500 mL |
|---|---|---|---|---|---|---|---|---|---|---|
| 0 | 2.03 | 2.05 | 2.03 | 2.05 | 2.01 | 2.03 | 2.01 | 2.05 | 2.03 | 2.00 |
| 1 | 2.17 | 2.19 | 2.15 | 2.25 | 2.06 | 2.10 | 2.10 | 2.34 | 2.19 | 2.17 |
| 2 | 2.29 | 2.37 | 2.36 | 2.49 | 2.12 | 2.21 | 2.21 | 2.56 | 2.48 | 2.54 |
| 3 | 2.41 | 2.55 | 2.53 | 2.87 | 2.17 | 2.33 | 2.35 | 3.09 | 2.81 | 3.14 |
| 4 | 2.47 | 2.77 | 2.74 | 3.54 | 2.18 | 2.38 | 2.44 | 3.90 | 3.54 | 5.90 |
| 5 | 2.48 | 3.06 | 3.07 | 5.75 | 2.19 | 2.40 | 2.52 | 5.69 | 5.42 | 7.73 |
| 6 | 2.48 | 3.13 | 3.39 | 6.65 | 2.19 | 2.40 | 2.57 | 6.28 | 6.63 | 9.09 |
| 7 | 2.49 | 3.22 | 3.73 | 7.81 | 2.19 | 2.41 | 2.59 | 6.64 | 7.99 | 9.35 |
| 8 | 2.49 | 3.28 | 4.26 | 8.55 | 2.19 | 2.41 | 2.59 | 7.01 | 8.86 | 9.47 |
| 9 | 2.49 | 3.31 | 5.41 | 8.83 | 2.19 | 2.41 | 2.59 | 7.61 | 9.07 | 9.54 |
| 10 | 2.49 | 3.33 | 5.86 | 8.94 | 2.19 | 2.41 | 2.59 | 8.25 | 9.18 | 9.59 |
| 20 | 2.50 | 3.34 | 6.51 | 9.20 | 2.19 | 2.41 | 2.60 | 9.07 | 9.41 | 9.71 |
| 30 | 2.50 | 3.37 | 6.75 | 9.23 | 2.19 | 2.41 | 2.60 | 9.14 | | |
| 40 | 2.50 | 3.35 | 6.92 | 9.27 | | 2.41 | 2.60 | 9.16 | | |
| 50 | 2.50 | 3.35 | 7.01 | 9.24 | | 2.41 | | 9.19 | | |
| 60 | 2.53 | 3.36 | 7.09 | | | 2.41 | | 9.20 | | |

Figure 2:
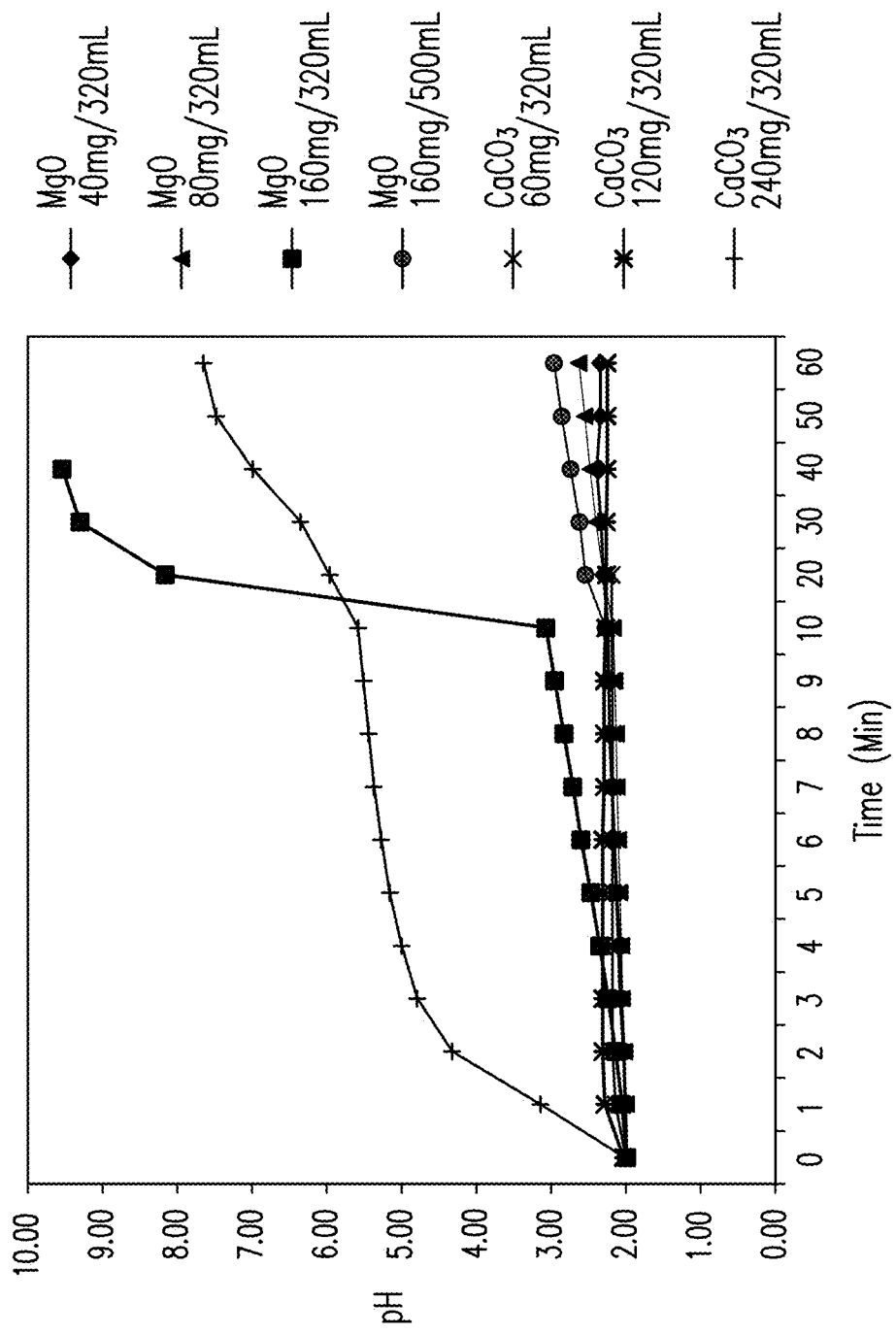
FIG. 2 shows the effects of magnesium oxide and calcium carbonate on the pH of an acidic solution over a 60 minute timecourse in various amounts.

Table 2 and FIG. 2 show the effects of magnesium oxide and calcium carbonate over a 60 minute timecourse in various amounts. From this timecourse, it can be seen that, again, all tested amount were able to raise the pH of the solution above 2.0 over the times tested, however, the 160 mg/320 ml (0.5 mg/ml) magnesium hydroxide and the 240 mg/320 ml (0.75 mg/ml) calcium carbonate both rapidly raised the pH of the solution to neutral or higher.

TABLE 2

Effect of magnesium oxide and calcium carbonate on the pH of a solution of 0.1N HCl with a starting pH of 2.0.

| Time (Min) | MgO 40 mg per 320 mL | MgO 80 mg per 320 mL | MgO 160 mg per 320 mL | MgO 160 mg per 500 mL | CaCO$_3$ 60 mg per 320 mL | CaCO$_3$ 120 mg per 320 mL | CaCO$_3$ 240 mg per 320 mL |
|---|---|---|---|---|---|---|---|
| 0 | 2.01 | 1.99 | 1.99 | 1.98 | 2.00 | 2.03 | 2.02 |
| 1 | 2.01 | 2.00 | 2.05 | 2.00 | 2.14 | 2.28 | 3.14 |
| 2 | 2.03 | 2.02 | 2.14 | 2.02 | 2.18 | 2.31 | 4.32 |
| 3 | 2.08 | 2.05 | 2.24 | 2.05 | 2.18 | 2.31 | 4.79 |
| 4 | 2.10 | 2.06 | 2.35 | 2.07 | 2.18 | 2.31 | 5.00 |
| 5 | 2.13 | 2.08 | 2.47 | 2.12 | 2.18 | 2.31 | 5.16 |
| 6 | 2.16 | 2.10 | 2.60 | 2.15 | 2.18 | 2.31 | 5.27 |
| 7 | 2.19 | 2.12 | 2.71 | 2.18 | 2.18 | 2.29 | 5.37 |
| 8 | 2.22 | 2.13 | 2.83 | 2.22 | 2.18 | 2.29 | 5.44 |
| 9 | 2.23 | 2.15 | 2.95 | 2.24 | 2.18 | 2.29 | 5.51 |
| 10 | 2.24 | 2.17 | 3.07 | 2.27 | 2.19 | 2.27 | 5.58 |
| 20 | 2.30 | 2.30 | 8.16 | 2.54 | 2.19 | 2.26 | 5.96 |
| 30 | 2.33 | 2.40 | 9.30 | 2.62 | | 2.26 | 6.35 |
| 40 | 2.39 | 2.48 | 9.54 | 2.74 | | 2.25 | 6.99 |
| 50 | 2.34 | 2.55 | | 2.86 | | 2.25 | 7.48 |
| 60 | 2.34 | 2.63 | | 2.96 | | 2.25 | 7.65 |

Figure 3:
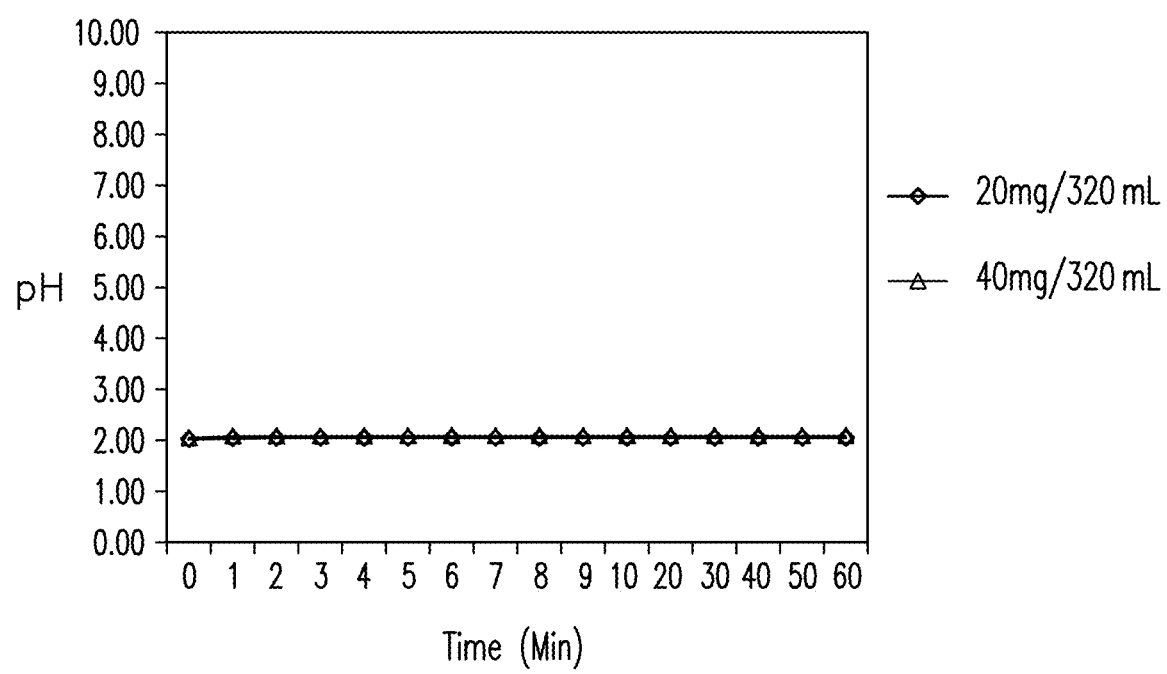
FIG. 3 shows the effects of sodium bicarbonate on the pH of an acidic solution over a 60 minute timecourse in amounts of 20 mg/320 ml acidic solution and 40 mg/320 ml acidic solution.

Table 3 and FIG. 3 show the effects of sodium bicarbonate over a 60 minute timecourse in amounts of 20 mg/320 ml solution and 40 mg/320 ml solution. From this timecourse, it can be seen that both tested amounts were able to raise the pH of the solution above 2.0 over the times tested, however, neither amount tested was sufficient to raise the pH to neutral or higher.

TABLE 3

Effect of sodium bicarbonate on the pH of a solution of 0.1N HCl with a starting pH of 2.0.

| Time (Min) | 20 mg per 320 mL | 40 mg per 320 mL |
| --- | --- | --- |
| 0 | 2.02 | 2.05 |
| 1 | 2.04 | 2.08 |
| 2 | 2.05 | 2.08 |
| 3 | 2.05 | 2.08 |
| 4 | 2.05 | 2.08 |
| 5 | 2.05 | 2.09 |
| 6 | 2.05 | 2.09 |
| 7 | 2.05 | 2.09 |
| 8 | 2.05 | 2.09 |
| 9 | 2.05 | 2.09 |
| 10 | 2.05 | 2.09 |
| 20 | 2.05 | 2.09 |
| 30 | 2.05 | 2.09 |
| 40 | 2.05 | 2.09 |
| 50 | 2.05 | 2.09 |
| 60 | 2.05 | 2.09 |

Figure 4:
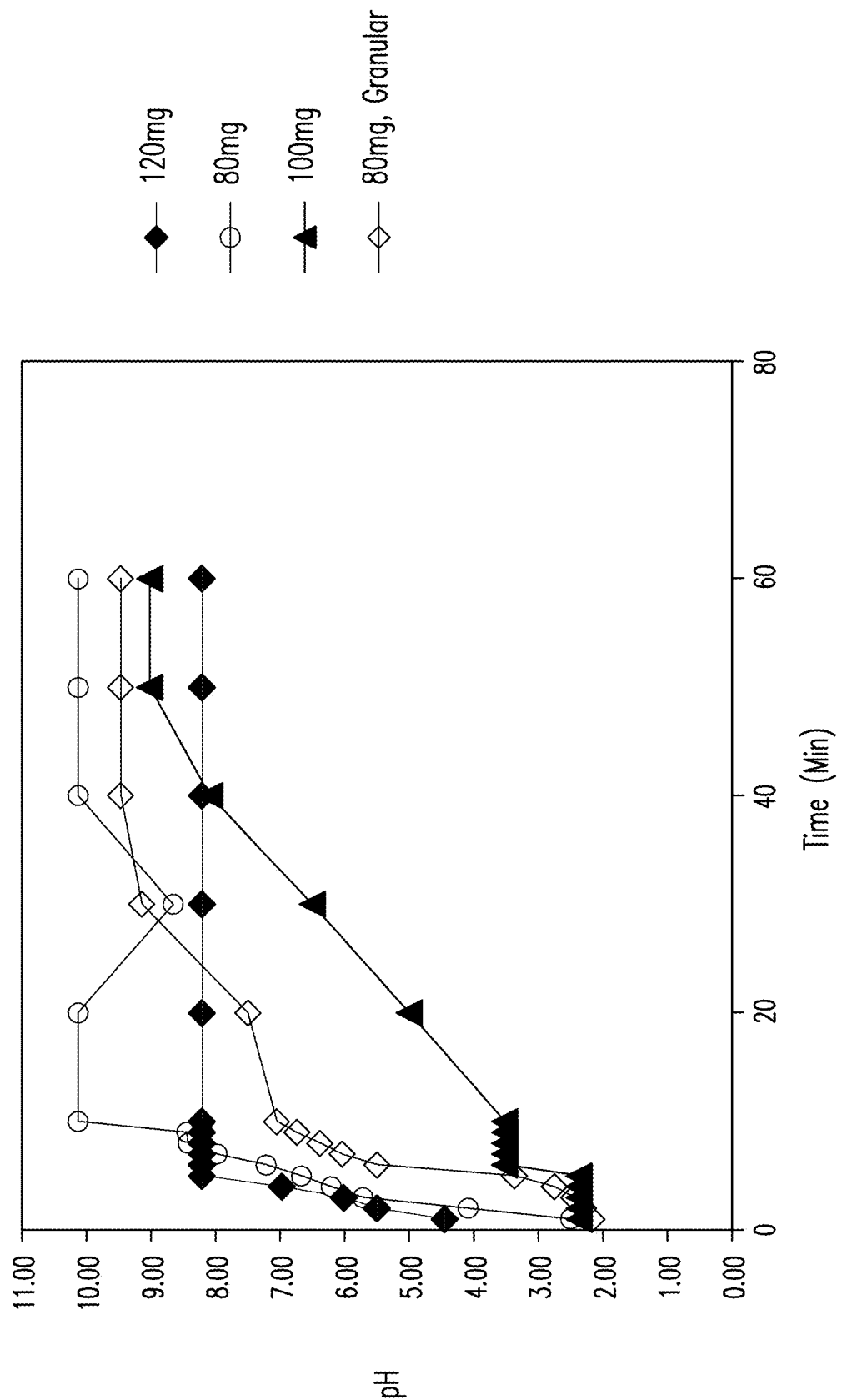
FIG. 4 shows the effects of magnesium oxide on the pH of an acidic solution over a 60 minute timecourse in amounts of 80-120 mg/200 ml acidic solution, in powder form. Additionally shown is a 60 minute timecourse for an amount of 80 mg magnesium oxide in granular form in 200 ml acidic solution.

Table 4 and FIG. 4 show the effects of magnesium oxide over a 60 minute timecourse in amounts of 80-120 mg/200 ml solution. Additionally shown is a 60 minute timecourse for an amount of 80 mg magnesium oxide in granular form in 200 ml solution. From this timecourse, it can be seen that all tested amounts and forms were able to rapidly raise the pH of the solution to neutral or higher, with the granular form lagging slightly behind the powder form of magnesium oxide.

TABLE 4

Effect of magnesium oxide in powder or granular form on the pH of a solution of 0.1N HCl with a starting pH of 2.0.

| Time, min | 80 mg | 100 mg | 120 mg | 80 mg, Granular |
| --- | --- | --- | --- | --- |
| 1 | 2.50 | 2.37 | 4.45 | 2.17 |
| 2 | 4.09 | 2.37 | 5.50 | 2.30 |
| 3 | 5.72 | 2.37 | 6.01 | 2.45 |
| 4 | 6.21 | 2.37 | 6.97 | 2.75 |
| 5 | 6.67 | 2.37 | 8.21 | 3.37 |
| 6 | 7.22 | 3.52 | 8.21 | 5.50 |
| 7 | 7.98 | 3.52 | 8.21 | 6.04 |
| 8 | 8.42 | 3.52 | 8.21 | 6.38 |
| 9 | 8.44 | 3.52 | 8.21 | 6.74 |
| 10 | 10.13 | 3.52 | 8.21 | 7.05 |
| 20 | 10.13 | 5.00 | 8.21 | 7.50 |
| 30 | 8.66 | 6.50 | 8.21 | 9.14 |
| 40 | 10.13 | 8.09 | 8.21 | 9.47 |
| 50 | 10.13 | 9.02 | 8.21 | 9.47 |
| 60 | 10.13 | 9.02 | 8.21 | 9.47 |

Figure 5:
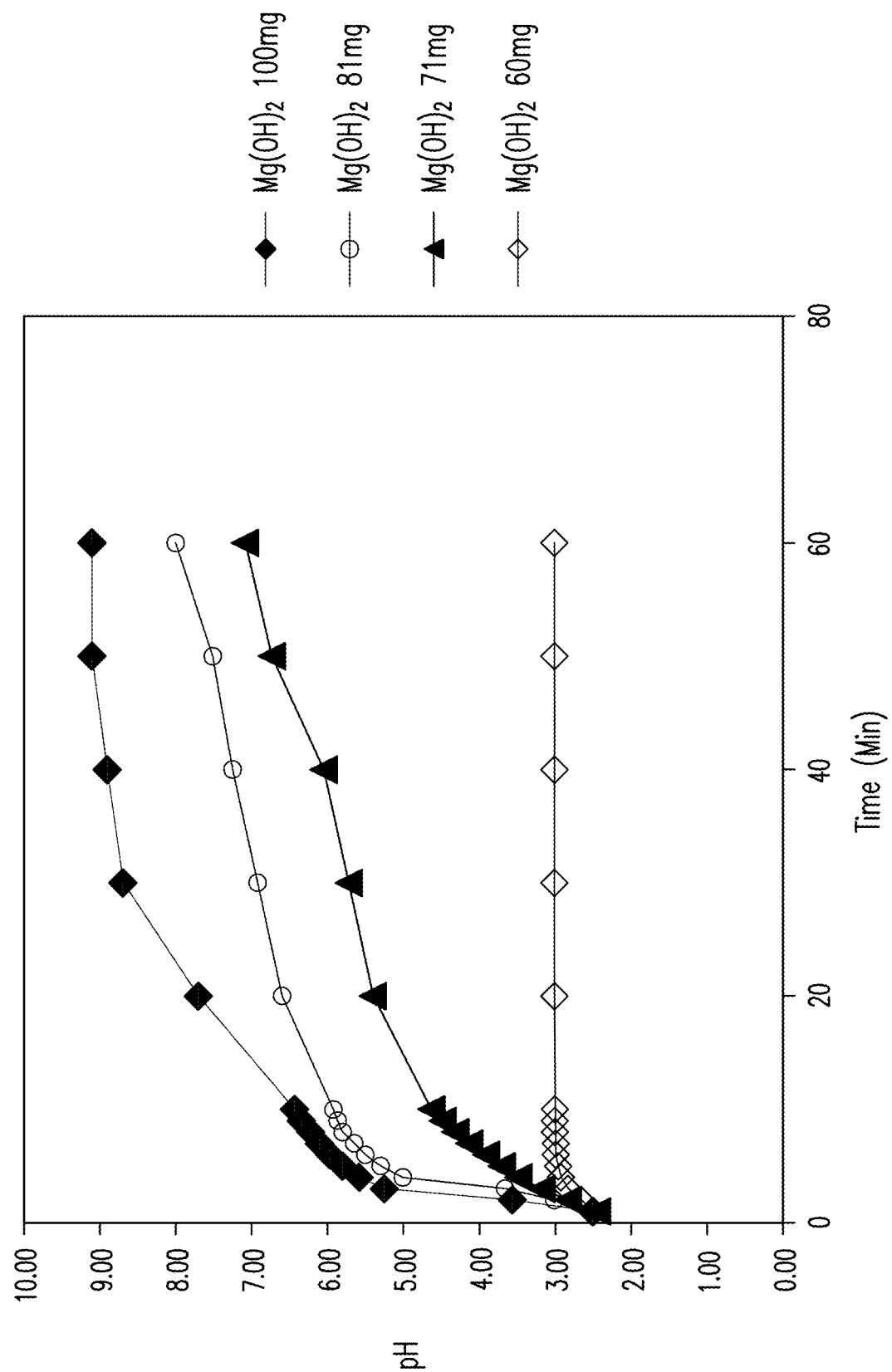
FIG. 5 shows the effects of magnesium hydroxide on the pH of an acidic solution over a 60 minute timecourse in amounts of 60-100 mg/200 ml acidic solution.

Table 5 and FIG. 5 show the effects of magnesium hydroxide over a 60 minute timecourse in amounts of 60-100 mg/200 ml solution. From this timecourse, it can be seen that all tested amount were able to raise the pH of the solution above 2.0 over the times tested, however, the 71 mg/200 ml (0.355 mg/ml), 81 mg/200 ml (0.405), and 100 mg/200 ml (0.5 mg/ml) magnesium hydroxide all raised the pH of the solution to neutral or higher.

TABLE 5

Effect of magnesium hydroxide on the pH of a solution of 0.1N HCl with a starting pH of 2.0.

| Time, min | 100 mg | 81 mg | 71 mg | 60 mg |
| --- | --- | --- | --- | --- |
| 1 | 2.50 | 2.50 | 2.45 | 2.50 |
| 2 | 3.56 | 3.01 | 2.83 | 2.66 |
| 3 | 5.25 | 3.66 | 3.18 | 2.83 |
| 4 | 5.58 | 5.01 | 3.48 | 2.92 |
| 5 | 5.80 | 5.30 | 3.70 | 2.96 |
| 6 | 5.97 | 5.50 | 3.91 | 2.99 |
| 7 | 6.10 | 5.65 | 4.13 | 2.99 |
| 8 | 6.22 | 5.80 | 4.31 | 3.00 |
| 9 | 6.34 | 5.87 | 4.48 | 3.00 |
| 10 | 6.43 | 5.92 | 4.63 | 3.00 |
| 20 | 7.70 | 6.60 | 5.40 | 3.01 |
| 30 | 8.69 | 6.92 | 5.72 | 3.01 |
| 40 | 8.90 | 7.25 | 6.05 | 3.01 |
| 50 | 9.10 | 7.51 | 6.73 | 3.01 |
| 60 | 9.10 | 8.00 | 7.08 | 3.01 |

Figure 6:
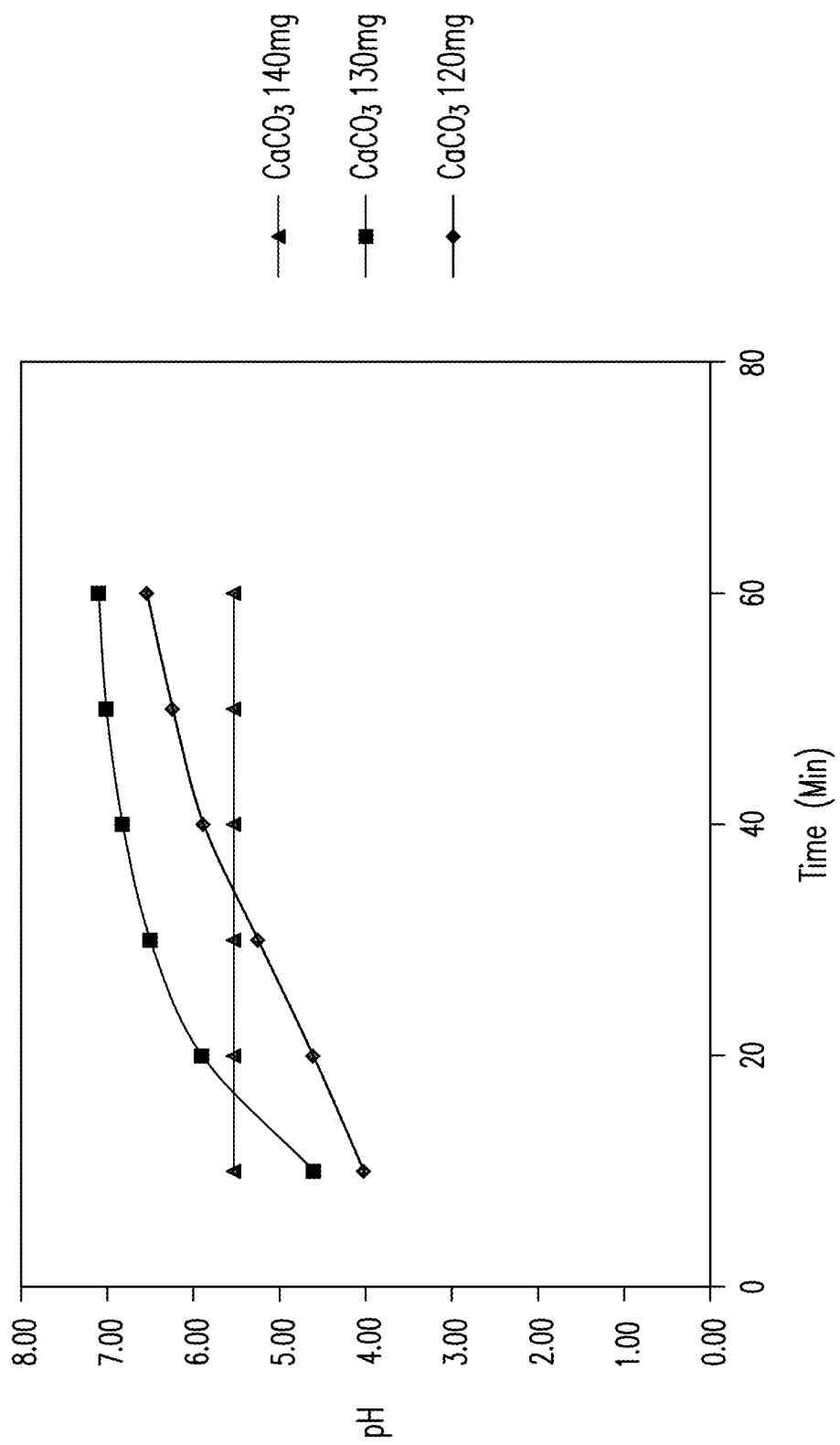
FIG. 6 shows the effects of calcium carbonate on the pH of an acidic solution over a 60 minute timecourse in amounts of 120-140 mg/200 ml acidic solution.

Table 6 and FIG. 6 show the effects of calcium carbonate over a 60 minute timecourse in amounts of 120-140 mg/200 ml solution. From this timecourse, it can be seen that all tested amount were able to raise the pH of the solution to near neutral or neutral.

TABLE 6

Effect of calcium carbonate on the pH of a solution of 0.1N HCl with a starting pH of 2.0.

| Time, min | 140 mg | 130 mg | 120 mg |
| --- | --- | --- | --- |
| 10 | 5.53 | 4.60 | 4.02 |
| 20 | 5.53 | 5.90 | 4.61 |
| 30 | 5.53 | 6.50 | 5.25 |
| 40 | 5.53 | 6.82 | 5.88 |
| 50 | 5.53 | 7.01 | 6.24 |
| 60 | 5.53 | 7.10 | 6.54 |

Figure 7:
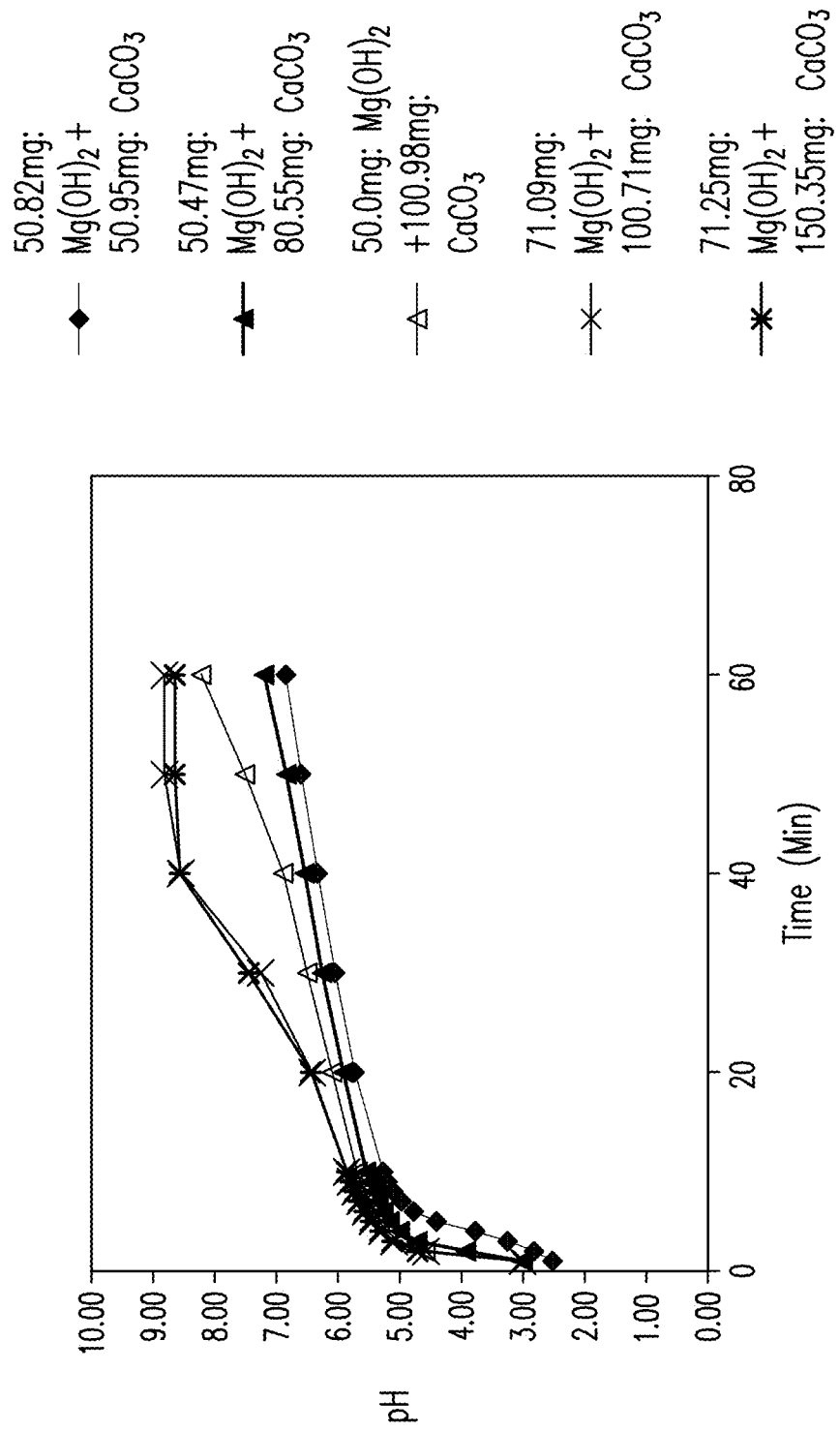
FIG. 7 shows the effects of magnesium hydroxide and calcium carbonate in combination on the pH of an acidic solution over a 60 minute timecourse in amounts of 50-71.25 mg magnesium hydroxide per 200 ml acidic solution and from 50.95-150.35 mg calcium carbonate per 200 ml acidic solution.

Table 7 and FIG. 7 show the effects of magnesium hydroxide and calcium carbonate in combination over a 60 minute timecourse in amounts of 50-71.25 mg magnesium hydroxide per 200 ml solution and from 50.95-150.35 mg calcium carbonate per 200 ml solution. From this timecourse, it can be seen that all tested amounts were able to raise the pH of the solution to near neutral or higher.

TABLE 7

Effect of magnesium hydroxide and calcium carbonate in combination on the pH of a solution of 0.1N HCl with a starting pH of 2.0.

| Time, min | 50.82 mg $Mg(OH)_2$ + 50.95 mg $CaCO_3$ | 50.47 mg $Mg(OH)_2$ + 80.55 mg $CaCO_3$ | 50.0 mg $Mg(OH)_2$ + 100.98 mg $CaCO_3$ | 71.09 mg $Mg(OH)_2$ + 100.71 mg $CaCO_3$ | 71.25 mg $Mg(OH)_2$ + 150.35 mg $CaCO_3$ |
| --- | --- | --- | --- | --- | --- |
| 1 | 2.52 | 3.01 | 3.01 | 3.00 | 3.01 |
| 2 | 2.82 | 3.93 | 4.59 | 4.57 | 4.71 |
| 3 | 3.25 | 4.72 | 5.01 | 5.09 | 5.12 |
| 4 | 3.78 | 5.00 | 5.21 | 5.29 | 5.32 |
| 5 | 4.41 | 5.17 | 5.33 | 5.44 | 5.47 |
| 6 | 4.77 | 5.27 | 5.43 | 5.55 | 5.57 |
| 7 | 4.97 | 5.35 | 5.51 | 5.64 | 5.66 |
| 8 | 5.10 | 5.42 | 5.58 | 5.72 | 5.73 |
| 9 | 5.20 | 5.48 | 5.64 | 5.80 | 5.80 |
| 10 | 5.27 | 5.55 | 5.69 | 5.86 | 5.86 |
| 20 | 5.73 | 5.92 | 6.10 | 6.42 | 6.44 |
| 30 | 6.05 | 6.26 | 6.50 | 7.25 | 7.45 |
| 40 | 6.33 | 6.54 | 6.89 | 8.55 | 8.57 |

TABLE 7-continued

Effect of magnesium hydroxide and calcium carbonate in combination on the pH of a solution of 0.1N HCl with a starting pH of 2.0.

| Time, min | 50.82 mg Mg(OH)$_2$ + 50.95 mg CaCO$_3$ | 50.47 mg Mg(OH)$_2$ + 80.55 mg CaCO$_3$ | 50.0 mg Mg(OH)$_2$ + 100.98 mg CaCO$_3$ | 71.09 mg Mg(OH)$_2$ + 100.71 mg CaCO$_3$ | 71.25 mg Mg(OH)$_2$ + 150.35 mg CaCO$_3$ |
|---|---|---|---|---|---|
| 50 | 6.60 | 6.84 | 7.51 | 8.82 | 8.65 |
| 60 | 6.85 | 7.20 | 8.22 | 8.82 | 8.65 |

Figure 8:
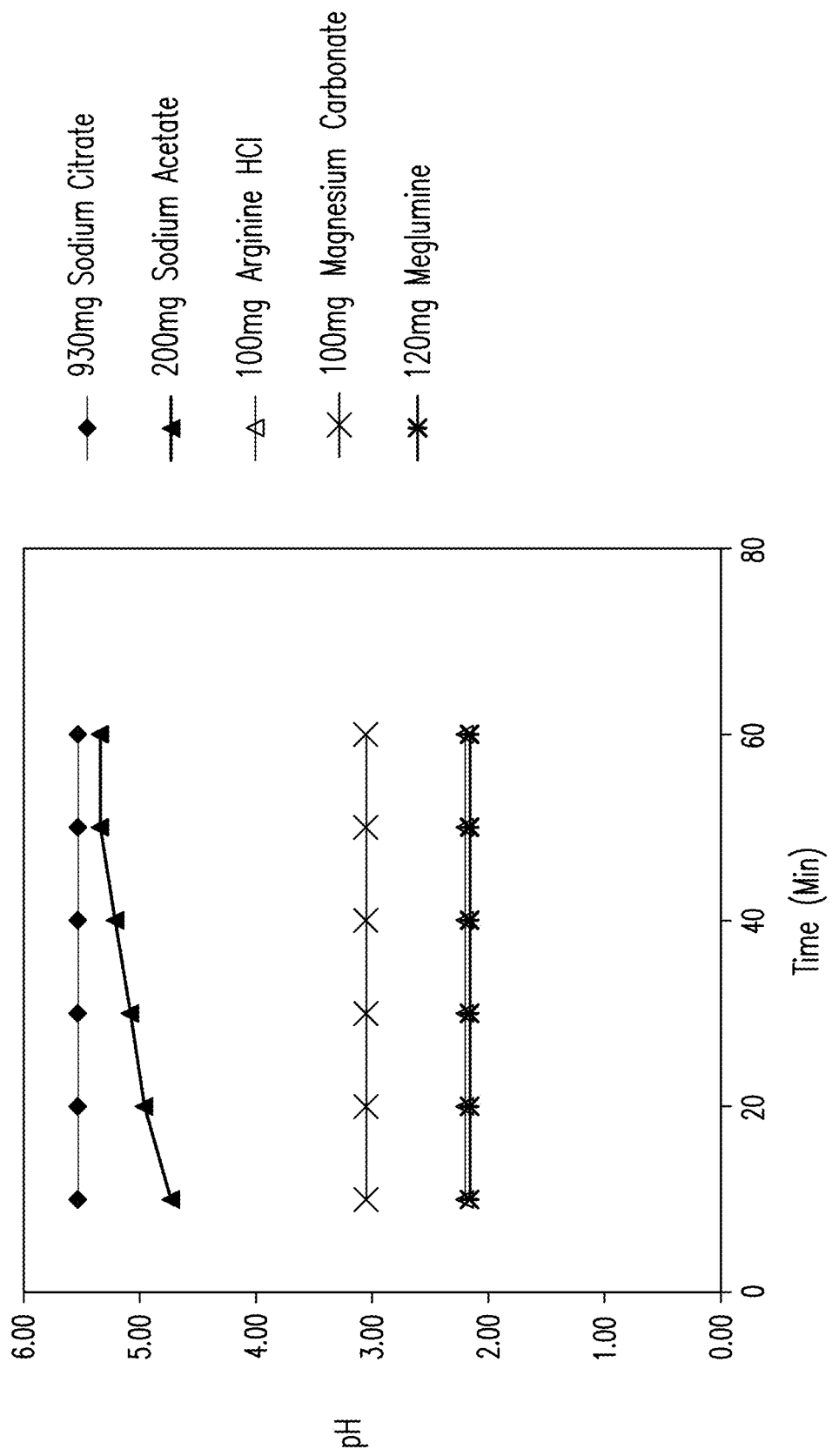
FIG. 8 shows the effects of 930 mg sodium citrate, 200 mg sodium acetate, 100 mg L-arginine-HCl, 100 mg magnesium carbonate, and 120 mg meglumine on the pH of an acidic solution over a 60 minute timecourse in 200 ml acidic solution.

Table 8 and FIG. 8 show the effects of 930 mg sodium citrate, 200 mg sodium acetate, 100 mg L-arginine-HCl, 100 mg magnesium carbonate, and 120 mg meglumine over a 60 minute timecourse in 200 ml solution. From this timecourse, it can be seen that all tested amounts were able to raise the pH of the solution above the 2.0 starting point, however, the sodium citrate and the sodium acetate were able to raise the pH to above 5.

TABLE 8

Effect of sodium citrate, sodium acetate, L-arginine-HCl, magnesium carbonate, and meglumine on the pH of a solution of 0.1N HCl with a starting pH of 2.0.

| Time, min | 930 mg Sodium Citrate | 200 mg Sodium Acetate | 100 mg Arginine HCl | 100 mg Magnesium Carbonate | 120 mg Meglumine |
|---|---|---|---|---|---|
| 10 | 5.53 | 4.73 | 2.20 | 3.05 | 2.16 |
| 20 | 5.53 | 4.96 | 2.20 | 3.05 | 2.16 |
| 30 | 5.53 | 5.08 | 2.20 | 3.05 | 2.16 |
| 40 | 5.53 | 5.21 | 2.20 | 3.05 | 2.16 |
| 50 | 5.53 | 5.34 | 2.20 | 3.05 | 2.16 |
| 60 | 5.53 | 5.34 | 2.20 | 3.05 | 2.16 |

Figure 9:
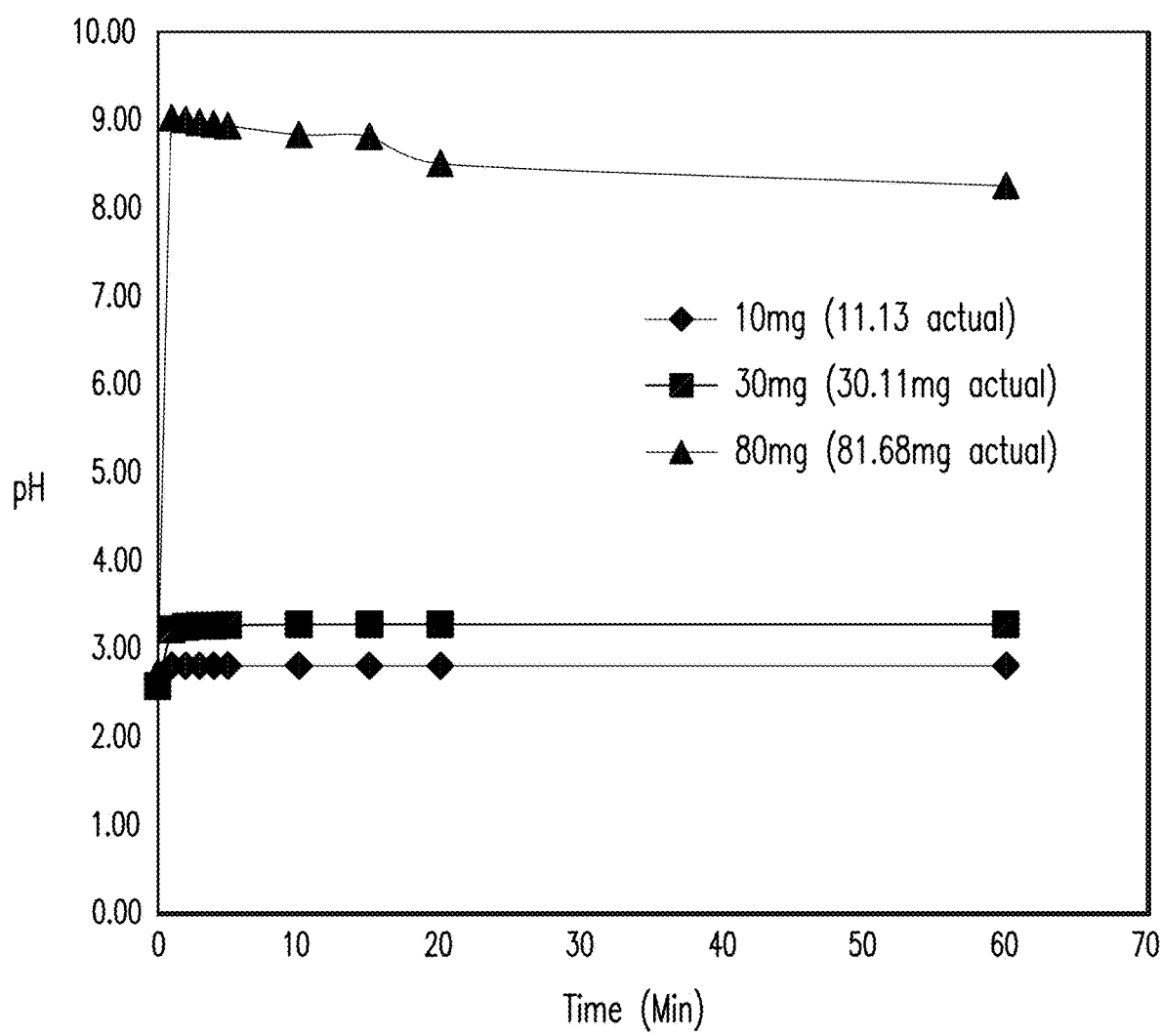
FIG. 9 shows the effects of sodium carbonate on the pH of an acidic solution over a 60 minute timecourse in amounts of 11.13-81.68 mg/200 ml acidic solution.

Table 9 and FIG. 9 show the effects of sodium carbonate over a 60 minute timecourse in amounts of 11.13-81.68 mg/200 ml solution. From this timecourse, it can be seen that all tested amount were able to raise the pH of the solution above the 2.0 starting point, and that 81.68 mg sodium carbonate was able to raise the pH of the 200 ml solution to above neutral.

TABLE 9

Effect of sodium carbonate on the pH of a solution of 0.1N HCl with a starting pH of 2.0.

| Time (mins) | 11.13 mg | 30.11 mg | 81.68 mg |
|---|---|---|---|
| 0 | 2.66 | 2.57 | 2.73 |
| 1 | 2.80 | 3.21 | 9.02 |
| 2 | 2.80 | 3.24 | 9 |
| 3 | 2.80 | 3.25 | 8.97 |
| 4 | 2.80 | 3.25 | 8.95 |
| 5 | 2.80 | 3.26 | 8.93 |
| 10 | 2.80 | 3.27 | 8.83 |
| 15 | 2.80 | 3.27 | 8.81 |
| 20 | 2.80 | 3.27 | 8.5 |
| 60 | 2.80 | 3.27 | 8.25 |

Figure 10:
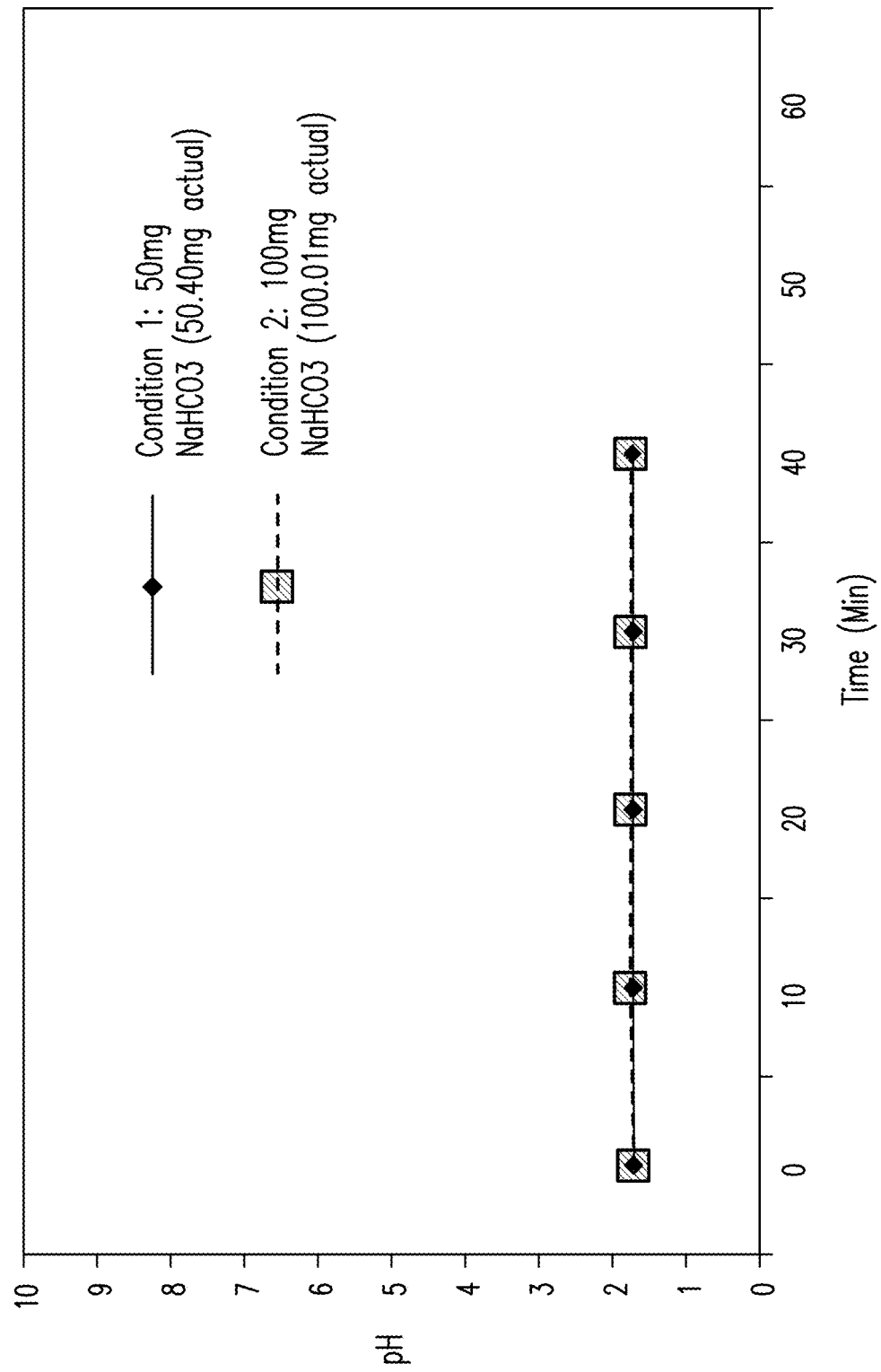
FIG. 10 shows the effects of sodium bicarbonate on the pH of an acidic solution over a 40 minute timecourse in amounts of 50 and 100 mg/200 ml acidic solution (overlap).

Table 10 and FIG. 10 show the effects of sodium bicarbonate over a 40 minute timecourse in amounts of 50 and 100 mg/200 ml solution. From this timecourse, it can be seen that neither tested amount was sufficient to raise the pH of the 200 ml starting solution.

TABLE 10

Effect of sodium bicarbonate on the pH of a solution of 0.1N HCl with a starting pH of 2.0.

| Time (mins) | 50 mg | 100 mg |
|---|---|---|
| 0 | 1.71 | 1.71 |
| 10 | 1.72 | 1.76 |
| 20 | 1.72 | 1.75 |
| 30 | 1.72 | 1.75 |
| 40 | 1.72 | 1.75 |

Figure 11:
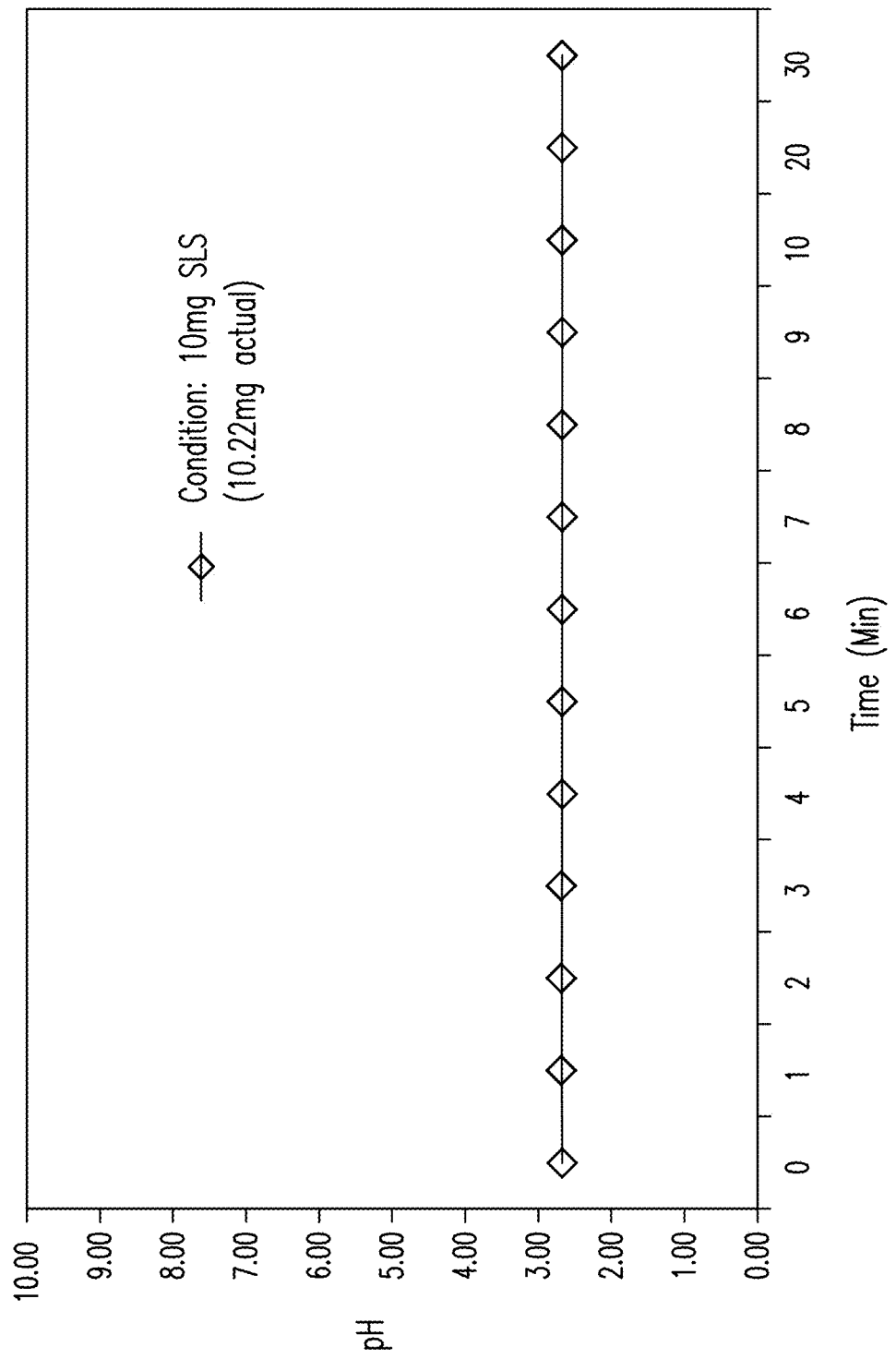
FIG. 11 shows the effect of 10 mg sodium lauryl sulfate on the pH of an acidic solution over a 30 minute timecourse in 200 ml acidic solution.

Table 11 and FIG. 11 show the effect of 10 mg sodium lauryl sulfate over a 30 minute timecourse in 200 ml acidic solution. From this timecourse, it can be seen that this amount of sodium lauryl sulfate was insufficient to substantially raise the pH of the solution beyond the 2.0 starting point.

TABLE 11

Effect of sodium lauryl sulfate on the pH of a solution of 0.1N HCl with a starting pH of 2.0.

| Time (mins) | 10 mg (10.22 mg actual) |
|---|---|
| 0 | 2.67 |
| 1 | 2.68 |
| 2 | 2.68 |
| 3 | 2.68 |
| 4 | 2.67 |
| 5 | 2.67 |
| 6 | 2.67 |
| 7 | 2.67 |
| 8 | 2.67 |
| 9 | 2.67 |
| 10 | 2.67 |
| 20 | 2.67 |
| 30 | 2.67 |

Figure 12:
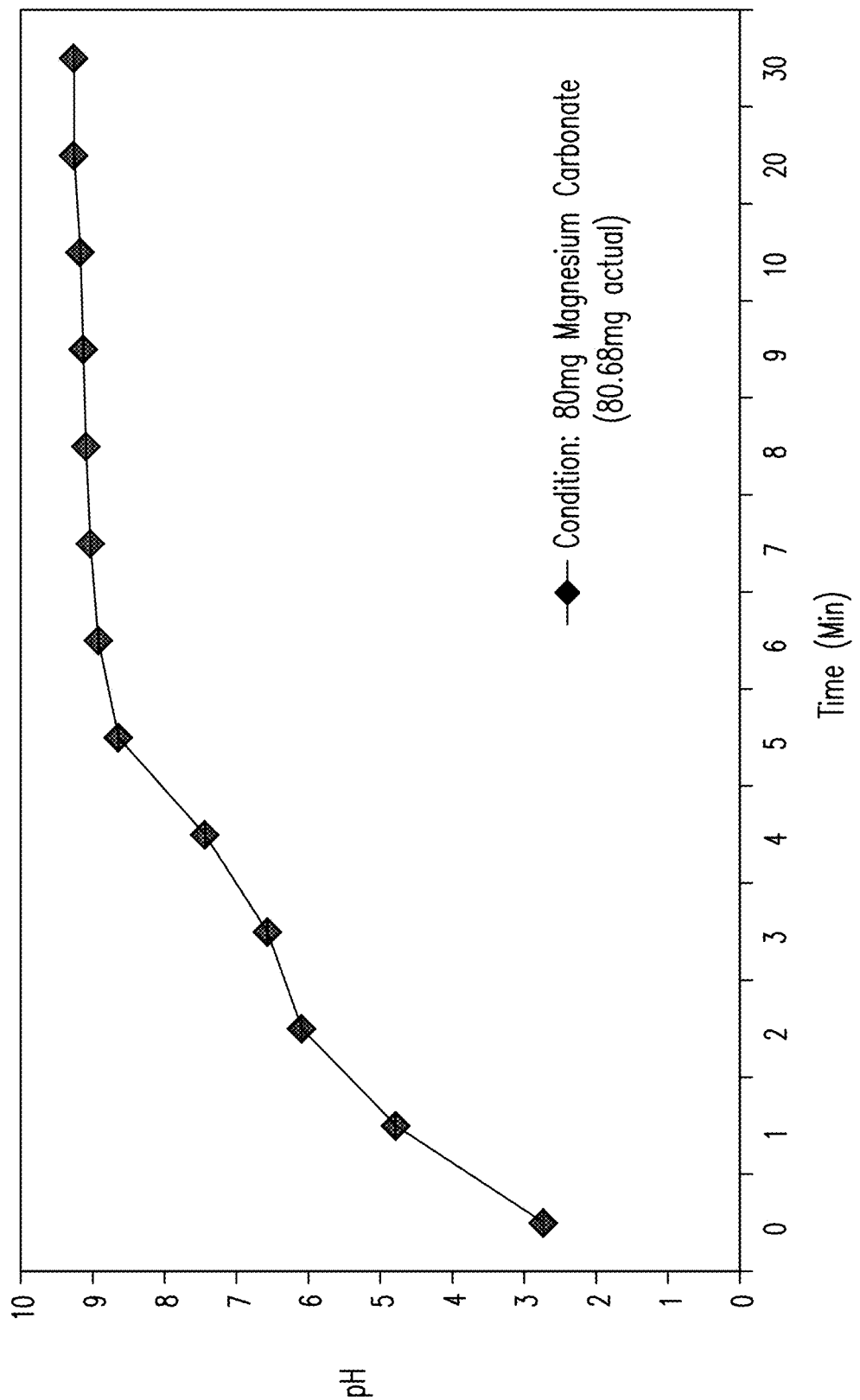
FIG. 12 shows the effect of 80 mg magnesium carbonate on the pH of an acidic solution over a 30 minute timecourse in 200 ml acidic solution.

Table 12 and FIG. 12 show the effect of 80 mg magnesium carbonate over a 30 minute timecourse in 200 ml acidic solution. From this timecourse, it can be seen that this amount of magnesium carbonate was sufficient to raise the pH of the solution to above 9.

TABLE 12

Effect of magnesium carbonate on the pH of a solution of 0.1N HCl with a starting pH of 2.0.

| Time (mins) | 80 mg |
|---|---|
| 0 | 2.73 |
| 1 | 4.78 |
| 2 | 6.09 |
| 3 | 6.57 |
| 4 | 7.44 |
| 5 | 8.64 |
| 6 | 8.92 |
| 7 | 9.03 |
| 8 | 9.09 |
| 9 | 9.13 |
| 10 | 9.17 |
| 20 | 9.26 |
| 30 | 9.26 |

Example 2. Preparation of Oxycodone HCl Overdose Resistant (ODR) 5 mg Tablets Formula for Core

| Ingredients | % w/w |
|---|---|
| Oxycodone HCl | 2.50 |
| Lactose | 68.50 |
| Crospovidone | 2.00 |
| Microcrystalline cellulose | 15.00 |
| Starch 1500 | 10.00 |
| Stearic Acid | 2.00 |

Formula for Acid Labile Coat*

| Ingredients | % w/w |
|---|---|
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*345 g of coating suspension was made and applied to 500 g of cores

Formula for Alkalinizing Coat*

| Ingredients | % w/w |
|---|---|
| Opadry White | 10.00 |
| Magnesium Hydroxide | 20.18 |
| Water | 69.82 |

*1000 g of coating suspension was made and applied to 500 g of acid labile-coated cores Processing Techniques Step 1a. Preparation of Granules for the Core:

All the ingredients with the exception of the stearic acid from the core formula were charged into a high shear granulator and dry mixed for less than 10 minutes. The dry mixed granules were discharged into a Paterson Kelly V-Blender. The stearic acid was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 200 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet Cores from Step 1b:

Tablets from Step 1b were charged into a rotating drum of a side vented automated tablet coater. The suspension from Step 2 was applied to the tablet cores obtained from Step 1b, using a peristaltic pump and spray gun. The suspension was dried as a film onto the tablets, using heated air drawn through the tablet bed from an inlet fan. A sufficient amount of the suspension was applied to form about 8 mg/cm$^2$ to about 12 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 3. Dissolution Test of Coated Tablets from Example 2

Figure 13A:
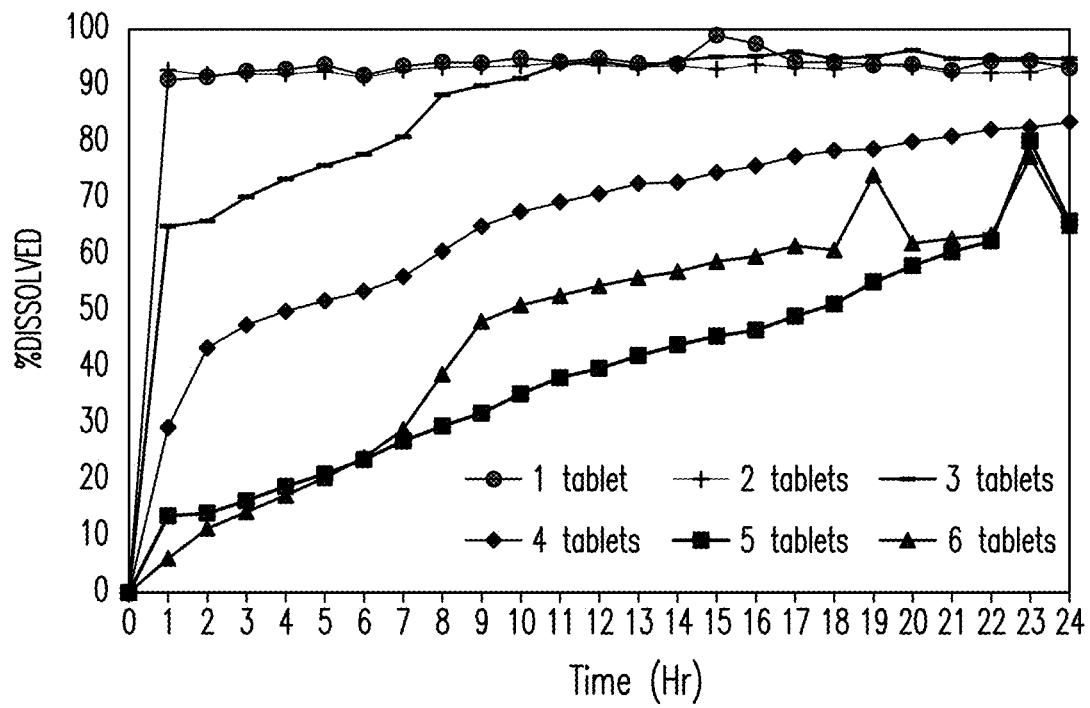
FIGS. 13A and 13B show that the dissolution of the tablets of Example 2 in an acidic solution is inversely proportional to the number of tablets added to the solution.
Figure 13B:
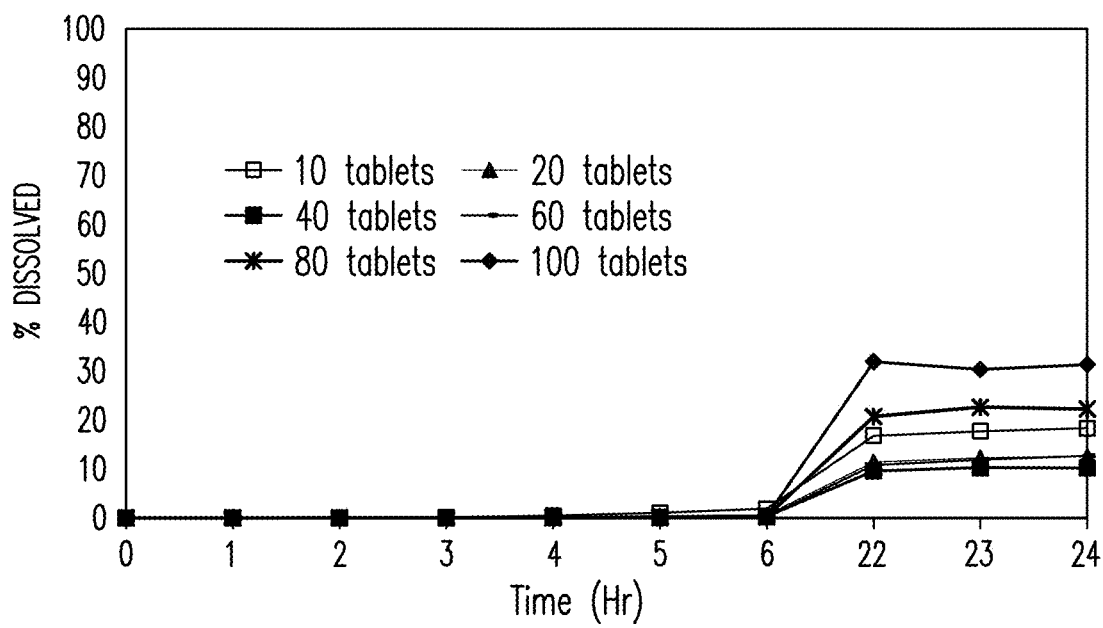
Figure 13C:
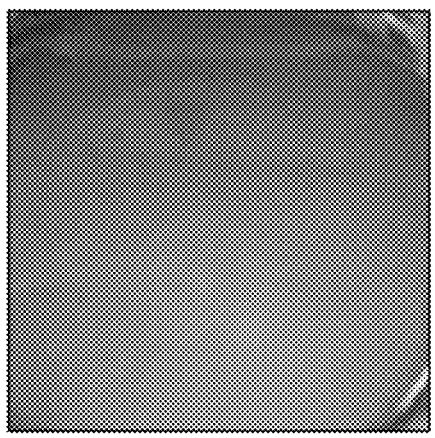
FIGS. 13C through 13H show the dissolution of the tablets of Example 2 in an acidic solution.
Figure 13D:
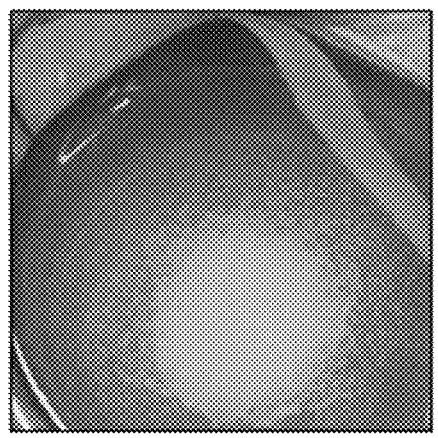
Figure 13E:
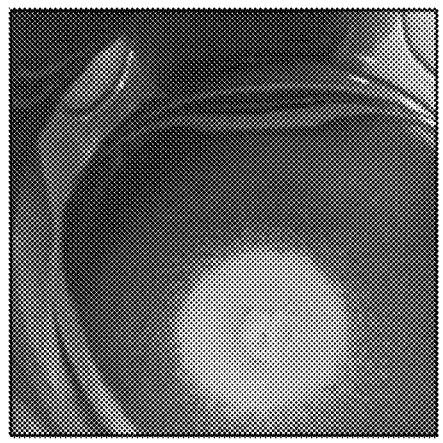
Figure 13F:
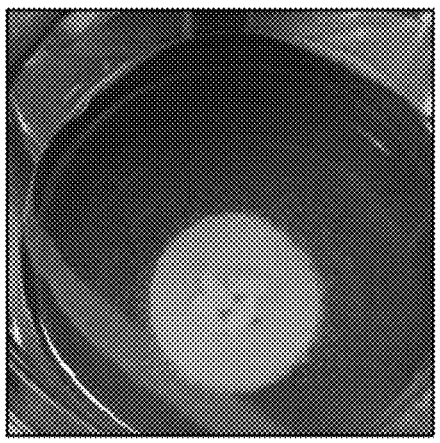
Figure 13G:
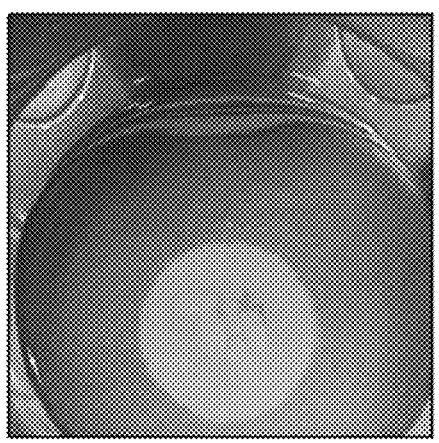
Figure 13H:
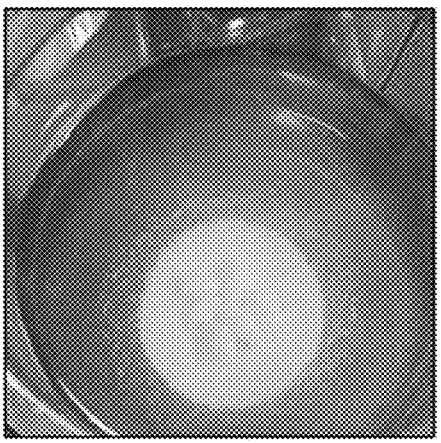

Tablets from Example 2 were placed into 500 ml of a 0.01 N HCl solution and were agitated with paddles at 100 rpm for various times at 37° C. Table 13 and corresponding FIGS. 13A and 13B show that increasing numbers of tablets in the solution led to decreased dissolution of the tablets, both in terms of time and extent of total dissolution. FIGS. 13C and 13D show images of 1 and 2 tablets, respectively, dissolving completely after 1 hour. FIGS. 13E, 13F, 13G, and 13H show images of the 3-6 tablet experiments, respectively, with the tablets remaining mostly intact or completely intact (other than the alkalinizing coat) after 24 hours.

It should be noted that at the longer ends of the time-course, e.g., from 22-24 hours, the tablets began to disintegrate from the mechanical effects of the paddles and tablets hitting one another. Therefore, the extent of dissolution seen in the higher number tablet experiments (for example, from 10-100 tablets) appears to be an artefact and much lower dissolution would be expected in a system without paddles (e.g., in the stomach).

TABLE 13

Comparative dissolution of different quantities of tablets made according to Example 2 in 500 ml 0.01N HCl (pH 2.0).

Number of tablets in dissolution vessel and percent dissolved

| Time (hrs) | 1 tab | 2 tabs | 3 tabs | 4 tabs | 5 tabs | 6 tabs | 10 tabs | 20 tabs | 40 tabs | 60 tabs | 80 tabs | 100 tabs |
|---|---|---|---|---|---|---|---|---|---|---|---|---|
| 0 | 0 | 0 | 0 | 0 | 0 | 0 | 0 | 0 | 0 | 0 | 0 | 0 |
| 1 | 91 | 93 | 65 | 29 | 14 | 6 | 0 | 0 | 0 | 0 | 0 | 0 |
| 2 | 91 | 92 | 66 | 43 | 14 | 11 | 0 | 0 | 0 | 0 | 0 | 0 |
| 3 | 93 | 92 | 70 | 47 | 16 | 14 | 0 | 0 | 0 | 0 | 0 | 0 |
| 4 | 93 | 92 | 73 | 50 | 19 | 17 | 0 | 0 | 0 | 0 | 0 | 0 |
| 5 | 94 | 93 | 76 | 52 | 21 | 20 | 1 | 0 | 0 | 0 | 0 | 0 |
| 6 | 92 | 91 | 78 | 53 | 24 | 24 | 2 | 1 | 0 | 0 | 0 | 0 |
| 22 | 94 | 92 | 95 | 82 | 62 | 63 | 17 | 11 | 10 | 11 | 21 | 32 |
| 23 | 94 | 92 | 95 | 83 | 80 | 77 | 18 | 12 | 10 | 12 | 23 | 30 |
| 24 | 93 | 94 | 95 | 84 | 66 | 65 | 18 | 13 | 10 | 13 | 22 | 31 |
| Starting pH | 2.0 | 2.0 | 2.0 | 2.0 | 2.0 | 2.0 | 2.0 | 2.0 | 2.0 | 2.0 | 2.0 | 2.0 |
| Ending pH |  |  |  |  |  |  | 9.25 | 9.31 | 9.30 | 9.31 | 9.28 | 9.27 |

Example 4. Preparation of Oxycodone HCl Overdose+Insufflation Resistant (ODIR) 5 mg Tablets Formula for Core

| Ingredients | % w/w |
|---|---|
| Oxycodone HCl | 2.50 |
| Lactose | 38.00 |
| Sodium Lauryl Sulfate | 30.50 |
| Crospovidone | 2.00 |
| Microcrystalline cellulose | 15.00 |
| Starch 1500 | 10.00 |
| Stearic Acid | 2.00 |

Formula for Acid Labile Coat*

| Ingredients | % w/w |
|---|---|
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*687.82 g of coating suspension was made and applied to 500 g of cores

Formula for Alkalinizing Coat*

| Ingredients | % w/w |
|---|---|
| Opadry White | 10.00 |
| Magnesium Hydroxide | 20.18 |
| Water | 69.82 |

*1000 g of coating suspension was made and applied to 500 g of acid labile-coated cores Processing Techniques Step 1a. Preparation of Granules for the Core:

All the ingredients with the exception of the stearic acid from the core formula were charged into a high shear granulator and dry mixed for less than 10 minutes. The dry mixed granules were discharged into a Paterson Kelly V-Blender. The stearic acid was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 200 mg (a Manesty tablet press with 16 stations was used). Granules from Step1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet Cores from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 19 mg/cm$^2$ to about 25 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 5. Dissolution Test of Coated Tablets from Example 4

Figure 14A:
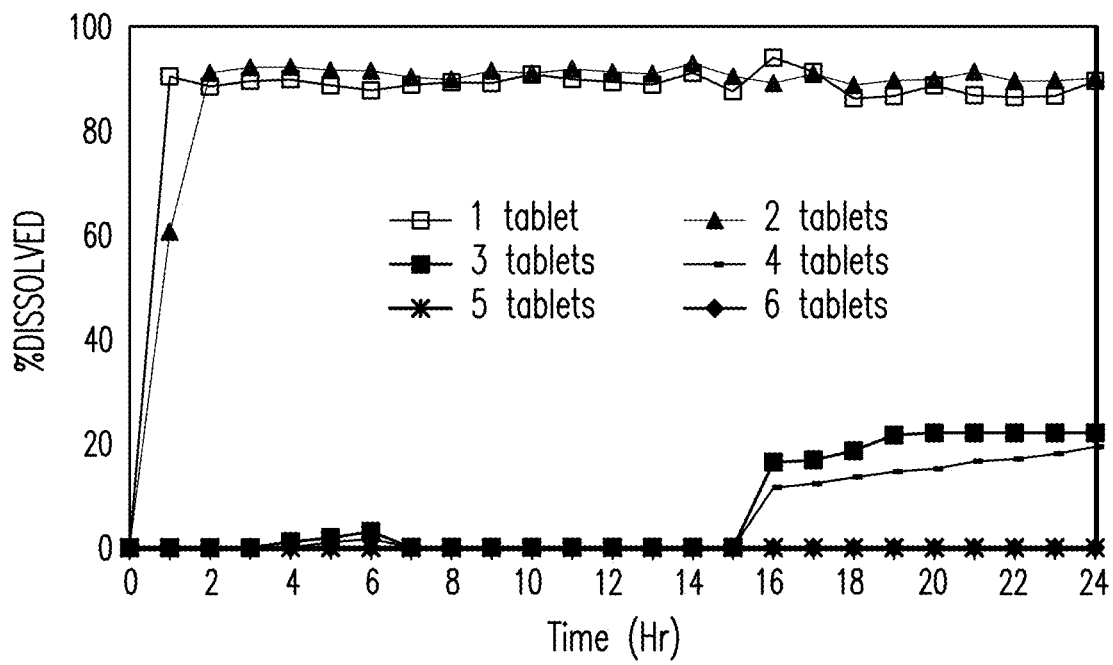
FIGS. 14A and 14B show that the dissolution of the tablets of Example 4 in an acidic solution is inversely proportional to the number of tablets added to the solution.
Figure 14B:
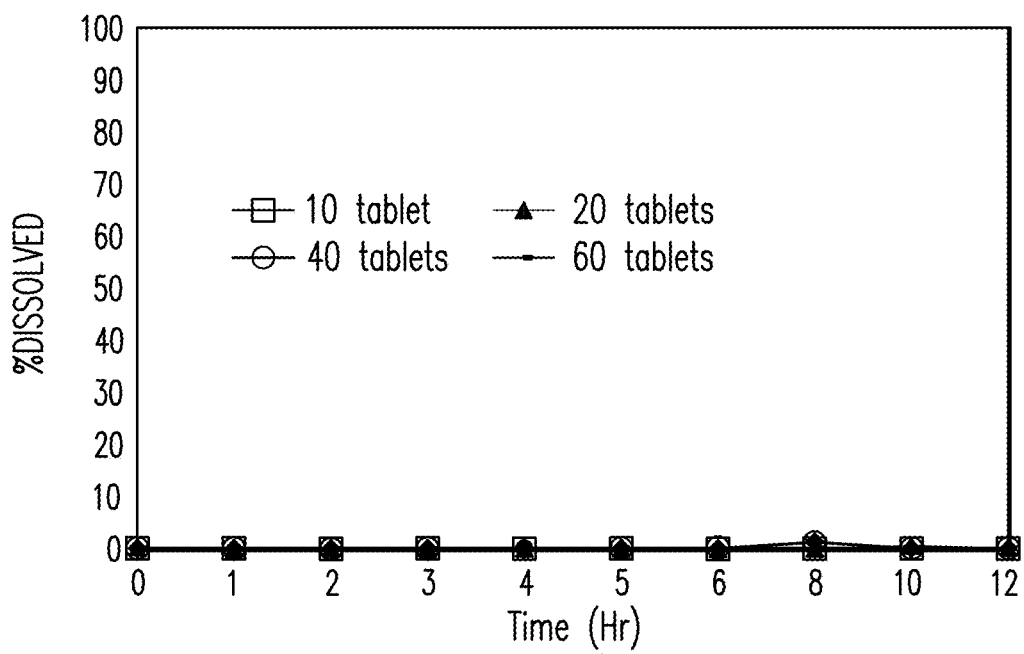
Figure 14C:
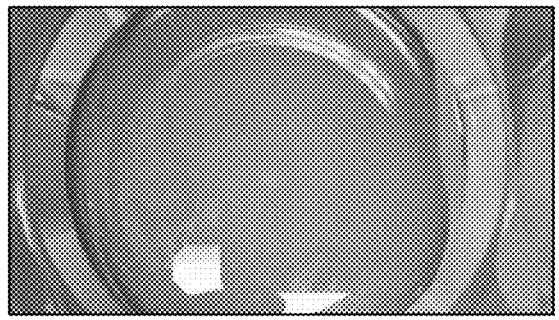
FIGS. 14C through 14H show the dissolution of the tablets of Example 4 in an acidic solution.
Figure 14D:
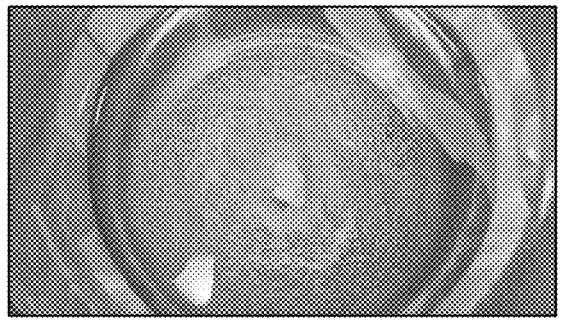
Figure 14E:
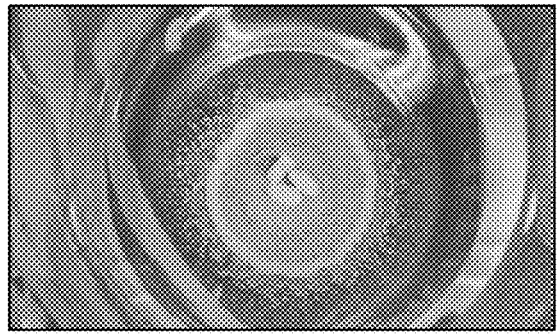
Figure 14F:
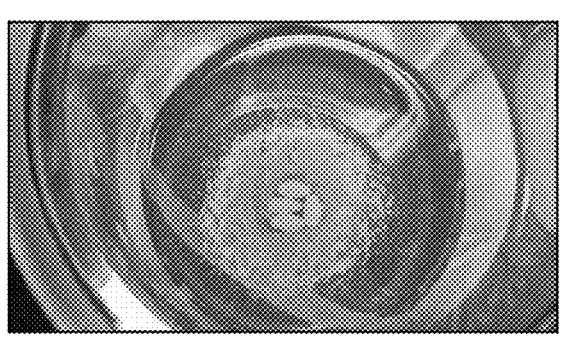
Figure 14G:
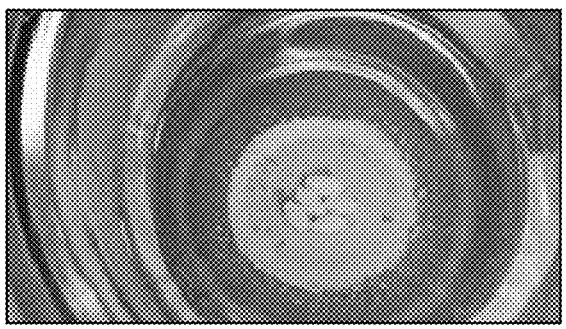
Figure 14H:
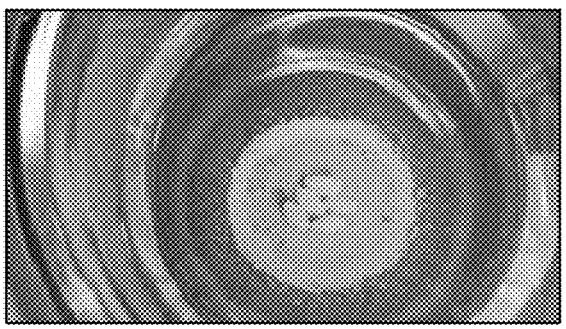

Tablets from Example 4 were placed into 500 ml of a 0.01 N HCl solution and were agitated with paddles at 100 rpm for various times at 37° C. Table 14 and corresponding FIGS. 14A and 14B show that increasing numbers of tablets in the solution led to decreased dissolution of the tablets, both in terms of time and extent of total dissolution. FIGS. 14C and 14D show images of 1 and 2 tablets, respectively, dissolving completely after 1 hour. FIGS. 14E, 14F, 14G, and 14H show images of the 3-6 tablet experiments, respectively, with the tablets remaining mostly intact or completely intact (other than the alkalinizing coat) after 24 hours.

It should be noted that at the longer ends of the time-course, e.g., from 22-24 hours, the tablets began to disintegrate from the mechanical effects of the paddles and tablets hitting one another. Therefore, the extent of dissolution seen in the higher number tablet experiments (for example, from 10-100 tablets) appears to be an artefact and much lower dissolution would be expected in a system without paddles (e.g., in the stomach). The thicker acid labile coating on these tablets as compared to those of Example 2 appears to have protected them somewhat from the mechanical disintegration caused by the paddles and other tablets hitting one another.

| Formula for the Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*1375.64 g of coating suspension was made and applied to 500 g of tablets

| Formula for Alkalinizing Coat* | |
|---|---|
| Ingredients | % w/w |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the stearic acid from the core formula were charged into a high shear granulator and dry mixed for less than 10 minutes. The dry mixed granules were discharged into a Paterson Kelly V-Blender. The stearic acid was then added to the V-Blender. The granules were blended for less than 10 minutes.

TABLE 14

Comparative dissolution of different quantities of tablets made according to Example 2 in 500 ml 0.01N HCl (pH 2.0).

| | Number of tablets in dissolution vessel and percent dissolved | | | | | | | | | | |
|---|---|---|---|---|---|---|---|---|---|---|---|
| Time (hrs) | 1 tab | 2 tabs | 3 tabs | 4 tabs | 5 tabs | 6 tabs | 10 tabs | 20 tabs | 40 tabs | 60 tabs | 80 tabs |
| 0 | 0 | 0 | 0 | 0 | 0 | 0 | 0 | 0 | 0 | 0 | 0 |
| 1 | 90 | 61 | 0 | 0 | 0 | 0 | 0 | 0 | 0 | 0 | 0 |
| 2 | 88 | 91 | 0 | 0 | 0 | 0 | 0 | 0 | 0 | 0 | 0 |
| 3 | 90 | 92 | 0 | 0 | 0 | 0 | 0 | 0 | 0 | 0 | 0 |
| 4 | 90 | 92 | 1 | 0 | 0 | 0 | 0 | 0 | 0 | 0 | 0 |
| 5 | 89 | 92 | 2 | 1 | 0 | 0 | 0 | 0 | 0 | 0 | 0 |
| 6 | 88 | 91 | 3 | 2 | 0 | 0 | 0 | 0 | 0 | 0 | 0 |
| 22 | 86 | 90 | 22 | 17 | 0 | 0 | 17 | 11 | 10 | 1 | 1 |
| 23 | 87 | 90 | 22 | 18 | 0 | 0 | 18 | 12 | 10 | 1.2 | 1.2 |
| 24 | 90 | 90 | 22 | 19 | 0 | 0 | 18 | 13 | 10 | 1.5 | 1.4 |
| Starting pH | 2.0 | 2.0 | 2.0 | 2.0 | 2.0 | 2.0 | 2.0 | 2.0 | 2.0 | 2.0 | 2.0 |
| Ending pH | 2.5 | 8.01 | 9.08 | 9.11 | 9.19 | 9.28 | 9.24 | 9.24 | 9.26 | 9.27 | 9.26 |

Example 6. Preparation of Oxycodone HCl Overdose Resistant (ODR) 5 mg Tablets

| Formula for Core | |
|---|---|
| Ingredients | % w/w |
| Oxycodone HCl | 2.50 |
| Lactose | 68.50 |
| Crospovidone | 2.00 |
| Microcrystalline cellulose | 15.00 |
| Starch 1500 | 10.00 |
| Stearic Acid | 2.00 |

Step 1b. Preparation of the Core (Immediate Release Tablets):

The cores are tablets made from the granules prepared in Step 1a. A rotary press was set-up to produce capsule shaped tablets each weighing about 200 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

The thicker acid labile coating on these tablets as compared to those of Examples 2 and 4 appears to have protected them from the mechanical disintegration caused by the paddles and other tablets hitting one another, as even after 100 tablets have been mixed for 24 hours, there was no dissolution of the tablets.

TABLE 15

Comparative dissolution of different quantities of tablets made according to Example 2 in 500 ml 0.01N HCl (pH 2.0).

| | Number of tablets in dissolution vessel and percent dissolved | | | | | | | | | | | |
|---|---|---|---|---|---|---|---|---|---|---|---|---|
| Time (hrs) | 1 tab | 2 tabs | 3 tabs | 4 tabs | 5 tabs | 6 tabs | 10 tabs | 20 tabs | 40 tabs | 60 tabs | 80 tabs | 100 tabs |
| 0 | 0 | 0 | 0 | 0 | 0 | 0 | 0 | 0 | 0 | 0 | 0 | 0 |
| 1 | 83 | 3 | 0 | 0 | 0 | 0 | 0 | 0 | 0 | 0 | 0 | 0 |
| 2 | 92 | 4 | 0 | 0 | 0 | 0 | 0 | 0 | 0 | 0 | 0 | 0 |
| 3 | 93 | 4 | 0 | 0 | 0 | 0 | 0 | 0 | 0 | 0 | 0 | 0 |
| 4 | 92 | 4 | 0 | 0 | 0 | 0 | 0 | 0 | 0 | 0 | 0 | 0 |
| 5 | 91 | 4 | 0 | 0 | 0 | 0 | 0 | 0 | 0 | 0 | 0 | 0 |
| 6 | 91 | 4 | 0 | 0 | 0 | 0 | 0 | 0 | 0 | 0 | 0 | 0 |
| 22 | 92 | 16 | 0 | 0 | 0 | 0 | 0 | 0 | 0 | 0 | 0 | 0 |
| 23 | 91 | 18 | 0 | 0 | 0 | 0 | 0 | 0 | 0 | 0 | 0 | 0 |
| 24 | 91 | 19 | 0 | 0 | 0 | 0 | 0 | 0 | 0 | 0 | 0 | 0 |
| Starting pH | 2.0 | 2.0 | 2.0 | 2.0 | 2.0 | 2.0 | 2.0 | 2.0 | 2.0 | 2.0 | 2.0 | 2.0 |
| Ending pH | 2.86 | 9.07 | 9.20 | 9.27 | 9.28 | 9.26 | 9.19 | 9.25 | 9.28 | 9.25 | 9.24 | 9.25 |

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 40 mg/cm² to about 50 mg/cm² of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 7. Dissolution Test of Coated Tablets from Example 6

Figure 15A:
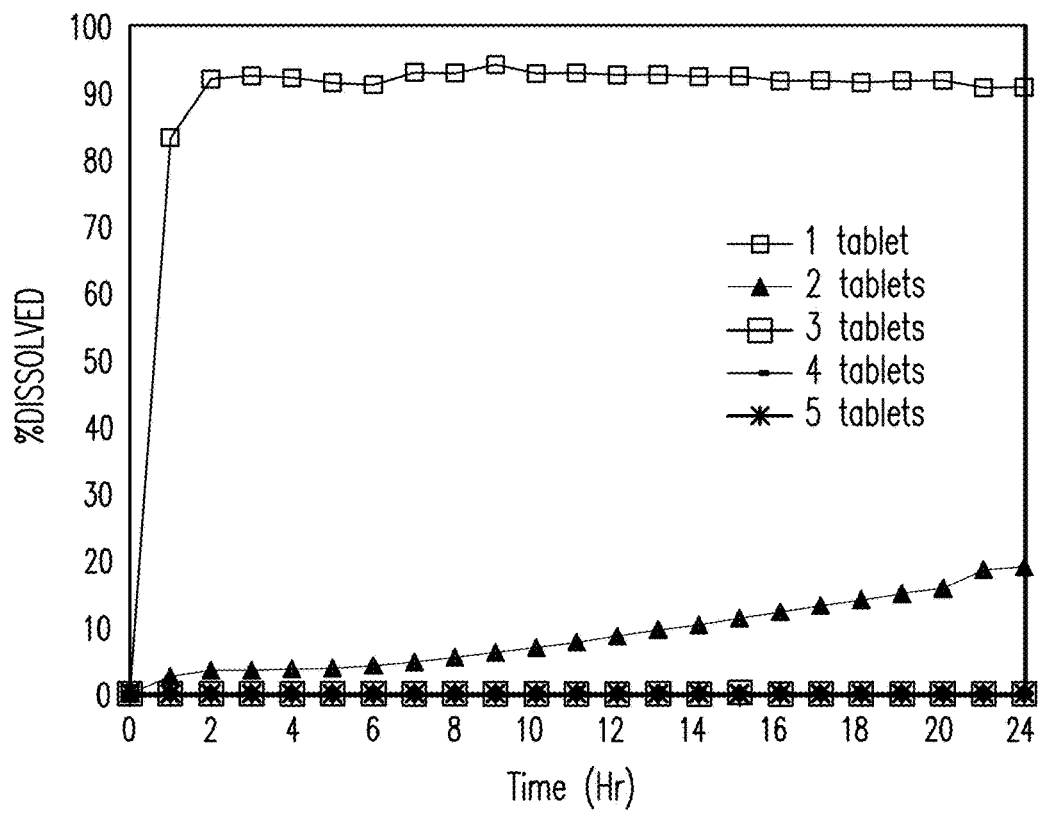
FIGS. 15A and 15B show that the dissolution of the tablets of Example 6 in an acidic solution is inversely proportional to the number of tablets added to the solution.
Figure 15B:
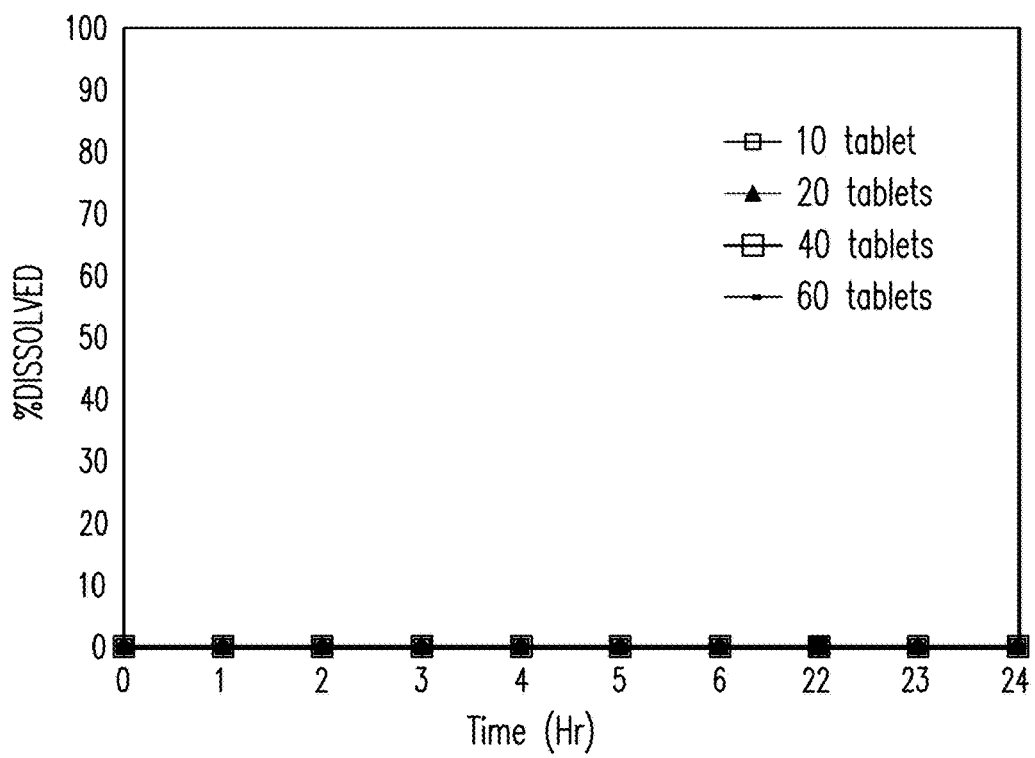
Figure 15C:
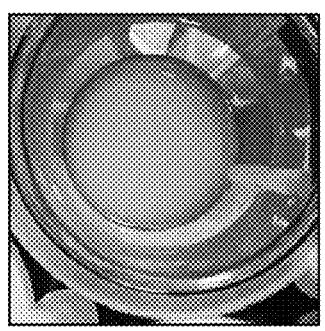
FIGS. 15C through 15K show the dissolution of the tablets of Example 6 in an acidic solution.
Figure 15D:
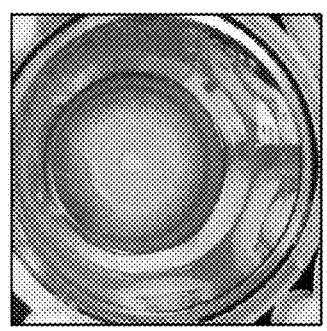
Figure 15E:
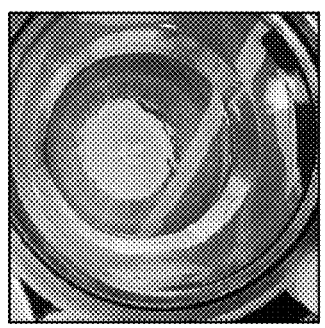
Figure 15F:
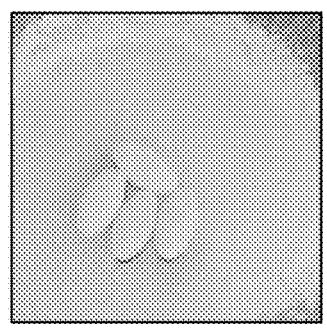
Figure 15G:
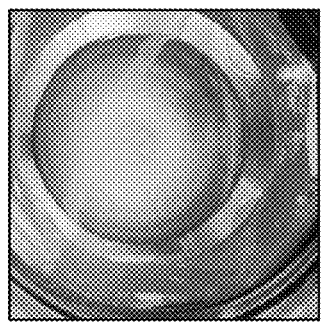
Figure 15H:
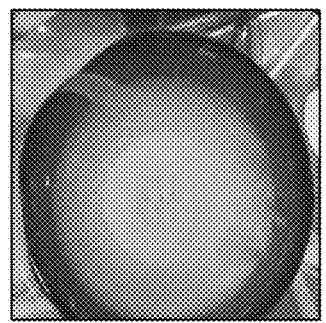
Figure 15I:
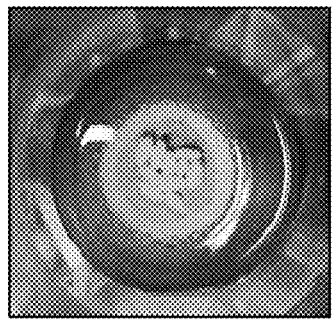
Figure 15J:
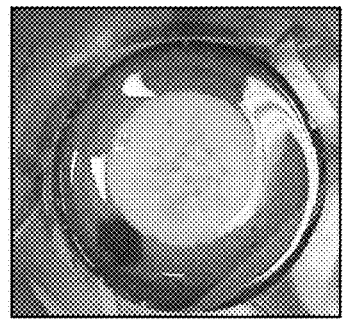
Figure 15K:
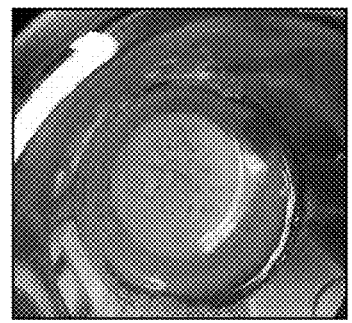

Tablets from Example 6 were placed into 500 ml of a 0.01 N HCl solution and were agitated with paddles at 100 rpm for various times at 37° C. Table 15 and corresponding FIGS. 15A and 15B show that increasing numbers of tablets in the solution led to decreased dissolution of the tablets, both in terms of time and extent of total dissolution. FIGS. 15C and 15D show images of 1 and 2 tablets, respectively, dissolving completely after 1 hour. FIGS. 15E, 15F, 15G, 15H, 15I, 15J, and 15K show images of the 3-50 tablet experiments, respectively, with the tablets remaining intact (other than the alkalinizing coat) after 24 hours.

Figure 15L:
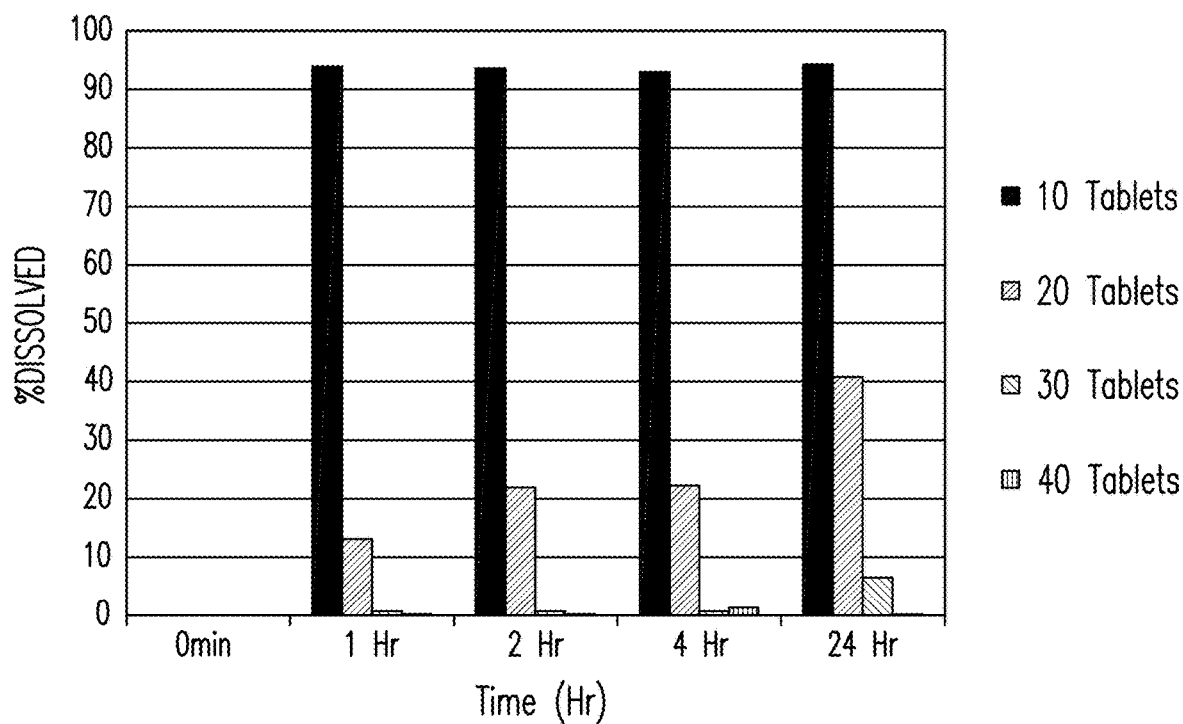
FIG. 15L is a graph showing the rate and extent of dissolution of 10, 20, 30, and 40 tablets in the acidic solution.

Tablets from Example 6 were next placed into 300 ml of a 0.1 N HCl solution with a pH of 1.0 and were agitated with paddles at 100 rpm for various times at 37° C. FIG. 15L shows that increasing numbers of tablets in the solution led to decreased dissolution of the tablets, both in terms of time and extent of total dissolution, as measured by HPLC.

Figure 15M:
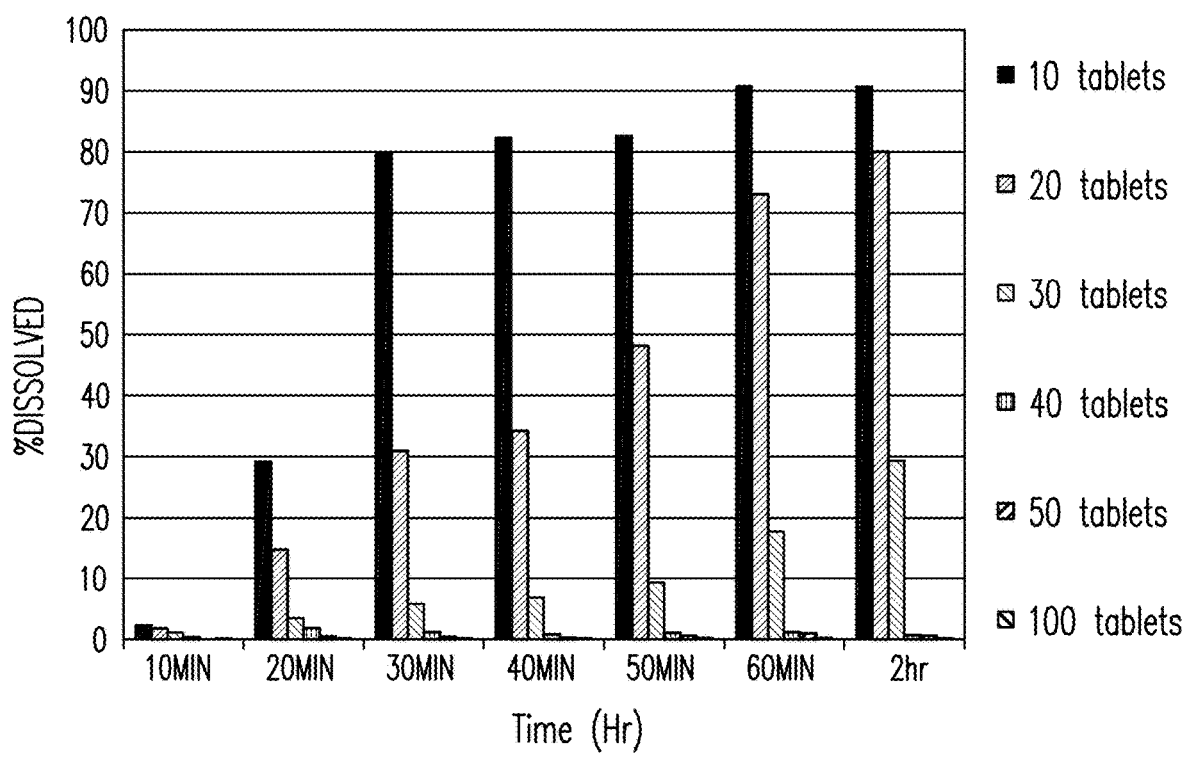
FIG. 15M is a graph showing the rate and extent of dissolution of 10, 20, 30, 40, 50, and 100 tablets in the acidic solution.

Tablets from Example 6 were next placed into 500 ml of a 0.1 N HCl solution with a pH of 1.0 and were agitated with paddles at 100 rpm for various times at 37° C. FIG. 15M shows that increasing numbers of tablets in the solution led to decreased dissolution of the tablets, both in terms of time and extent of total dissolution, as measured by HPLC.

Example 8. Comparative Dissolution Test of Coated Tablets from Examples 2, 4, and 6

Figure 16A:
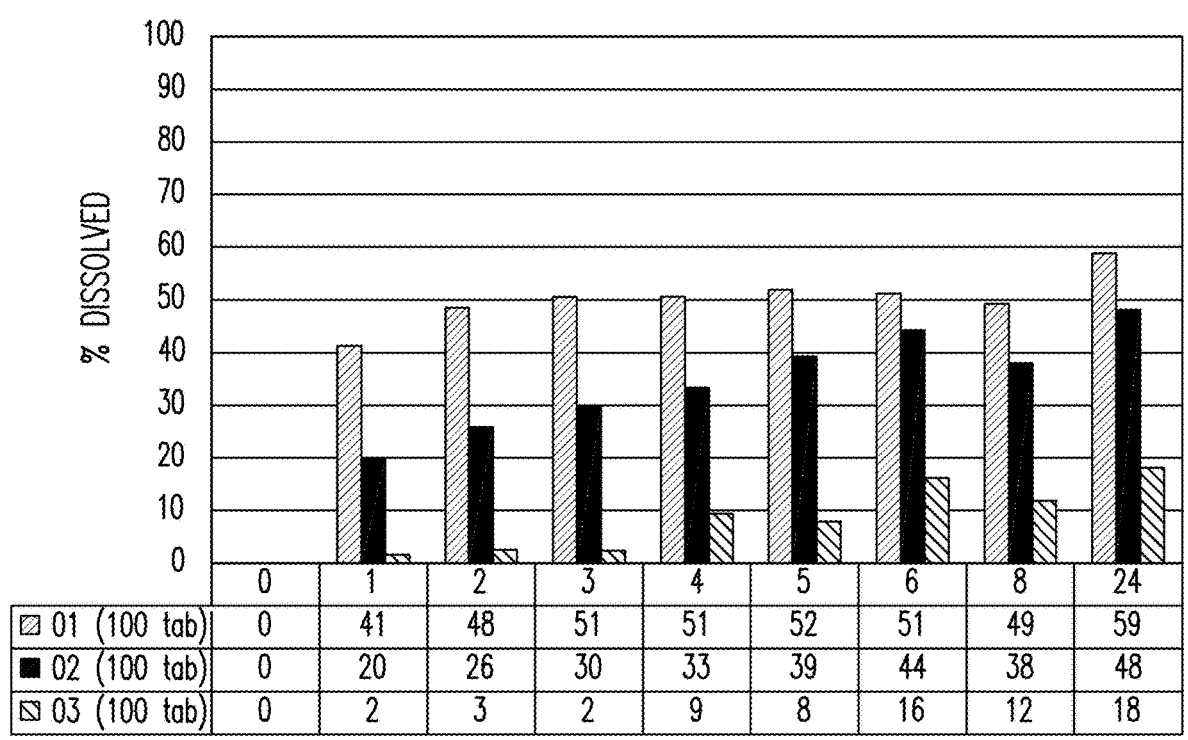
FIGS. 16A and 16B show a comparison of drug release between tablets of Examples 2, 4, and 6 were added to an acidic solution.
Figure 16B:
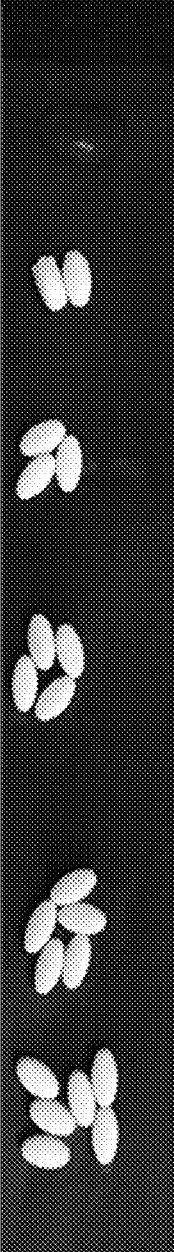

One hundred tablets from each of Examples 2, 4, and 6 were placed into 900 ml of a 0.1 N HCl solution with a pH of 1.0 and were agitated with paddles at 100 rpm for various times at 37° C. HPLC measurements were taken at each time point to determine how much of the oxycodone was released. The results are shown in FIGS. 16A and 16B, where it is evident that the tablets of Example 6 showed the lowest release, followed by the tablets of Example 4, then Example 2.

Example 9. Oxycodone HCl+Acetaminophen Overdose Resistant (ODR) 5/325 mg Tablets

| Formula for Core | |
|---|---|
| Ingredients | % w/w |
| Oxycodone HCl | 1.00 |
| Acetaminophen | 65.00 |
| Crospovidone | 5.00 |
| Silicone dioxide | 1.00 |
| Microcrystalline cellulose | 16.00 |

-continued

Formula for Core

| Ingredients | % w/w |
|---|---|
| Starch 1500 | 10.00 |
| Stearic Acid | 2.00 |

Formula for Acid Labile Coat*

| Ingredients | % w/w |
|---|---|
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*687.82 g of coating suspension was made and applied to 500 g of tablets

Formula for Alkalinizing layer (coat)

| Ingredients | % w/w |
|---|---|
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the stearic acid from the core formula were charged into a high shear granulator and dry mixed for less than 10 minutes. The dry mixed granules were discharged into a Paterson Kelly V-Blender. The stearic acid was then added to the V-Blender. The granules were blended for less than 10 minutes.

Step 1b. Preparation of the Core (Immediate Release Tablets):

The cores are tablets made from the granules prepared in Step1a. A rotary press was set-up to produce capsule shaped tablets each weighing about 500 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 19 mg/cm$^2$ to about 25 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 10. Oxycodone HCl+Aspirin Overdose Resistant (ODR) 5/325 mg Tablets

Formula for Core

| Ingredients | % w/w |
|---|---|
| Oxycodone HCl | 1.25 |
| Aspirin USP | 81.25 |
| Microcrystalline cellulose | 15.50 |
| Stearic Acid | 2.00 |

Formula for Acid Labile Coat*

| Ingredients | % w/w |
|---|---|
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*687.82 g of coating suspension was made and applied to 500 g of tablets

Formula for Alkalinizing Coat*

| Ingredients | % w/w |
|---|---|
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the stearic acid from the core formula were charged into a high shear granulator and dry mixed for less than 10 minutes. The dry mixed granules were discharged into a Paterson Kelly V-Blender. The stearic acid was then added to the V-Blender. The granules were blended for less than 10 minutes.

Step 1b. Preparation of the Core (Immediate Release Tablets):

The cores are tablets made from the granules prepared in Step1a. A rotary press was set-up to produce capsule shaped tablets each weighing about 400 mg (a Manesty tablet press with 16 stations was used). Granules from Step1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 19 mg/cm$^2$ to about 25 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 11. Oxycodone HCl+Ibuprophen Overdose Resistant (ODR) 5/400 mg Tablets

Formula for Core

| Ingredients | % w/w |
| --- | --- |
| Oxycodone HCl USP | 0.83 |
| Ibuprofen USP | 66.67 |
| Crospovidone | 4.00 |
| Silicone dioxide | 1.00 |
| Microcrystalline cellulose | 15.33 |
| Povidone K90 | 2.00 |
| Starch 1500 | 7.17 |
| Stearic Acid | 1.50 |
| Calcium stearate | 1.50 |

Formula for Acid Labile Coat*

| Ingredients | % w/w |
| --- | --- |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*687.82 g of coating suspension was made and applied to 500 g of tablets

Formula for Alkalinizing Coat*

| Ingredients | % w/w |
| --- | --- |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of povidone, stearic acid and the calcium stearate from the core formula were charged into a high shear granulator and dry mixed for less than 10 minutes. The dry mixed granules were granulated using a 10% povidone solution. The wet granules were dried in an oven at 60° C. to a loss of drying of less than 2%. The dried granules were passed through a co-mill fitted with screen sieves with holes of size 1000 microns and discharged into a Paterson Kelly V-Blender. The stearic acid and calcium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 600 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 19 mg/cm$^2$ to about 25 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 12. Diazepam Overdose Resistant (ODR) 5 mg Tablets

| Formula for Core | |
|---|---|
| Ingredients | % w/w |
| Diazepam | 2.50 |
| Lactose | 70.00 |
| Microcrystalline cellulose | 15.00 |
| Starch 1500 | 10.00 |
| Calcium stearate | 2.50 |

| Formula for Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*345 g of coating suspension was made and applied to 500 g of tablets

| Formula for Alkalinizing Coat* | |
|---|---|
| Ingredients | % w/w |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the calcium stearate from the core formula were charged into a high shear granulator and dry mixed for less than 10 minutes. The dry mixed granules were discharged into a Paterson Kelly V-Blender. The calcium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 200 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 8 mg/cm$^2$ to about 12 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 13. Phenobarbital Overdose Resistant (ODR) 30 mg Tablets

| Formula for Core | |
|---|---|
| Ingredients | % w/w |
| Phenobarbital | 7.50 |
| Lactose | 66.00 |
| Microcrystalline cellulose | 15.00 |
| Starch 1500 | 10.00 |
| Magnesium stearate | 1.50 |

| Formula for Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |

-continued

Formula for Acid Labile Coat*

| Ingredients | % w/w |
|---|---|
| Simethicone Emulsion 30% | 2.81 |
| Water | 81.63 |

*345 g of coating suspension was made and applied to 500 g of tablets

Formula for Alkalinizing Coat*

| Ingredients | % w/w |
|---|---|
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the magnesium stearate from the core formula were charged into a high shear granulator and dry mixed for less than 10 minutes. The dry mixed granules were discharged into a Paterson Kelly V-Blender. The magnesium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 400 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 8 mg/cm$^2$ to about 12 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 14. Oxycodone HCl Overdose+Insufflation Resistant (ODIR) 5 mg Tablets

Formula for Core

| Ingredients | % w/w |
|---|---|
| Oxycodone HCl | 1.67 |
| Lactose | 38.50 |
| Sodium Lauryl Sulfate | 26.66 |
| Capsaicin | 3.00 |
| Crospovidone | 2.00 |
| Microcrystalline cellulose | 16.17 |
| Starch 1500 | 10.00 |
| Stearic Acid | 2.00 |

Formula for Acid Labile Coat*

| Ingredients | % w/w |
|---|---|
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*1375.64 g of coating suspension was made and applied to 500 g of tablets

Formula for Alkalinizing Coat*

| Ingredients | % w/w |
|---|---|
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the stearic acid from the core formula were charged into a high shear granulator and dry mixed for less than 10 minutes. The dry mixed granules were discharged into a Paterson Kelly V-Blender. The stearic acid was then added to the V-Blender. The granules were blended for less than 10 minutes.

Step 1b. Preparation of the Core (Immediate Release Tablets):

The cores are tablets made from the granules prepared in Step1a. A rotary press was set-up to produce capsule shaped tablets each weighing about 300 mg (a Manesty tablet press with 16 stations was used). Granules from Step1a were charged into a feed hopper and the tablet was produced from the double rotary press by applying suitable compression force to give tablets of required thickness, hardness and friability.

Step 2. Preparation of a Coating Suspension of the Ingredients of the Acid Labile (Coat):

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 40 mg/cm$^2$ to about 50 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 15. Hydromorphone HCl Overdose+Insufflation Resistant (ODIR) 8 mg Tablets

| Formula for Core | |
|---|---|
| Ingredients | % w/w |
| Hydromorphone HCl | 2.67 |
| Lactose | 46.50 |
| Sodium Lauryl Sulfate | 16.00 |
| Citric acid | 10.00 |
| Capsicum Oleoresin | 1.17 |
| Crospovidone | 2.00 |
| Microcrystalline cellulose | 15.66 |
| Starch 1500 | 5.00 |
| Magnesium stearate | 1.00 |

| Formula for the Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*1375.64 g of coating suspension was made and applied to 500 g of tablets

| Formula for Alkalinizing Coat | |
|---|---|
| Ingredients | % w/w |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the magnesium stearate from the core formula were charged into a high shear granulator and dry mixed for less than 10 minutes. The dry mixed granules were discharged into a Paterson Kelly V-Blender. The magnesium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 300 mg (a Manesty tablet press with 16 stations was used). Granules from Step1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 40 mg/cm$^2$ to about 50 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 16. Hydrocodone Bitartrate/Acetamenophen Overdose+Insufflation

Resistant (ODIR) 5/500 mg Tablets

| Formula for Core | |
|---|---|
| Ingredients | % w/w |
| Hydrocodone Bitartrate | 0.63 |
| Acetaminophen | 62.50 |
| Crospovidone | 4.00 |
| Capsaicin | 1.50 |
| Citric acid | 12.50 |
| Silicon dioxide | 1.00 |
| Microcrystalline cellulose | 13.37 |
| Povidone K90 | 2.00 |
| Stearic Acid | 1.50 |
| Magnesium stearate | 1.00 |
| | 100 |

| Formula for the Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*687.82 g of coating suspension was made and applied to 500 g of tablets

| Formula for Alkalinizing Coat* | |
|---|---|
| Ingredients | % w/w |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of povidone, stearic acid and the magnesium stearate from the core formula were charged into a high shear granulator and dry mixed for less than 10 minutes. The dry mixed granules were granulated using a 10% povidone solution. The wet granules were dried in an oven at 60° C. to a loss of drying of less than 2%. The dried granules were passed through a co-mill fitted with screen sieves with holes of size 1000 microns and discharged into a Paterson Kelly V-Blender. The stearic acid and magnesium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 800 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 40 mg/cm$^2$ to about 50 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 17. Oxycodone HCl Overdose+Insufflation Resistant (ODIR) 5 mg Tablets

| Formula for Core | |
|---|---|
| Ingredients | % w/w |
| Oxycodone HCl | 1.67 |
| Lactose | 40.67 |
| Sodium Lauryl Sulfate | 20.16 |
| Sucrose Octa Acetate | 0.50 |
| Capsaicin | 3.00 |
| Crospovidone | 2.00 |
| Microcrystalline cellulose | 20.00 |
| Starch 1500 | 10.00 |
| Stearic Acid | 2.00 |

| Formula for Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*1375.64 g of coating suspension was made and applied to 500 g of tablets

| Formula for Alkalinizing Coat* | |
|---|---|
| Ingredients | % w/w |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the stearic acid from the core formula were charged into a high shear granulator and dry mixed for less than 10 minutes. The dry mixed granules were discharged into a Paterson Kelly V-Blender. The stearic acid was then added to the V-Blender. The granules were blended for less than 10 minutes.

Step 1b. Preparation of the Core (Immediate Release Tablets):

The cores are tablets made from the granules prepared in Step1a. A rotary press was set-up to produce capsule shaped tablets each weighing about 300 mg (a Manesty tablet press with 16 stations was used). Granules from Step1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 40 mg/cm$^2$ to about 50 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 18. Oxymorphone HCl Overdose+Insufflation Resistant (ODIR) 10 mg Tablets

| Formula for Core | |
|---|---|
| Ingredients | % w/w |
| Oxymorphone HCl | 10.00 |
| Lactose | 35.00 |
| Sodium Lauryl Sulfate | 19.33 |
| Quassin | 1.50 |
| Citric acid | 10.00 |
| Capsicum Oleoresin | 1.17 |
| Crospovidone | 2.00 |
| Microcrystalline cellulose | 15.00 |
| Starch 1500 | 5.00 |
| Magnesium stearate | 1.00 |
| | 100 |

| Formula for Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*1375.64 g of coating suspension was made and applied to 500 g of tablets

| Formula for Alkalinizing Coat* | |
|---|---|
| Ingredients | % w/w |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the magnesium stearate from the core formula were charged into a high shear granulator and dry mixed for less than 10 minutes. The dry mixed granules were discharged into a Paterson Kelly V-Blender. The magnesium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 300 mg (a Manesty tablet press with 16 stations was used). Granules from Step1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 40 mg/cm$^2$ to about 50 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalanizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 19. Warfarin Sodium Overdose Resistant (ODR) 10 mg Tablets

| Formula for Core | |
| --- | --- |
| Ingredients | % w/w |
| Warfarin sodium | 5.00 |
| Lactose | 84.00 |
| Starch 1500 | 10.00 |
| Magnesium stearate | 1.00 |

| Formula for Acid Labile Coat* | |
| --- | --- |
| Ingredients | % w/w |
| Eudragit E | 9.73 |
| Sodium Lauryl Sulfate | 0.97 |
| Talc | 3.40 |
| Stearic Acid | 1.46 |

-continued

| Formula for Acid Labile Coat* | |
| --- | --- |
| Ingredients | % w/w |
| Simethicone Emulsion 30% | 2.81 |
| Water | 81.63 |

*1375.64 g of coating suspension was made and applied to 500 g of tablets

| Formula for Alkalinizing Coat* | |
| --- | --- |
| Ingredients | % w/w |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of the magnesium stearate from the core formula were charged into a high shear granulator and dry mixed for less than 10 minutes. The dry mixed granules were discharged into a Paterson Kelly V-Blender. The magnesium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 200 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 40 mg/cm$^2$ to about 50 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 20. Codeine+Acetaminophen Overdose Resistant (ODR) 30/300 mg Tablets

| Formula for Core | |
|---|---|
| Ingredients | % w/w |
| Codeine phosphate | 5.00 |
| Acetaminophen | 50.00 |
| Sodium metabisulfite | 0.30 |
| Microcrystalline cellulose | 28.20 |
| Starch 1500 | 15.00 |
| Magnesium stearate | 1.50 |

| Formula for Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*687.82 g of coating suspension was made and applied to 500 g of tablets

| Formula for Alkalinizing Coat* | |
|---|---|
| Ingredients | % w/w |
| Opadry White | 10.00 |
| Magnesium Hydroxide | 20.18 |
| Water | 69.82 |

*1000 g of coating suspension was made and applied to 500 g of tablets

Processing Techniques

Step 1a. Preparation of Granules for the Core:

All the ingredients with the exception of magnesium stearate from the core formula were charged into a high shear granulator and dry mixed for less than 10 minutes. The dry mixed granules were granulated using. The wet granules were dried in an oven at 60° C. to a loss of drying of less than 2%. The dried granules were passed through a co-mill fitted with screen sieves with holes of size 1000 microns and discharged into a Paterson Kelly V-Blender. The magnesium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 600 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 30 mg/cm$^2$ to about 40 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 21. Methylphenidate HCl Overdose Resistant (ODR) 10 mg Tablets

| Formula for Core | |
|---|---|
| Ingredients | % w/w |
| Methylphenidate HCl | 5.00 |
| Lactose | 80.00 |
| Hydroxypropyl methylcellulose | 4.00 |
| Starch 1500 | 10.00 |
| Magnesium stearate | 1.00 |

| Formula for Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |

-continued

Formula for Acid Labile Coat*

| Ingredients | % w/w |
|---|---|
| Simethicone Emulsion 30% | 2.81 |
| Water | 81.63 |

*1375.64 g of coating suspension was made and applied to 500 g of tablets

Formula for Alkalinizing Coat*

| Ingredients | % w/w |
|---|---|
| Opadry White | 10.00 |
| Magnesium Hydroxide | 15.18 |
| Aluminium Hydroxide | 5.00 |
| Water | 69.82 |

*1000 g of coating suspension was made and applied to 500 g of tablets

Processing Techniques

Step 1a. Preparation of Granules for the Core:

All the ingredients with the exception of the magnesium stearate from the core formula were charged into a high shear granulator and dry mixed for less than 10 minutes. The dry mixed granules were discharged into a Paterson Kelly V-Blender. The magnesium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 200 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 40 mg/cm$^2$ to about 50 mg/cm$^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 22. Tramadol HCl Overdose Resistant (ODR) 50 mg Tablets

Formula for Core

| Ingredients | % w/w |
|---|---|
| Tramadol HCl | 12.50 |
| Lactose | 57.50 |
| Hydroxypropyl methylcellulose | 4.00 |
| Microcrystalline cellulose | 15.00 |
| Starch 1500 | 10.00 |
| Magnesium stearate | 1.00 |

Formula for Acid Labile Coat*

| Ingredients | % w/w |
|---|---|
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*1375.64 g of coating suspension was made and applied to 500 g of tablets

Formula for Alkalinizing Coat*

| Ingredients | % w/w |
|---|---|
| Opadry White | 10.00 |
| Magnesium Hydroxide | 15.18 |
| Aluminium Hydroxide | 5.00 |
| Water | 69.82 |

*1000 g of coating suspension was made and applied to 500 g of tablets

Processing Techniques

Step 1a. Preparation of Granules for the Core:

All the ingredients with the exception of the magnesium stearate from the core formula were charged into a high shear granulator and dry mixed for less than 10 minutes. The dry mixed granules were discharged into a Paterson Kelly V-Blender. The magnesium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 400 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients of the Acid Labile Coat:

(I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form an Acid Labile Coat Surrounding the Tablet from Step 1b:

Tablets from Step 1b were charged into a rotating drum of a side vented automated tablet coater. The suspension from Step 2 was applied to the tablets obtained from Step 1b, using a peristaltic pump and spray gun. The suspension was dried as a film onto the tablets, using heated air drawn through the tablet bed from an inlet fan. A sufficient amount of the suspension was applied to form about 25 $mg/cm^2$ to about 35 $mg/cm^2$ of the coat surrounding the tablet.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Tablet from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to a weight gain of about 50% wt/wt to about 70% wt/wt of the coated tablet from Step 3.

Example 23. Pregabalin Overdose Resistant (ODR) 50 mg Capsules

| Formula for Core (Spheres) | |
|---|---|
| Ingredients | % w/w |
| Pregabalin | 60.00 |
| Hydroxypropyl methylcellulose | 4.00 |
| Microcrystalline cellulose | 35.00 |
| Talc | 1.00 |

| Formula for Acid Labile Coat* | |
|---|---|
| Ingredients | % w/w |
| Eudragit E | 9.73 |
| Sodium Lauryl Sulfate | 0.97 |
| Talc | 3.40 |
| Stearic Acid | 1.46 |
| Simethicone Emulsion 30% | 2.81 |
| Water | 81.63 |

*1375.64 g of coating suspension was made and applied to 500 g of spheres

| Formula for Alkalinizing Coat* | |
|---|---|
| Ingredients | % w/w |
| Opadry White | 10.00 |
| Magnesium Hydroxide | 15.18 |
| Aluminium Hydroxide | 5.00 |
| Water | 69.82 |

*1000 g of coating suspension was made and applied to 500 g of spheres

Processing Techniques

Step 1a. Preparation of Wet Granules to Make Spheres for the Core:

All the ingredients from the core formula were charged into a high shear granulator and dry mixed for less than 10 minutes. The dry mixed granules were wet granulated with water.

Step 1b. Preparation of Spheres for the Core by Extrusion/Spheronization:

The cores are spherical beads made from the wet granules prepared in Step 1a. An extruder and spheronizer was set-up to produce spherical beads of potency 60%. Wet granules from Step 1a were charged into the extruder and extruded. The extrudates were discharged into a spheronizer and spheronised to form spherical beads of between 850 to 1000 microns in diameter. The beads where dried in a conventional oven at 60 degrees centigrade to a loss of drying less than 2.0%.

Step 2. Preparation of a Coating Suspension of the Ingredients of the Acid Labile Coat (I) Water was added into a stainless steel vessel followed by sodium lauryl sulfate until dissolved. To this was added stearic acid followed by Eudragit E and talc, step-by-step, while stirring vigorously with a high shear mixer until all ingredients were finely dispersed in a suspension. (II) Simethicone emulsion was added to the Eudragit E suspension while stirring using a high shear mixer.

Step 3. Application of the Coating Suspension from Step 2 to Form a pH Sensitive Coat Surrounding the Spheres from Step 1b:

Spheres from Step 1b were charged into a fluid bed coater with a bottom spray (Wurster) assembly. The suspension from Step 2 was applied to the spheres obtained from Step 1b, using a peristaltic pump and spray gun. The suspension was dried as a film onto the spheres, using heated air drawn through the fluid bed from an inlet fan. A sufficient amount of the suspension was applied to form about 15 $mg/cm^2$ to about 20 $mg/cm^2$ of the coat surrounding the spheres.

Step 4. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 5. Application of the Coating Suspension from Step 4 to Form an Alkalinizing Coat Surrounding the Coated Spheres from Step 3:

Spheres from Step 1b were charged into a fluid bed coater with a bottom spray (Wurster) assembly. The suspension from Step 2 was applied to the spheres obtained from Step 1b, using a peristaltic pump and spray gun. The suspension was dried as a film onto the spheres, using heated air drawn through the fluid bed from an inlet fan. A sufficient amount of the suspension was applied to a weight gain of about 40% wt/wt to about 50% wt/wt of the coated spheres from Step 3.

Step 6. Encapsulation of Spheres from Step 5 into Hard Gelatin Capsules:

Spheres from Step 5 were filled into hard gelatin capsules. A sufficient amount of the spheres to give 50 mg of Pregabalin per filled capsule was encapsulated.

Example 24

Similar experiments with respect to the above examples were conducted using a variety of alkalinizing agent(s) in the alkalinizing coat. The results were similar to those obtained with respect to the above examples, wherein dissolution of the unit dosage forms was inversely correlated with the number added to an acidic solution.

Example 25. Oxycodone Sustained Action (SA) 80 mg ODR Tablets (Each Tablet contain 60 mg in the core and 20 mg external to the core)

| Formula for core | |
|---|---|
| Ingredients | % w/w |
| Oxycodone HCl | 30.00 |
| Polyethylene Oxide | 50.00 |
| Polyethylene Glycol | 16.50 |
| Butylated hydroxytoluene | 0.50 |
| Eudragit RL | 2.00 |
| Magnesium stearate | 1.00 |

| Formula for Loading Dose | |
|---|---|
| Ingredients | % w/w |
| Opadry White | 12.63 |
| Oxycodone HCl | 2.37 |
| Water | 85.00 |

| Formula for Acid labile coat | |
|---|---|
| Ingredients | % w/w |
| Eudragit E (milled) | 59.30 |
| Sodium Lauryl sulfate | 5.93 |
| Stearic acid (milled) | 8.89 |
| Talc | 20.75 |
| Simethicone | 5.13 |
| Water | Qs |

| Formula for Alkalinizing Coat | |
|---|---|
| Ingredients | % w/w |
| Opadry White | 10.00 |
| Magnesium Hydroxide | 20.18 |
| Water | 69.82 |

Processing Techniques

Step 1a. Preparation of Granules for the Maintenance Dose by Hot Melt Extrusion:

All the ingredients with the exception of the magnesium stearate from the core formula were added into a high shear granulator and dry mixed for less than 10 minutes. The dry mixed granules were discharged into a hopper of a Hot Melt Extruder and gradually fed into the Hot Melt Extruder heated barrel, while mixing by using the rotating screw element of the extruder. The material was extruded through a die attached at the end of a barrel. The extrudates were milled into granules. The milled granules were charged into a Paterson Kelly V-Blender. The magnesium stearate was added into the V-Blender and blended for less than 10 minutes.

Step 1b. Preparation of the Granules for Loading Dose by Hot Melt Extrusion:

All the ingredients with the exception of the magnesium stearate and microcrystalline cellulose from the maintenance dose formula were added into a high shear granulator and dry mixed for less than 10 minutes. The dry mixed granules were discharged into a hopper of a Hot Melt Extruder and gradually fed into the Hot Melt Extruder heated barrel, while mixing by using the rotating screw element of the extruder. The material was extruded through a die attached at the end of a barrel. The extrudates were milled into granules. The milled granules were charged into a Paterson Kelly V-Blender. The magnesium stearate and microcrystalline cellulose were added into the V-Blender and blended for less than 10 minutes. The barrel section temperatures of the hot melt extruder are typically optimized so that the viscosity of the melt is low enough to allow conveying down the barrel and proper mixing, while keeping temperatures low enough to avoid thermal degradation of the materials; typically about 100 to about 200° C.

Step 1c. Preparation of the Core (Extended Release Tablets):

The cores are tablets made from the granules prepared in Step 1b. A rotary press was set-up to produce capsule shaped tablets each weighing about 400 mg (a Manesty tablet press with 16 stations was used). Granules from Step 1b were charged into a feed hopper and the tablet was produced from the double rotary press by applying suitable compression force to give tablets of required thickness, hardness and friability Step 2. Preparation of a Coating Suspension of the Ingredients for the Loading Dose to be Applied to the Tablet from Step 1c:

(I) Water was added into a stainless steel vessel. (II) Opadry was added while stirring with a propeller mixer until all ingredients are finely dispersed in a suspension. (III) Oxycodone HCl was added to the Opadry water mixture while stirring using a propeller mixer.

Step 3. Application of the Coating Suspension from Step 2 to Form Part of the Loading Dose Surrounding the Tablet from Step 1c:

Tablets from step 2 were charged into a rotating drum of a side vented automated Tablet coater (Rama Cota Tablet Film Coater was used). The suspension from Step 3 was applied to the tablets obtained from Step 2, using a peristaltic pump and spray gun. The suspension was dried as a film onto the tablets, using heated air drawn through the tablet bed from an inlet fan. The suspension is applied to form a coat surrounding the tablet.

Step 4. Preparation of Acid Labile Coating Suspension to be Applied to the Tablet from Step3:

(I) Water was added into a stainless steel vessel followed by Sodium lauryl sulfate and stearic acid, step-by-step, while stirring vigorously with a high shear mixer until all ingredients are dissolved. (II) Eudragit E was added, step-by-step, while stirring vigorously with a high shear mixer until all ingredients were dissolved. (Ill) Talc was added, followed by simethicone while stirring using a high shear mixer until finely dispersed in the solution.

Step 5. Application of a Coating Suspension from Step 4 to Form an Acid Labile Coat Surrounding the Tablet from Step 3:

Tablets from step 3 were charged into the rotating drum of a side vented automated Tablet coater (Rama Cota Tablet Film Coater was used). The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to form about 10 mg/cm$^2$ to about 20 mg/cm$^2$ of the coat surrounding the tablet.

Step 6. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 7. Application of the Coating Suspension from Step 6 to Form an Alkalinizing Coat Surrounding the Coated Tablets from Step 5:

Tablets from Step 5 were charged into the rotating drum of a side vented automated Tablet coater (Rama Cota Tablet Film Coater was used). The suspension from Step 6 was applied to the tablets obtained from Step 5, using a peristaltic pump and spray gun. The suspension was dried as a film onto the tablets, using heated air drawn through the tablet bed from an inlet fan. A sufficient amount of the suspension was applied to form coat containing about 30 mg to 150 mg of magnesium hydroxide per coated tablet.

Example 26. Oxycodone Sustained Action (SA) 80 mg ODR Tablets

Each Tablet Contain 60 mg in the Core and 20 mg External to the Core

| Formula for core | |
|---|---|
| Ingredients | % w/w |
| Oxycodone HCl | 7.50 |
| Polyethylene Oxide | 43.71 |
| Lactose | 22.79 |
| Crospovidone | 10.00 |
| Microcrystalline cellulose | 10.50 |
| Eudragit RL | 5.00 |
| Magnesium stearate | 0.50 |

| Formula for Loading Dose | |
|---|---|
| Ingredients | % w/w |
| Opadry White | 12.63 |
| Oxycodone HCl | 2.37 |
| Water | 85.00 |

| Formula for Acid labile coat | |
|---|---|
| Ingredients | % w/w |
| Eudragit E (milled) | 59.30 |
| Sodium Lauryl sulfate | 5.93 |
| Stearic acid (milled) | 8.89 |

| Formula for Acid labile coat | |
|---|---|
| Ingredients | % w/w |
| Talc | 20.75 |
| Simethicone | 5.13 |
| Water | Qs |

| Formula for Alkalinizing Coat | |
|---|---|
| Ingredients | % w/w |
| Opadry White | 10.00 |
| Magnesium Hydroxide | 20.18 |
| Water | 69.82 |

Processing Techniques

Step 1a. Preparation of Granules for the Core:

All the ingredients with the exception of the magnesium stearate from the core formula were charged into a high shear granulator and dry mixed for less than 10 minutes. The dry mixed granules were discharged into a Paterson Kelly V-Blender. The magnesium stearate was then added to the V-Blender. The granules were blended for less than 10 minutes.

Step 1b. Preparation of the Core (Extended Release Tablets):

The cores are tablets made from the granules prepared in Step1a. A rotary press was set-up to produce capsule shaped tablets each weighing about 400 mg (a Manesty tablet press with 16 stations was used). Granules from Step1a were charged into a feed hopper and the tablet was produced from the double rotary press by applying suitable compression force to give tablets of required thickness, hardness and friability.

Step 2. Preparation of a Coating Suspension of the Ingredients for the Loading Dose to be Applied to the Tablet from Step 1b:

(I) Water was added into a stainless steel vessel. (II) Opadry was added while stirring with a propeller mixer until all ingredients are finely dispersed in a suspension. (III) Oxycodone HCl was added to the Opadry water mixture while stirring using a propeller mixer.

Step 3. Application of the Coating Suspension from Step 2 to Form Part of the Loading Dose Surrounding the Tablet from Step 1b:

Tablets from step 1b were charged into a rotating drum of a side vented automated Tablet coater (Rama Cota Tablet Film Coater was used). The suspension from Step 2 was applied to the tablets obtained from Step 1b, using a peristaltic pump and spray gun. The suspension was dried as a film onto the tablets, using heated air drawn through the tablet bed from an inlet fan. The suspension is applied to form a coat surrounding the tablet.

Step 4. Preparation of Acid Labile Coating Suspension to be Applied to the Tablet from Step3:

(I) Water was added into a stainless steel vessel followed by Sodium lauryl sulfate and stearic acid, step-by-step, while stirring vigorously with a high shear mixer until all ingredients are dissolved. (II) Eudragit E was added, step-by-step, while stirring vigorously with a high shear mixer until all ingredients were dissolved. (III) Talc was added, followed by simethicone while stirring using a high shear mixer until finely dispersed in the solution.

Step 5. Application of a Coating Suspension from Step 4 to Form an Acid Labile Coat Surrounding the Tablet from Step 3:

Tablets from step 3 were charged into the rotating drum of a side vented automated Tablet coater (Rama Cota Tablet Film Coater was used). The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to form about 10 mg/cm$^2$ to about 20 mg/cm$^2$ of the coat surrounding the tablet.

Step 6. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 7. Application of the Coating Suspension from Step 6 to Form an Alkalinizing Coat Surrounding the Coated Tablets from Step 5:

Tablets from Step 5 were charged into the rotating drum of a side vented automated Tablet coater (Rama Cota Tablet Film Coater was used). The suspension from Step 6 was applied to the tablets obtained from Step 5, using a peristaltic pump and spray gun. The suspension was dried as a film onto the tablets, using heated air drawn through the tablet bed from an inlet fan. A sufficient amount of the suspension was applied to form coat containing about 70 mg to 150 mg of magnesium hydroxide per coated tablet.

Example 27. Dissolution Test of Coated Tablets from Example 26

Figure 17:
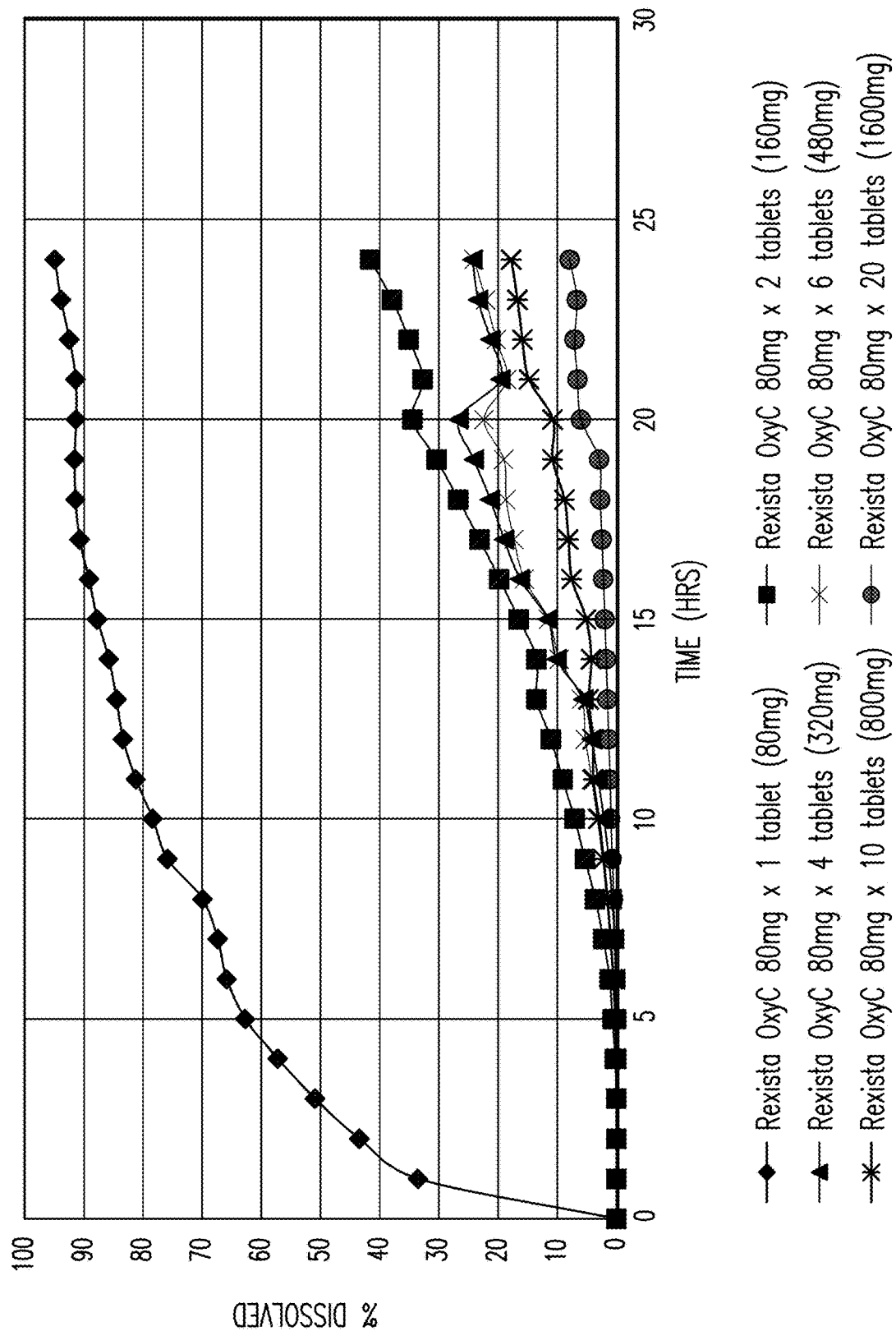
FIG. 17 shows dissolution of various quantities of intact Rexista OxyC 80 mg Tablets (ODRA type1) One tablet of Rexista OxyC 80 mg (ODRA type1): Media 0.01N HCl, 37° C., Paddle Speed 100 RPM.
Figure 18:
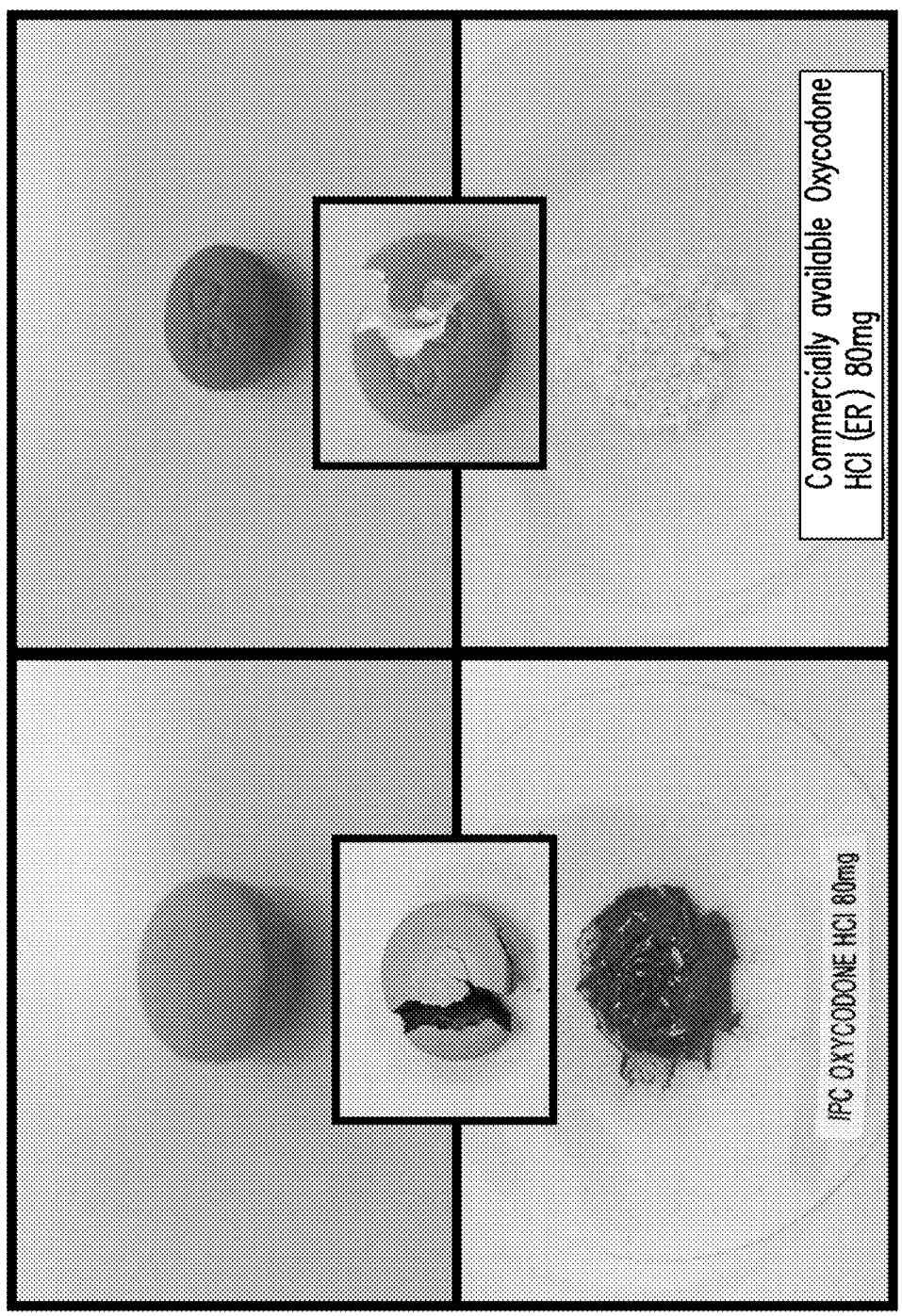
FIG. 18 shows a comparison of different physical states of intact, broken and ground (using mortar and pestle) of Rexista Oxycodone ER tablets from Example 29 vs. Commercially available Oxycodone HCl (ER) tablets.
Figure 19:
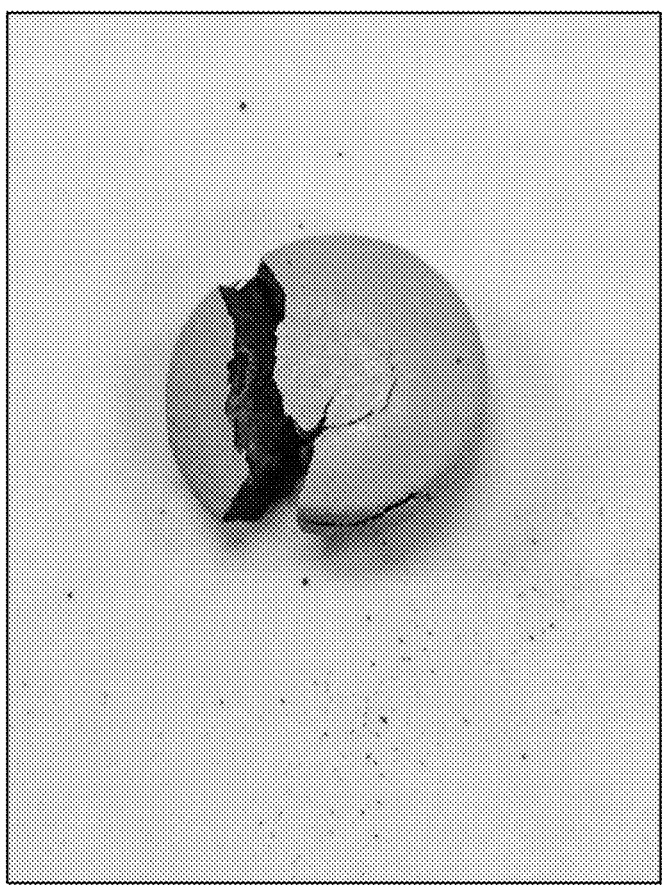
FIG. 19 shows Rexista Oxycodone ER tablets from Example 29 broken, showing cross section of a blue colored core containing abuse deterrent coloring agent
Figure 20:
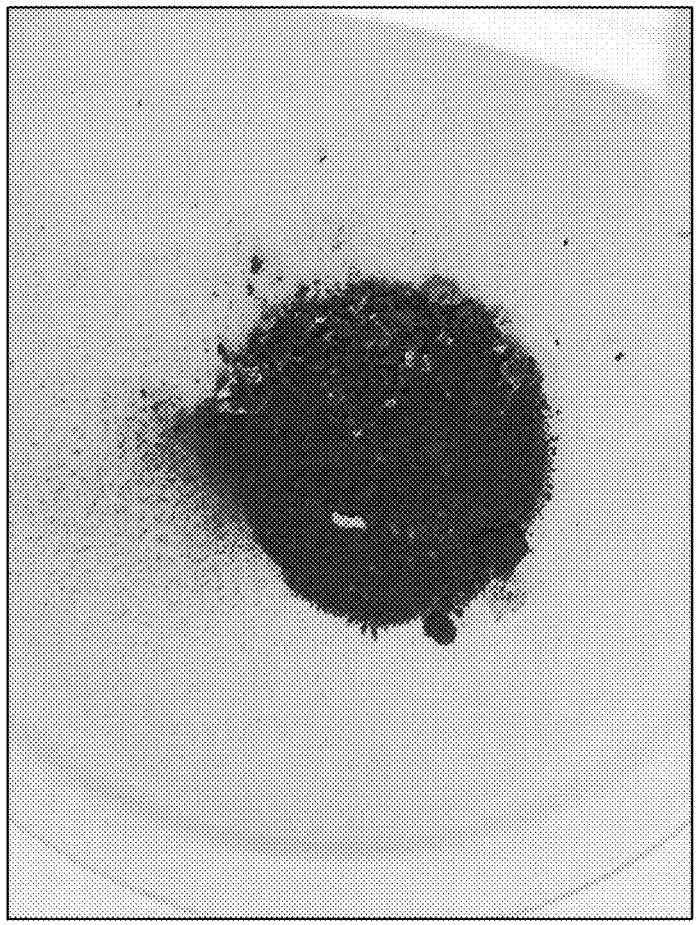
FIG. 20 shows particles of Rexista Oxycodone ER tablets from Example 29 formed after grinding an intact tablet (using mortar and pestle) showing the blue colored core containing an abuse deterrent coloring agent.
Figure 21:
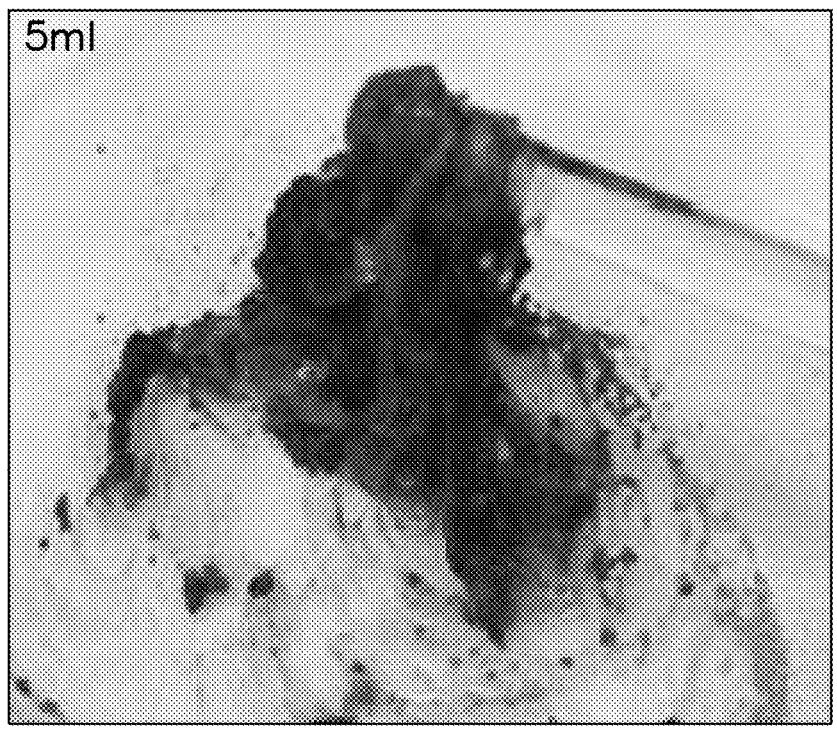
FIG. 21 shows formation of a disagreeable blue colored viscous sticky gel when particles from Rexista Oxycodone ER tablets from Example 29 are ground (using mortar and pestle) and are placed in contact with 5 ml of water. Blue color is due to abuse deterrent coloring agent.
Figure 22:
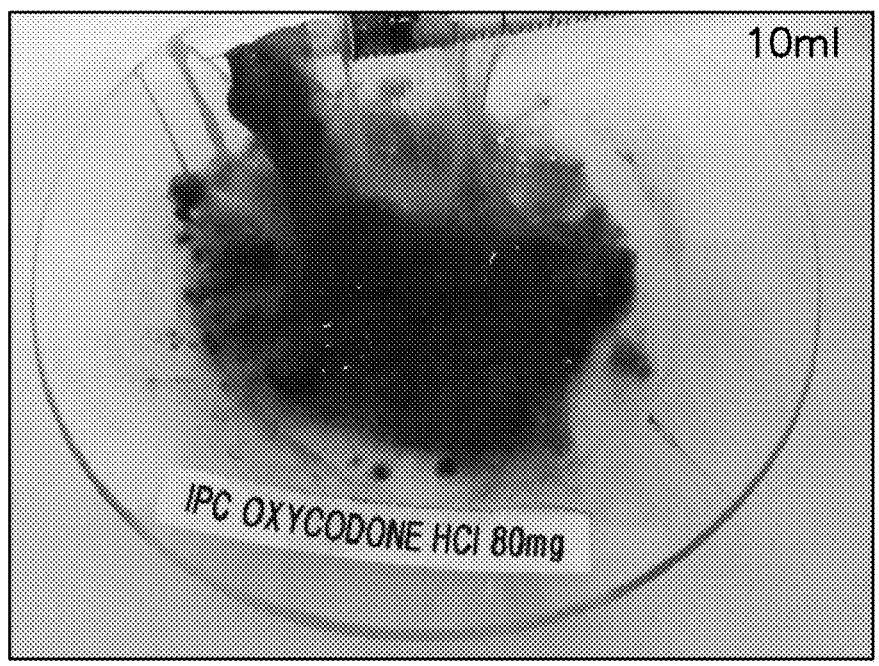
FIG. 22 shows formation of a disagreeable blue colored viscous sticky gel which is difficult to syringe when particles from Rexista Oxycodone ER tablets from Example 29 are ground (using mortar and pestle) and are placed in contact with 10 ml of water. Blue color is due to abuse deterrent coloring agent.
Figure 23:
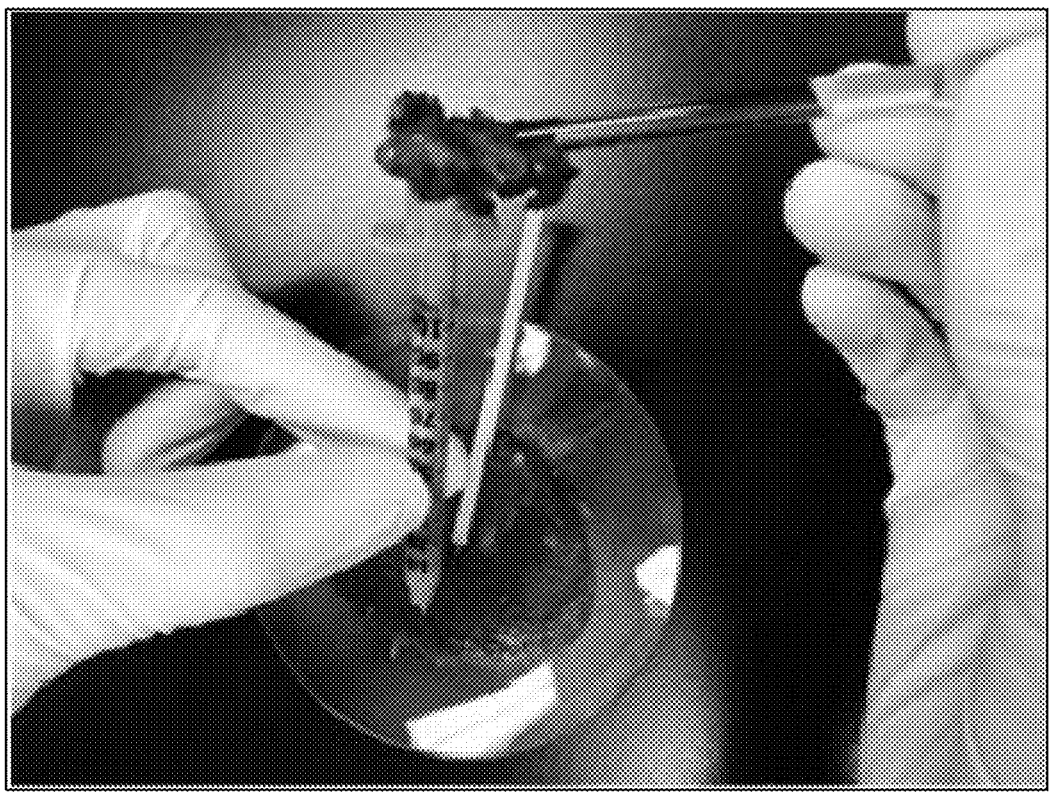
FIG. 23 shows that when particles from Rexista Oxycodone ER tablets from Example 29 are ground (using mortar and pestle) and are placed in contact with water for the purpose of abusing it via intravenous injection; it is difficult to fill it into a syringe due to the formation of a disagreeable blue colored viscous sticky gel.
Figure 24:
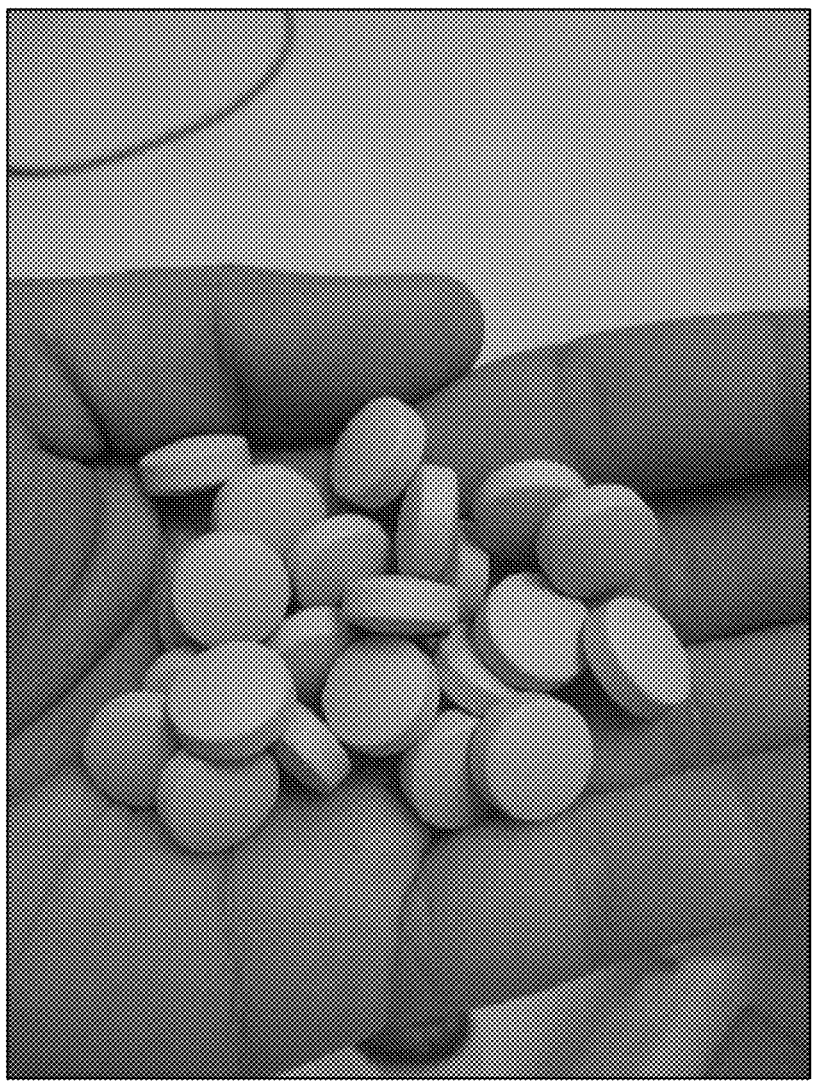
FIG. 24 shows Rexista Oxycodone ER 80 mg tablets from Example 29 that is intact and therefore, does not stain the hands with the disagreeable abuse deterrent coloring agent as it is incorporated in the tablet core.
Figure 25:
FIG. 25 shows that crushing and handling Rexista Oxycodone ER 80 mg tablets from Example 29 for the purpose of abuse, releases and leaves behind the disagreeable abuse deterrent coloring agent that was incorporated in the tablet core.
Figure 26:
FIG. 26 shows that chewing and licking of Rexista Oxycodone ER 80 mg tablets from Example 29 for the purpose of abuse, releases and leaves behind the disagreeable abuse deterrent coloring agent incorporated in the tablet core, resulting in a disgusting blue coloration of the tongue, lips, teeth and mouth thus, stigmatizing the individual.
Figure 27:
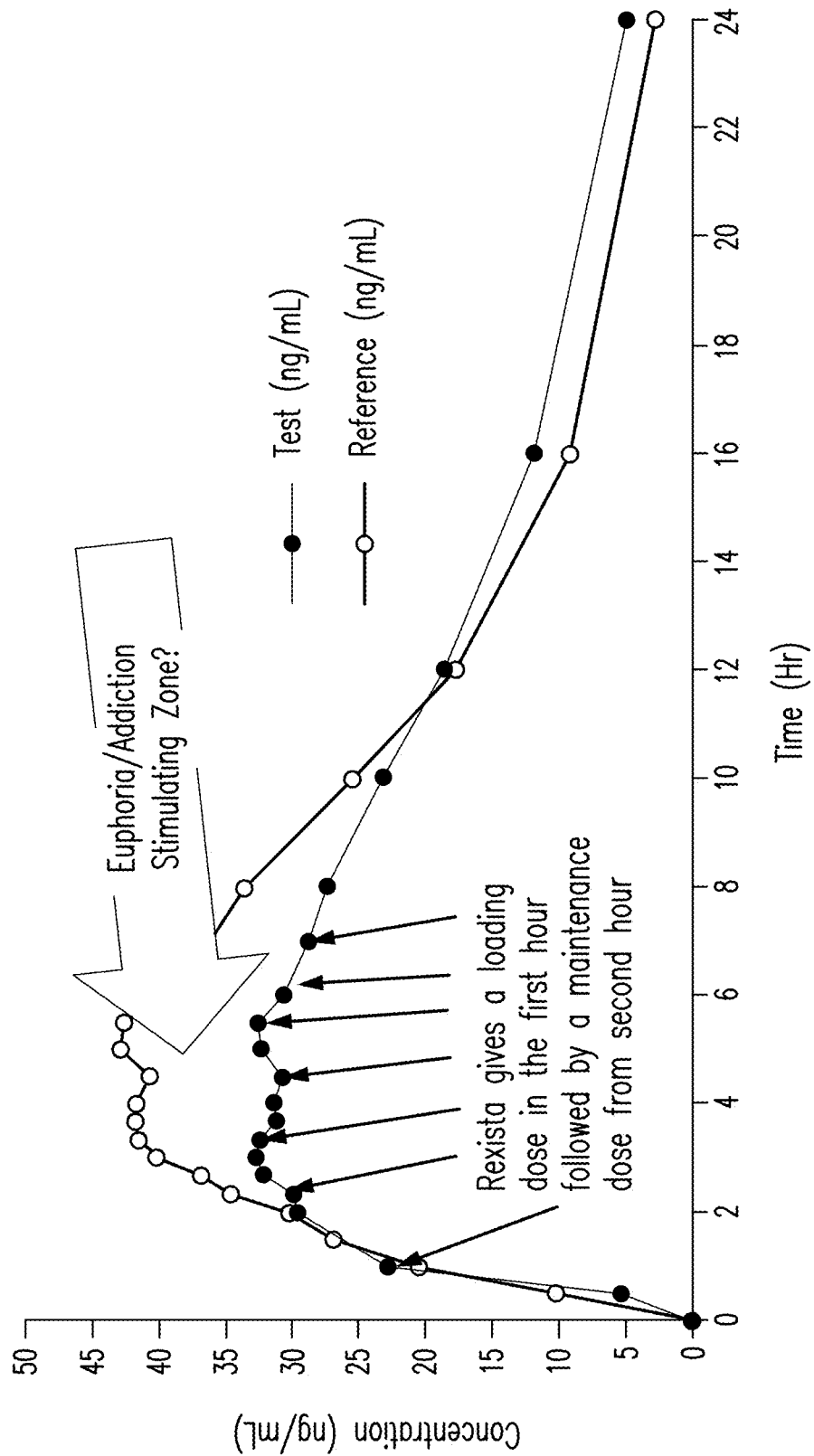
FIG. 27 shows mean plasma oxycodone concentration vs. time, Rexista 40 mg tablets vs. Commercially available Oxycodone HCl (ER) 40 mg tablets (Reference) under fasting condition.
Figure 28:
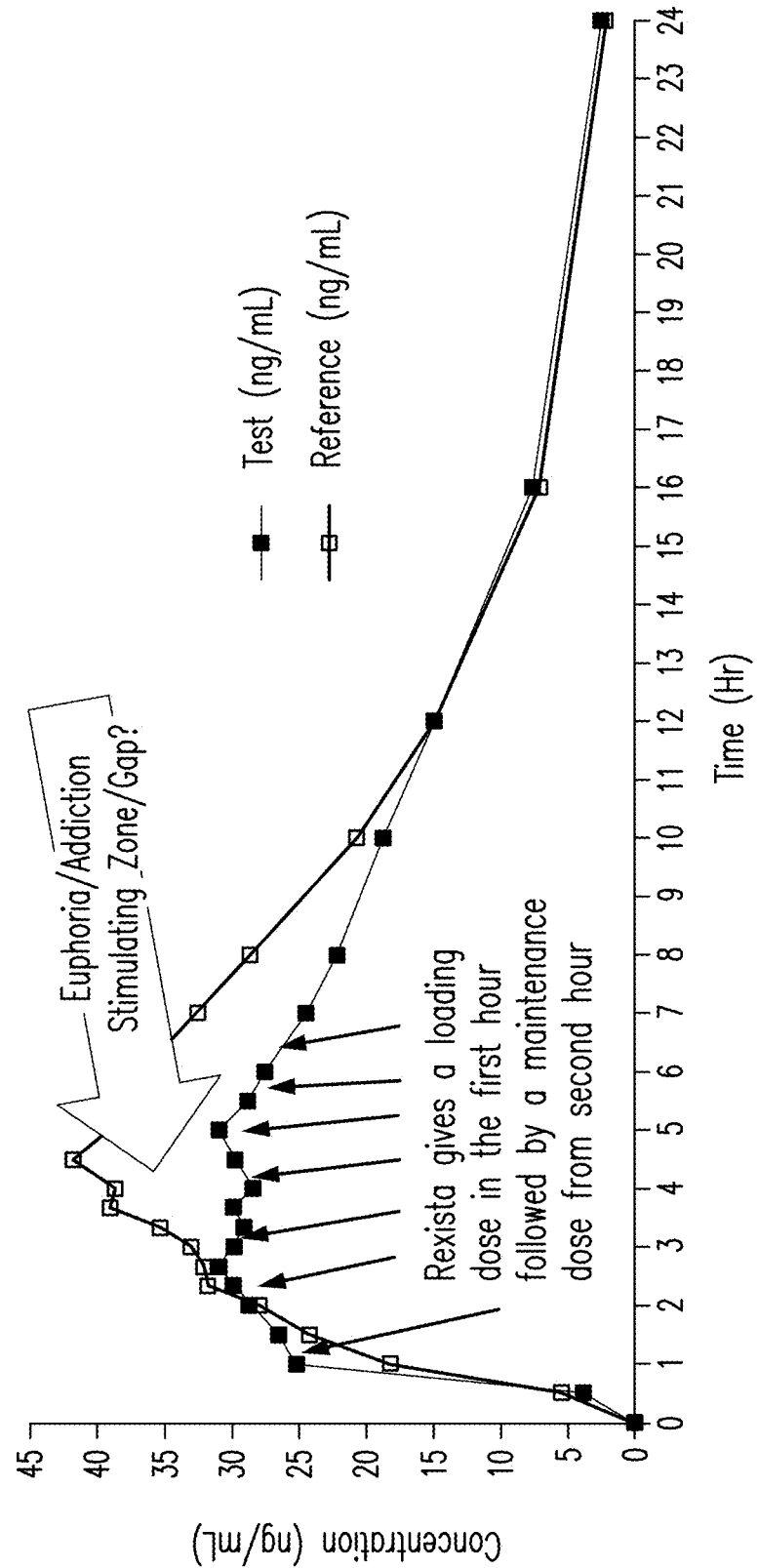
FIG. 28 shows mean plasma oxycodone concentration vs. time, Rexista 40 mg tablets vs. Commercially available Oxycodone HCl (ER) 40 mg tablets (Reference) under fed conditions.
Figure 29:
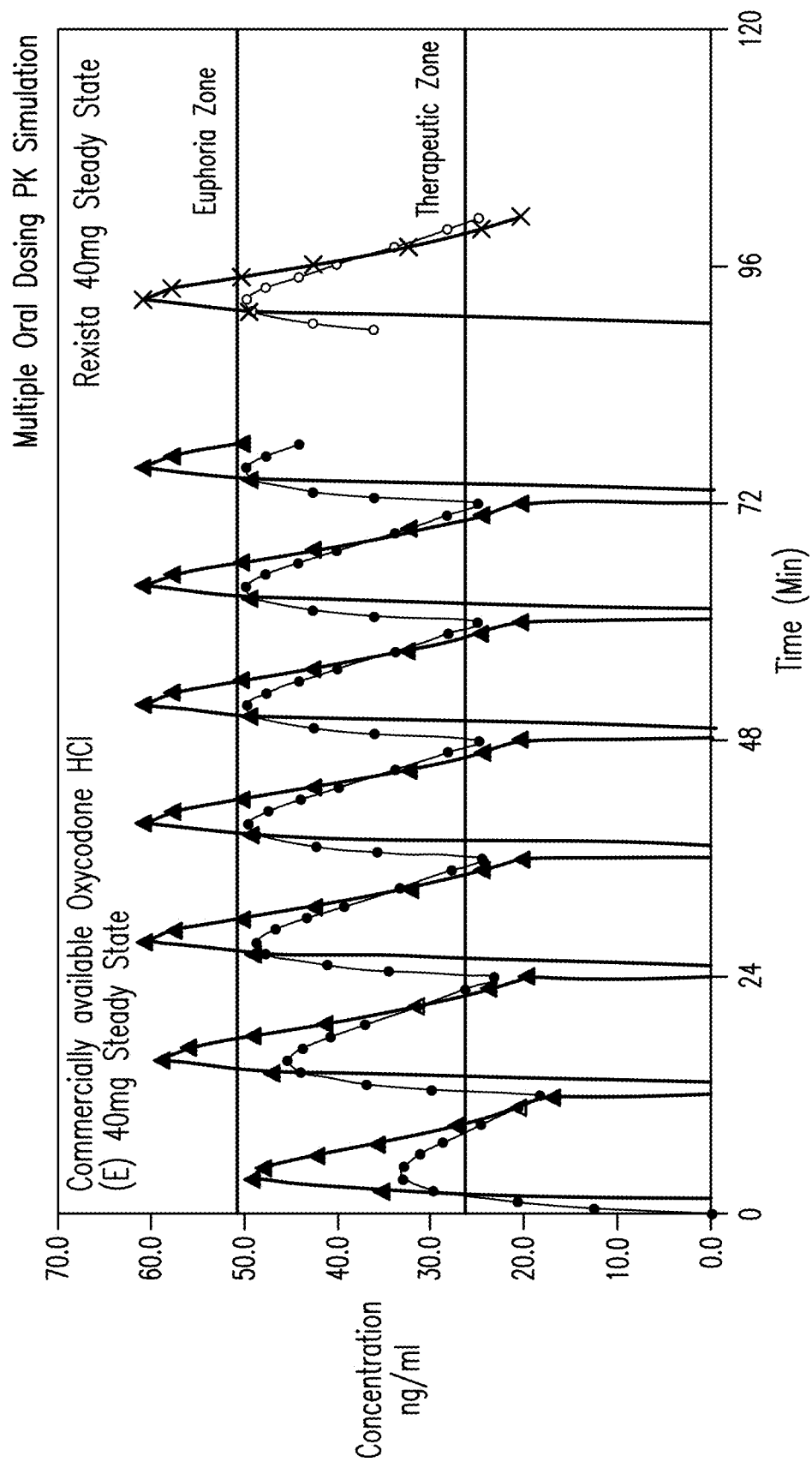
FIG. 29 shows oral multiple dose simulation pharmacokinetic modelling of mean plasma oxycodone concentration vs. time, Rexista 40 mg tablets vs. Commercially available Oxycodone HCl (ER) 40 mg tablets.
Figure 30:
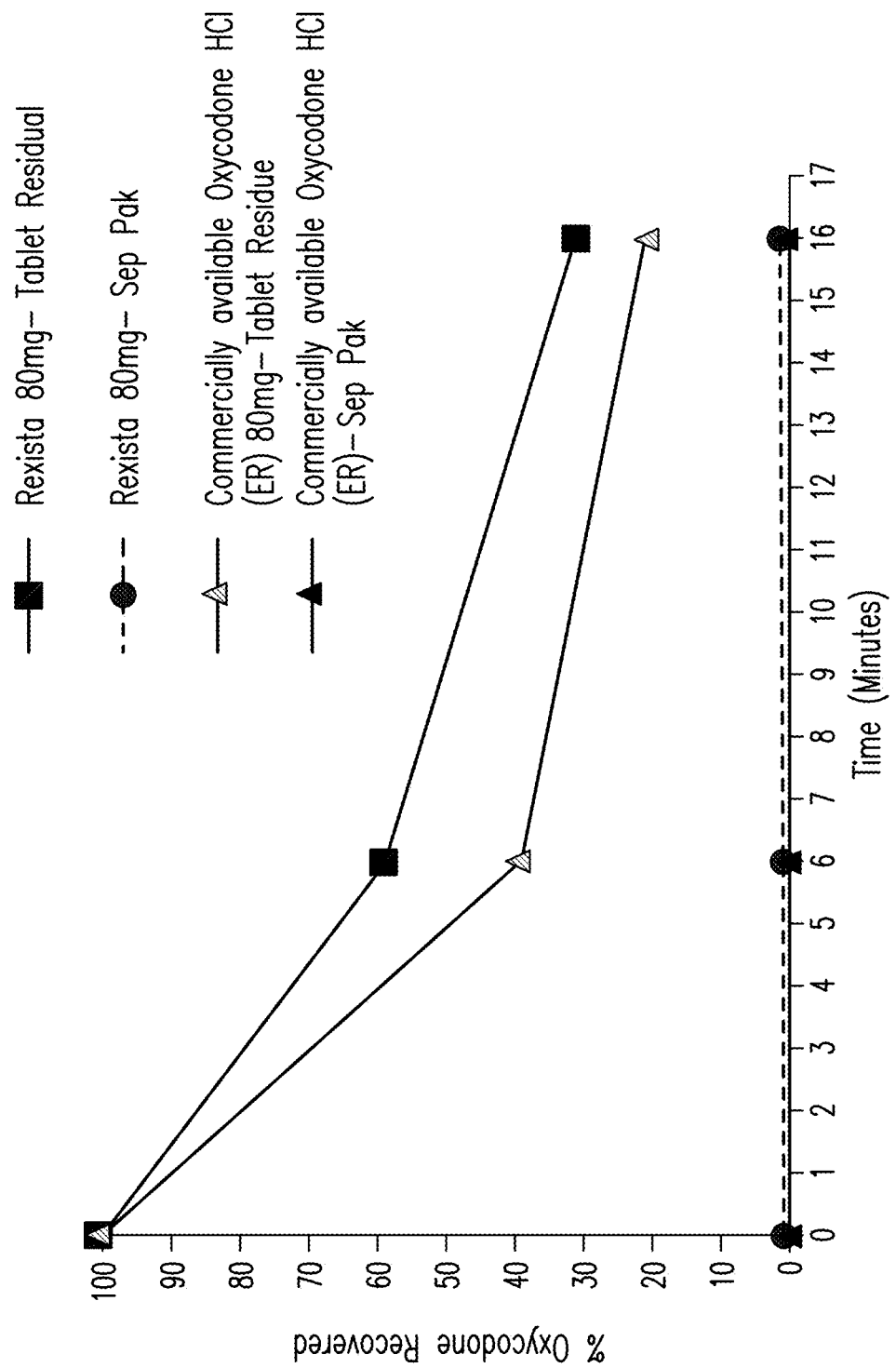
FIG. 30 shows result of vaporization studies of Rexista Oxycodone ER 80 mg tablets from Example 29 vs Commercially available Oxycodone HCl (ER).
Figure 31:
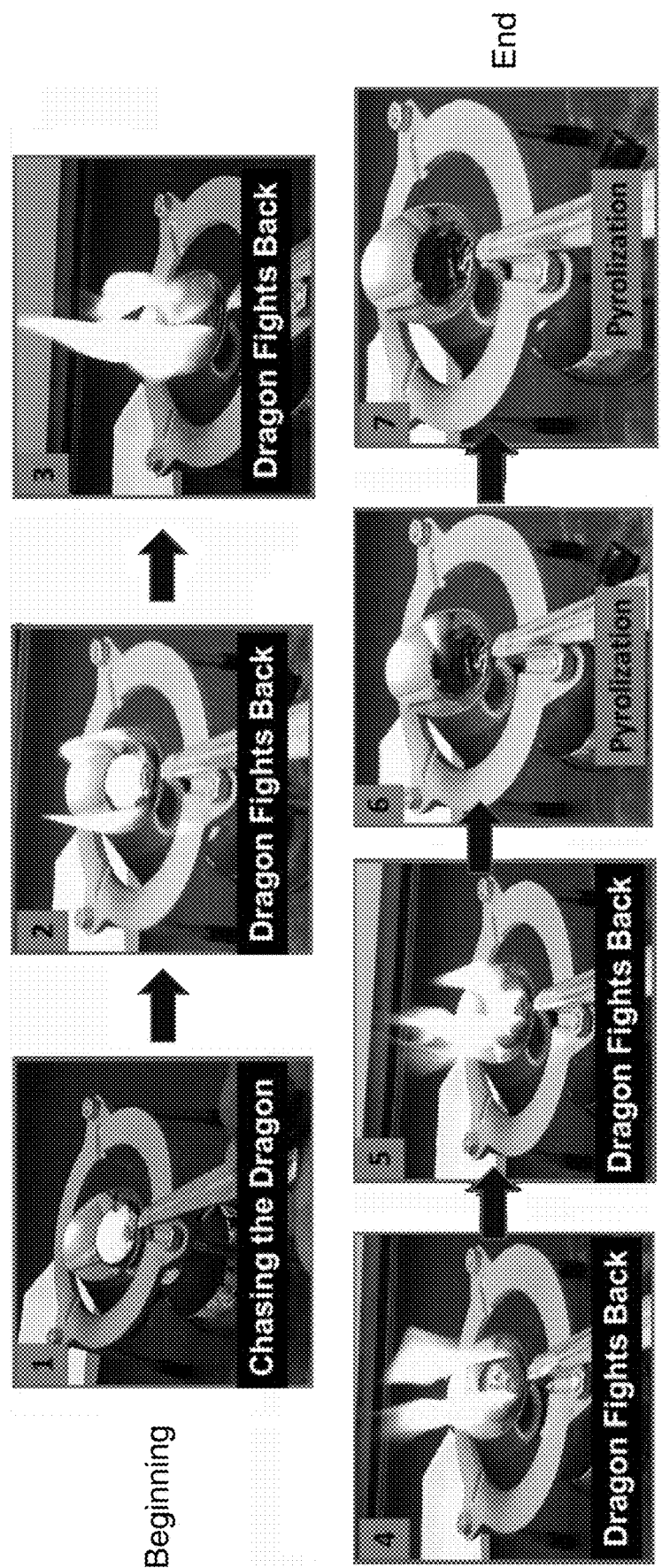
FIG. 31 shows effect of subjecting pulverized particles of Rexista to an open flame.

Table 17 and FIG. 17 below show the amount of oxycodone released in percent over a 24 hour period when one tablet or multiple tablets are subjected to dissolution in 0.01N HCl solution using USP Paddle at 100 rpm. The results show that the more unit dosage forms there are, the less the amount of drug released. Less than 1% of the drug is released even after 5 hours when 2 or more tablets are present, and less than 5% of drug is released after 12 hours for 4 tablets, 6 tablets, 8 tablets, 10 or more tablets. It is even more dramatic for 20 tablets where less than 5% is released in 19 hours with only 8% of the drug being released in 24 hours.

TABLE 17

Dissolution of various quantities of intact Rexista OxyC 80 mg Tablets (ODRA type1) One tablet of Rexista OxyC 80 mg (ODRA type1): Media 0.01N HCl, 37° C., Paddle Speed 100 RPM

| | Amounts released (%) | | | | | |
|---|---|---|---|---|---|---|
| Time (hrs) | Rexista OxyC 80 mg × 1 tablet (80 mg) | Rexista OxyC 80 mg × 2 tablets (160 mg) | Rexista OxyC 80 mg× 4 tablets (320 mg) | Rexista OxyC 80 mg × 6 tablets (480 mg) | Rexista OxyC 80 mg × 10 tablets (800 mg) | Rexista OxyC 80 mg × 20 tablets (1600 mg) |
| 0 | 0 | 0 | 0 | 0 | 0 | 0 |
| 1 | 33.5 | 0 | 0 | 0 | 0 | 0 |
| 2 | 43.463 | 0 | 0 | 0 | 0 | 0 |
| 3 | 50.9559789 | 0 | 0 | 0.0438 | 0.0288 | 0 |
| 4 | 57.2340725 | 0.2813 | 0 | 0.0793 | 0.0788 | 0.0219 |
| 5 | 62.6811714 | 0.7071 | 0 | 0.2233 | 0.2478 | 0.0838 |
| 6 | 65.8323101 | 1.1842 | 0.1219 | 0.5177 | 0.5711 | 0.1828 |
| 7 | 67.3656349 | 2.2628 | 0.3441 | 0.986 | 1.0191 | 0.3215 |
| 8 | 69.931139 | 3.6072 | 0.7514 | 1.6223 | 1.5772 | 0.5006 |
| 9 | 75.8295047 | 5.3557 | 1.3537 | 2.4002 | 2.2095 | 0.7328 |
| 10 | 78.3210006 | 7.0971 | 2.1454 | 3.2596 | 2.995 | 0.9775 |
| 11 | 81.2326784 | 9.1001 | 3.127 | 4.1883 | 3.9079 | 1.0911 |
| 12 | 83.4283614 | 11.078 | 4.2178 | 5.2908 | 3.9974 | 1.3457 |
| 13 | 84.5183562 | 13.475 | 5.5496 | 5.9279 | 4.6872 | 1.5567 |
| 14 | 85.8117431 | 13.472 | 10.129 | 9.6337 | 4.2729 | 1.7634 |
| 15 | 87.7341677 | 16.495 | 11.623 | 11.484 | 5.141 | 1.9826 |
| 16 | 89.1501124 | 19.765 | 16.316 | 15.555 | 7.5581 | 2.2368 |
| 17 | 90.7205050 | 23.12 | 18.948 | 17.335 | 8.1241 | 2.4731 |
| 18 | 91.4208464 | 26.717 | 21.335 | 18.635 | 8.8068 | 2.7214 |
| 19 | 91.5859017 | 30.319 | 24.08 | 19.01 | 10.804 | 2.9568 |
| 20 | 91.3139805 | 34.445 | 26.608 | 22.362 | 10.765 | 6.0216 |
| 21 | 91.3911942 | 32.696 | 19.607 | 18.551 | 14.782 | 6.6043 |
| 22 | 92.4465798 | 35.03 | 21.3 | 20.303 | 15.905 | 7.0914 |
| 23 | 93.8800000 | 37.846 | 23.366 | 22.083 | 16.727 | 6.7012 |
| 24 | 94.9274496 | 41.646 | 24.308 | 24.044 | 17.764 | 7.9217 |

Example 28. Preparation of Pantoprazole Overdose Resistant (ODR) 10 mg Tablets

| Formula for Core | |
|---|---|
| Ingredients | % w/w |
| Pantoprazole sodium | 22.17 |
| Lactose | 20.11 |
| Polyvinyl pyrolidone | 0.65 |
| Crospovidone | 10.00 |
| Sodium carbonate | 41.15 |
| Calcium stearate | 15.00 |
| Sodium lauryl sulphate | 4.93 |

| Formula for seal Coat | |
|---|---|
| Ingredients | % w/w |
| Opadry White | 11.25 |
| Magnesium Hydroxide | 3.75 |
| Water | 85.00 |

| Formula for Alkaline Labile Enteric Coat | |
|---|---|
| Ingredients | % w/w |
| Eudragit L | 76.33 |
| Triethyl citrate | 9.16 |
| Glycerol monostaerate | 14.50 |
| Water | qs |

| Formula for Acidifying Coat | |
|---|---|
| Ingredients | % w/w |
| Opadry White | 15.00 |
| Citric acid | 3.50 |
| Fumaric acid | 3.50 |
| Water | 79.00 |

| Formula for Alkaline Labile Enteric Coat | |
|---|---|
| Ingredients | % w/w |
| Eudragit L | 76.33 |
| Triethyl citrate | 9.16 |
| Glycerol monostaerate | 14.50 |
| Water | qs |

Processing Techniques

Step 1a. Preparation of Granules for the Core:

All the ingredients with the exception of the polyvinyl pyrolidone and calcium stearate from the core formula were charged into a high shear granulator and dry mixed for less than 5 minutes and wet granulated using 2% solution of polyvinyl pyrolidone for another 2 minutes. The wet granules were dried in a fluid bed dryer to a loss of drying of less than 2% The dried granules were discharged into a Paterson Kelly V-Blender. The calcium stearate was then added to the V-Blender. The granules were blended for less than 10 minutes.

Step 1b. Preparation of the Core (Immediate Release Tablets):

The cores are tablets made from the granules prepared in Step 1a. A rotary press was set-up to produce capsule shaped tablets each weighing about 200 mg (a Manesty tablet press with 16 stations was used). Granules from Step1a were charged into a feed hopper and the tablet was produced from the double rotary press by applying suitable compression force to give tablets of required thickness, hardness and friability.

Step 2. Preparation of a Coating Suspension of the Ingredients of the Seal Coat:

(I) Water was added into a stainless steel vessel followed by Opadry White until no lumps are seen in the resulting suspension. (II) To a vortex of this suspension was added magnesium hydroxide until finely dispersed.

Step 3. Application of the Coating Suspension from Step 2 to Form a Seal Coat Surrounding the Tablet Cores from Step 1b:

Tablets from Step 1b were charged into a rotating drum of a side vented automated tablet coater. The suspension from Step 2 was applied to the tablet cores obtained from Step 1b, using a peristaltic pump and spray gun. The suspension was dried as a film onto the tablets, using heated air drawn through the tablet bed from an inlet fan. A sufficient amount of the suspension was applied to a weight gain of about 8 to 15%

Step 4. Preparation of a Coating Suspension of the Ingredients of the Alkaline Labile Enteric Coat:

(I) Water was added into a stainless steel vessel followed by sodium lauryl sulfate until dissolved. To this was gradually added Eudragit L as and L30D-55 dispersion, while stirring vigorously with a low shear mixer until all ingredients were finely dispersed in a suspension. (II) Glycerol monostearate was added to the Eudragit dispersion while stirring using a low shear mixer.

Step 5. Application of the Coating Suspension from Step 4 to Form an Alkaline Labile or Enteric Coat Surrounding the Tablets from Step 3:

Tablets from Step 3 were charged into a rotating drum of a side vented automated tablet coater. The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to form about 5 $mg/cm^2$ to about 12 $mg/cm^2$ of the coat surrounding the tablet.

Step 6. Preparation of a Coating Suspension of the Ingredients of the Acidifying Coat:

(I) Water was added into a stainless steel vessel followed by Opadry White until no lumps are seen in the resulting suspension. (II) To a vortex of this suspension was added citric acid followed by fumaric acid until finely dispersed.

Step 7. Application of the Coating Suspension from Step 6 to Form an Acidifying Coat Surrounding the Coated Tablet from Step 5:

Tablets from Step 5 were charged into a rotating drum of a side vented automated tablet coater. The suspension from Step 6 was applied to the tablets obtained from Step 5, using a peristaltic pump and spray gun. The suspension was dried as a film onto the tablets, using heated air drawn through the tablet bed from an inlet fan. A sufficient amount of the suspension was applied to a weight gain of about 30% wt/wt to about 70% wt/wt of the coated tablet from Step 5.

Step 8. Preparation of a Coating Suspension of the Ingredients of the Alkaline Labile Enteric Coat:

(I) Water was added into a stainless steel vessel followed by sodium lauryl sulfate until dissolved. To this was gradually added Eudragit L as and L30D-55 dispersion, while stirring vigorously with a low shear mixer until all ingredients were finely dispersed in a suspension. (II) Glycerol monostearate was added to the Eudragit dispersion while stirring using a low shear mixer.

Step 9. Application of the Coating Suspension from Step 8 to Form an Alkaline Labile or Enteric Coat Surrounding the Tablets from Step 7:

Tablets from Step 7 were charged into a rotating drum of a side vented automated tablet coater. The suspension from Step 8 was applied to the tablets obtained from Step 7, using a peristaltic pump and spray gun. The suspension was dried as a film onto the tablets, using heated air drawn through the tablet bed from an inlet fan. A sufficient amount of the suspension was applied to form about 3 $mg/cm^2$ to about 12 $mg/cm^2$ of the coat surrounding the tablet.

Example 29. Oxycodone Sustained Action (SA) 80 mg ODR Tablets

Each Tablet Contain 70 mg in the Core and 10 mg External to the Core

Formula for core

| Ingredients | % w/w |
|---|---|
| Oxycodone HCl | 18.34 |
| Polyethylene Oxide | 65.00 |
| Aluminum lake Blue #1 | 4.00 |
| Crospovidone | 2.00 |
| Microcrystalline cellulose | 11.66 |
| Eudragit RL | 2.00 |
| Magnesium stearate | 0.50 |

Formula for Loading Dose

| Ingredients | % w/w |
|---|---|
| Opadry White | 13.09 |
| Oxycodone HCl | 9.53 |
| Water | 77.38 |

Formula for Acid labile coat

| Ingredients | % w/w |
|---|---|
| Eudragit E (milled) | 9.73 |
| Sodium Lauryl sulfate | 0.974 |
| Stearic acid (milled) | 1.46 |
| Talc | 3.40 |
| Simethicone | 0.84 |
| Water | QS |

Formula for Alkalinizing Coat

| Ingredients | % w/w |
|---|---|
| Opadry White | 16.132 |
| Magnesium Hydroxide | 16.592 |
| Water | 67.276 |

Processing Techniques

Step 1a. Preparation of Granules for the Core:

All the ingredients with the exception of the magnesium stearate from the core formula were charged into a high shear granulator and dry mixed for less than 10 minutes. The dry mixed granules were discharged into a Paterson Kelly V-Blender. The magnesium stearate was then added to the V-Blender. The granules were blended for less than 10 minutes.

Step 1b. Preparation of the Core (Extended Release Tablets):

The cores are tablets made from the granules prepared in Step 1a. A rotary press was set-up to produce capsule shaped tablets each weighing about 400 mg (a Manesty tablet press with 16 stations was used). Granules from Step 1a were charged into a feed hopper and the tablet was produced from the double rotary press by applying suitable compression force to give tablets of required thickness, hardness and friability.

Step 2. Preparation of a Coating Suspension of the Ingredients for the Loading Dose to be Applied to the Tablet from Step 1b:

(I) Water was added into a stainless steel vessel. (II) Opadry was added while stirring with a propeller mixer until all ingredients are finely dispersed in a suspension. (III) Oxycodone HCl was added to the Opadry water mixture while stirring using a propeller mixer.

Step 3. Application of the Coating Suspension from Step 2 to Form Part of the Loading Dose Surrounding the Tablet from Step 1b:

Tablets from step 1b were charged into a rotating drum of a side vented automated Tablet coater (Rama Cota Tablet Film Coater was used). The suspension from Step 2 was applied to the tablets obtained from Step 1b, using a peristaltic pump and spray gun. The suspension was dried as a film onto the tablets, using heated air drawn through the tablet bed from an inlet fan. The suspension is applied to form a coat surrounding the tablet.

Step 4. Preparation of Acid Labile Coating Suspension to be Applied to the Tablet from Step3:

(I) Water was added into a stainless steel vessel followed by Sodium lauryl sulfate and stearic acid, step-by-step, while stirring vigorously with a high shear mixer until all ingredients are dissolved. (II) Eudragit E was added, step-by-step, while stirring vigorously with a high shear mixer until all ingredients were dissolved. (III) Talc was added, followed by simethicone while stirring using a high shear mixer until finely dispersed in the solution.

Step 5. Application of a Coating Suspension from Step 4 to Form an Acid Labile Coat Surrounding the Tablet from Step 3:

Tablets from step 3 were charged into the rotating drum of a side vented automated Tablet coater (Rama Cota Tablet Film Coater was used). The suspension from Step 4 was applied to the tablets obtained from Step 3, using a peristaltic pump and spray gun. The suspension was dried as a film onto the tablets, using heated air drawn through the tablet bed from an inlet fan. A sufficient amount of the suspension was applied to form about 4 mg/cm$^2$ to about 20 mg/cm$^2$ of the coat surrounding the tablet.

Step 6. Preparation of a Coating Suspension of the Ingredients of the Alkalinizing Coat:

(I) Water was added into a stainless steel vessel followed by Opadry White until no lumps are seen in the resulting suspension. (II) To a vortex of this suspension was added magnesium hydroxide until finely dispersed.

Step 7. Application of the Coating Suspension from Step 6 to Form an Alkalinizing Coat Surrounding the Coated Tablets from Step 5:

Tablets from Step 5 were charged into the rotating drum of a side vented automated Tablet coater (Rama Cota Tablet Film Coater was used). The suspension from Step 6 was applied to the tablets obtained from Step 5, using a peristaltic pump and spray gun. The suspension was dried as a film onto the tablets, using heated air drawn through the tablet bed from an inlet fan. A sufficient amount of the suspension was applied to form coat containing about 20 mg to 24 mg of magnesium hydroxide per coated tablet.

FIGS. 18 to 26 below show the results of the various tests for this example.

Example 30. Same as Example 29 Except that Each Tablet Contain 52.5 mg in the Core and 7.5 mg External to the Core

| Formula for core | |
|---|---|
| Ingredients | % w/w |
| Oxycodone HCl | 13.755 |
| Polyethylene Oxide | 61.00 |
| Aluminum lake Blue #1 | 4.00 |
| Crospovidone | 4.00 |
| Microcrystalline cellulose | 14.24 |
| Eudragit RL | 2.00 |
| Magnesium stearate | 1.00 |

| Formula for Loadind Dose | |
|---|---|
| Ingredients | % w/w |
| Opadry White | 12.73 |
| Oxycodone HCl | 7.86 |
| Water | 79.41 |

Example 31. Same as Example 29 Except that Each Tablet Contain 7.5 mg in the Core and 2.5 mg External to the Core

| Formula for core | |
|---|---|
| Ingredients | % w/w |
| Oxycodone HCl | 1.973 |
| Polyethylene Oxide | 80.21 |
| Aluminum lake Blue #1 | 4.00 |
| Crospovidone | 5.00 |
| Microcrystalline cellulose | 4.00 |
| Eudragit RL | 2.38 |
| Magnesium stearate | 0.44 |

| Formula for Loading Dose | |
|---|---|
| Ingredients | % w/w |
| Opadry White | 12.63 |
| Oxycodone HCl | 2.37 |
| Water | 85.00 |

Example 32. Same as Example 29 Except that Each Tablet Contain 8.75 mg in the Core and 1.25 mg External to the Core

| Formula for core | |
|---|---|
| Ingredients | % w/w |
| Oxycodone HCl | 2.822 |
| Polyethylene Oxide | 67.69 |
| Aluminum lake Blue #1 | 6.00 |
| Crospovidone | 2.00 |
| Microcrystalline cellulose | 18.99 |
| Eudragit RL | 2.00 |
| Magnesium stearate | 0.50 |

| Formula for Loading Dose | |
|---|---|
| Ingredients | % w/w |
| Opadry White | 15.091 |
| Oxycodone HCl | 1.612 |
| Water | 83.297 |

Example 33. Same as Example 29 Except that Each Tablet Contain 13.125 mg in the Core and 1.875 mg External to the Core

| Formula for core | |
|---|---|
| Ingredients | % w/w |
| Oxycodone HCl | 4.232 |
| Polyethylene Oxide | 73.69 |
| Aluminum lake Blue #1 | 4.00 |
| Crospovidone | 2.00 |
| Microcrystalline cellulose | 13.58 |
| Eudragit RL | 2.00 |
| Magnesium stearate | 0.50 |

| Formula for Loading Dose | |
|---|---|
| Ingredients | % w/w |
| Opadry White | 13.091 |
| Oxycodone HCl | 2.418 |
| Water | 84.490 |

Example 34. Same as Example 29 Except that Each Tablet Contain Oxymorphone HCl as Active Substance i.e., 35 mg in the Core and 5 mg External to the Core

| Formula for core | |
|---|---|
| Ingredients | % w/w |
| Oxymorphone HCl | 11.507 |
| Polyethylene Oxide | 64.27 |
| Aluminum lake Blue #1 | 4.00 |
| Crospovidone | 2.00 |
| Microcrystalline cellulose | 15.72 |
| Eudragit RL | 2.00 |
| Magnesium stearate | 0.50 |

| Formula for Loading Dose | |
|---|---|
| Ingredients | % w/w |
| Opadry White | 14.216 |
| Oxycodone HCl | 6.575 |
| Water | 79.461 |

I claim:

1. A method of inhibiting or preventing drug overdose in a patient, comprising administering to the patient a unit dose formulation comprising:
   at least one active substance, wherein release of said at least one active substance is inhibited when the number of unit dosage forms ingested exceeds a predetermined number;
   at least one actuator; and
   at least one regulator surrounding said at least one active substance and said at least one actuator,
   whereby when the unit dose formulation is exposed to a fluid media having a process variable, said process variable being pH, said at least one regulator is capable of adjusting the pH to inhibit the release of said at least one active substance via said at least one actuator, when the number of unit dosage forms exceeds the predetermined number.

2. A method according to claim 1, wherein said at least one regulator is present in an amount sufficient to raise the variable above the threshold, such that dissolution of said at least one actuator and release of said at least one active substance via the actuator is inhibited when the number of unit dosage forms ingested exceeds the predetermined number.

3. A method according to claim 1, wherein said at least one regulator is present in an amount sufficient to decrease the variable below the threshold, such that dissolution of said at least one actuator and release of said at least one active substance via the actuator is inhibited when the number of unit dosage forms ingested exceeds the predetermined number.

4. A method according to claim 1, wherein the fluid media is an acidic media.

5. A method according to claim 1, wherein the fluid media is a basic media.

6. A method according to claim 1, wherein the regulator and/or actuator is a physical/chemical barrier.

7. A method according to claim 1, wherein the regulator is a pH independent barrier and the actuator is a pH dependent barrier.

8. A method according to claim 1, wherein said at least one regulator comprises at least one alkalinizing agent.

9. A method according to claim 1, wherein said at least one alkalinizing agent is selected from the group consisting of alkaline earth metal salts, alkali metal salts, aluminum salts, amino acids, and amino acid derivatives.

10. A method according to claim 9, wherein said at least one alkalinizing agent is selected from the group consisting of magnesium hydroxide, magnesium trisilicate, aluminum hydroxide, magnesium oxide, calcium carbonate, sodium bicarbonate, sodium citrate, sodium carbonate, sodium acetate, magnesium carbonate, L-arginine, meglumine, and combinations thereof.

11. A method according to claim 10, wherein said at least one alkalinizing agent is magnesium hydroxide.

12. A method according to claim 1, wherein said at least one regulator comprises at least one acidifying agent.

13. A method according to claim 12, wherein said at least one regulator is selected from the group consisting of an inorganic acid, an organic acid, and combinations thereof.

14. A method according to claim 13, wherein said at least one acidifying agent is selected from the group consisting of hydrochloric acid, sulfuric acid, nitric acid, lactic acid, phosphoric acid, citric acid, malic acid, fumaric acid, stearic acid, tartaric acid, boric acid, borax, benzoic acid, and combinations thereof.

15. A method according to claim 14, wherein said at least one acidifying agent is fumaric acid and/or citric acid.

16. A method according to claim 1, wherein said at least one actuator comprises at least one acid labile substance.

17. A method according to claim 16, wherein said at least one acid labile substance is selected from the group consisting of sulfonamide-based polymers and copolymers, amine functional polymers and copolymers, polysaccharides, poly(vinylpyrrolidone-co-dimethylmaleic anhydride) (PVD), dimethylaminoethyl methacrylate copolymers, and combinations thereof.

18. A method according to claim 17, wherein the amine functional polymers is selected from the group consisting of polyvinyl pyridine polymers and copolymers.

19. A method according to claim 17, wherein the polysaccharides is chitosan.

20. A method according to claim 17, wherein the dimethylaminoethyl methacrylate copolymers are selected from the group consisting of 2-propenoic acid, 2-methyl-, butyl ester, polymer with 2-(dimethylamino)ethyl 2-methyl-2-propenoate and methyl 2-methyl-2-propenoate (Eudragit™ E, CAS Registry Number 24938-16-7), 2-propenoic acid, 2-methyl-, butyl ester, polymer with 2-(dimethylamino)ethyl 2-methyl-2-propenoate and methyl 2-methyl-2-propenoate interpolyelectrolyte complex (Eudragit™ E interpolyelectrolyte complex), 2-propenoic acid, 2-methyl-, butyl ester, polymer with 2-(dimethylamino)ethyl 2-methyl-2-propenoate and methyl 2-methyl-2-propenoate polyamopholyte complex (Eudragit™ E polyamopholyte complex), 2-propenoic acid, 2-methyl-, butyl ester, polymer with 2-(dimethylamino)ethyl 2-methyl-2-propenoate and methyl 2-methyl-2-propenoate complex with methacrylic acid and methyl methacrylate copolymer (1:2) (Eudragit™ E interpolyelectrolyte complex with Eudragit™ L), methacrylic acid and methyl methacrylate copolymer (1:2) (Eudragit™ S), derivatives thereof, and combinations thereof.

21. A method according to claim 20, wherein said at least one acid labile substance comprises 2-propenoic acid, 2-methyl-, butyl ester, polymer with 2-(dimethylamino)ethyl 2-methyl-2-propenoate and methyl 2-methyl-2-propenoate (Eudragit™ E, CAS Registry Number 24938-16-7).

22. A method according to claim 1, wherein said at least one actuator comprises at least one base labile substance.

23. A method according to claim 22, wherein said at least one base labile substance is selected from the group consisting of pharmaceutically acceptable ethers, esters, ketones, epoxies, polyamides, polysiloxanes, enteric polymers, anionic copolymers based on methacrylic acid and methyl methacrylate, and combinations thereof.

24. A method according to claim 23, wherein said at least one base labile substance comprises at least one enteric polymer.

25. A method according to claim 24, wherein said at least one enteric polymer is methacrylic acid and methyl methacrylate copolymer (1:1) (Eudragit™ L) or methacrylic acid and methyl methacrylate copolymer (1:2) (Eudragit™ S).

26. A method according to claim 1, wherein dissolution of said at least one actuator and release of said at least one active substance is reduced upon dissolution of a threshold amount of said at least one regulator.

27. A method according to claim 1, wherein dissolution of said at least one actuator and release of said at least one active substance decreases in the presence of increasing concentrations of at least one regulator.

28. A method according to claim 1, wherein the rate of dissolution of said at least one actuator is inversely proportional to the number of unit dose formulations ingested.

29. A method according to claim 1, wherein, when the number of unit dosage forms ingested exceeds a predetermined number, said at least one regulator increases the pH to inhibit dissolution of said at least one actuator and inhibit release of said at least one active substance.

30. A method according to claim 1, wherein, when the number of unit dosage forms ingested exceeds a predetermined number, said at least one regulator decreases the pH to inhibit dissolution of said at least one actuator and inhibit release of said at least one active substance.

31. A method according to claim 1, wherein the predetermined number is less than 20.

32. A method according to claim 31, wherein the predetermined number is 1, 2, 3, 4, or 5.

33. A method according to claim 31, wherein the predetermined number is 1 or 2.

34. A method according to claim 1, wherein, further comprising at least one agent selected from the group consisting of an abuse deterrent coloring agent; a controlled release agent; a viscosity imparting agent; a gelling agent; polyethylene oxide; crospovidone; N,N-dimethylmethanamine; 2-methylprop-2-enoic acid (Eudragit™ RL CAS Registry No. 51822-44-7); ethyl prop-2-enoate; methyl 2-methylprop-2-enoate; trimethyl-[2-(2-methylprop-2-enoyloxy)ethyl]azanium chloride (Eudragit™ RS CAS Registry No. 39316-06-8), and combinations thereof.

35. A method according to claim 1, wherein, further comprising at least one abuse deterrent coloring agent.

36. A method according to claim 34, wherein said at least one abuse deterrent coloring agent is brilliant blue.

37. A method according to claim 34, wherein said at least one abuse deterrent coloring agent is Aluminum Lake Blue #1.

38. A method according to claim 1, further comprising at least one agent selected from the group consisting of a chewing discouraging agent, a licking discouraging agent, an insufflation discouraging agent, a snorting discouraging agent, an inhalation discouraging agent, and combinations thereof.

39. A method according to claim 38, wherein wherein the inhalation discouraging agent is selected from the group consisting of a coloring agent, a tussigenic agent, an irritant, and combinations thereof.

40. A method according to claim 1, wherein said at least one active substance is at least one addictive substance.

41. A method according to claim 1, wherein said at least one active substance is at least one opioid agonist and/or at least one narcotic analgesic.

42. A method according to claim 1, wherein said at least one active substance has an analgesic ceiling effect.

43. A method according to claim 1, in the form of a bead, tablet, capsule, granule, and/or pellet.

44. A method according to claim 1, wherein said at least one active substance is in an amount of from about 0.1 mg to about 1000 mg; said at least one actuator is in an amount of from about 0.5 mg to about 500 mg; and/or said at least one regulator is in an amount of from about 0.5 mg to about 500 mg.

45. A method according to claim 1, wherein said at least one actuator is present in an amount of from 0.5 $mg/cm^2$ to 200 $mg/cm^2$ or from 1 $mg/cm^2$ to 100 $mg/cm^2$ or from 2 $mg/cm^2$ to 150 $mg/cm^2$ or from about 4 $mg/cm^2$ to about 100 $mg/cm^2$ or from 8 $mg/cm^2$ to 50 $mg/cm^2$.

46. A method according to claim 1, wherein said at least one actuator is used in an amount that yields from about 1% to about 200% weight gain, from about 1% to about 70% or from about 1% to about 50% weight gain based on the weight of the formulation.

47. A method according to claim 1, wherein said at least one regulator is used in an amount that yields from about 1% to about 200% weight gain, from about 5% to about 80%, from about 1% to about 70% weight gain, from about 1% to about 50% or from about 5% to about 50% weight gain based on the weight of the formulation.

48. A method according to claim 1, wherein release of said at least one active substance is a lag time, delayed release, no release or insignificant release of said at least one active substance.

49. A method according to claim 1 wherein at least one regulator substantially or completely surrounds said at least one active substance and said at least one actuator.

\* \* \* \* \*